(12) United States Patent
Choi et al.

(10) Patent No.: US 10,905,682 B2
(45) Date of Patent: Feb. 2, 2021

(54) USE OF MITOCHONDRIAL IRON CHELATORS FOR TREATMENT OF CHRONIC OBSTRUCTIVE PULMONARY DISEASE

(71) Applicant: Cornell University, Ithaca, NY (US)

(72) Inventors: Augustine M. K. Choi, New York, NY (US); Suzanne M. Cloonan, New York, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 15/780,030

(22) PCT Filed: Dec. 1, 2016

(86) PCT No.: PCT/US2016/064375
§ 371 (c)(1),
(2) Date: May 30, 2018

(87) PCT Pub. No.: WO2017/096013
PCT Pub. Date: Jun. 8, 2017

(65) Prior Publication Data
US 2018/0360815 A1  Dec. 20, 2018

Related U.S. Application Data

(60) Provisional application No. 62/261,364, filed on Dec. 1, 2015.

(51) Int. Cl.
*A61K 31/4412* (2006.01)
*A61P 11/00* (2006.01)
*A61K 45/06* (2006.01)
*A61K 9/00* (2006.01)

(52) U.S. Cl.
CPC .......... *A61K 31/4412* (2013.01); *A61K 45/06* (2013.01); *A61P 11/00* (2018.01); *A61K 9/0078* (2013.01)

(58) Field of Classification Search
CPC .. A61K 31/4412; A61K 45/06; A61K 9/0078; A61P 11/00
See application file for complete search history.

(56) References Cited

U.S. PATENT DOCUMENTS

| | | |
|---|---|---|
| 6,005,009 A | 12/1999 | Murad et al. |
| 7,238,661 B2 | 7/2007 | Glynn et al. |
| 8,247,376 B2 | 8/2012 | Barasch et al. |
| 8,629,131 B2 | 1/2014 | Klaus et al. |
| 2006/0040980 A1 | 2/2006 | Lind et al. |
| 2008/0066741 A1 | 3/2008 | LeMahieu et al. |
| 2010/0035992 A1 | 2/2010 | Bhushan et al. |
| 2010/0086531 A1 | 4/2010 | Henry et al. |
| 2012/0012123 A1 | 1/2012 | Gavish et al. |
| 2012/0184586 A1 | 7/2012 | Bergeron |
| 2012/0282353 A1 | 11/2012 | Roth et al. |
| 2014/0220112 A1 | 8/2014 | Szoka, Jr. et al. |
| 2015/0196512 A1 | 7/2015 | Nicolls et al. |
| 2015/0196543 A1 | 7/2015 | Surber |
| 2016/0175436 A1 | 6/2016 | Bascomb et al. |
| 2016/0199437 A1 | 7/2016 | Wilson |

FOREIGN PATENT DOCUMENTS

| | | |
|---|---|---|
| WO | 2014100233 A1 | 6/2014 |
| WO | 2015/019381 A1 | 2/2015 |
| WO | 2016103260 A1 | 6/2016 |

OTHER PUBLICATIONS

Douglas B Kell, Iron behaving badly: inappropriate iron chelation as a major contributor to the aetiology of vascular and other progressive inflammatory and degenerative diseases, BMC Medical Genomics 2009, 2:2 (Year: 2009).*

Cloonan, S.M., et al., Mitochondrial iron chelation ameliorates cigarette smoke-induced bronchitis and emphysema in mice, Nature Medicine, Jan. 11, 2016, vol. 22, pp. 163-174.

Persson et al., Iron-binding drugs targeted to lysosomes: a potential strategy to treat inflammatory lung disorders (Abstract Only), Expert Opin Investig Drugs, vol. 14, No. 8, pp. 997-1008. Aug. 2005.

* cited by examiner

*Primary Examiner* — Sarah Pihonak
*Assistant Examiner* — Jason Deck
(74) *Attorney, Agent, or Firm* — Hodgson Russ LLP

(57) ABSTRACT

A method for treating one or more symptoms of COPD comprising administering to an in need of treatment a therapeutically effect amount of one or more mitochondrial iron chelators. The mitochondrial iron chelator can be deferiprone. Compostions comprising mitochondrial iron chelators suitable for administration are also disclosed.

12 Claims, 50 Drawing Sheets f g i h i c d c d f g a b d c

| Sample | Bp peak | Library size | Conc (ug/ml) | Qubit nM | qPCR nM |
|---|---|---|---|---|---|
| IRP2 CTL | 283 | 183950 | 30.6 | 166.3496 | 232.95 |
| IRP2 DFO | 276 | 179400 | 35.8 | 199.5541 | 308.78 |
| IgG CTL | 275 | 178750 | 32 | 179.021 | 295.9 |
| IgG DFO | 272 | 176800 | 31.2 | 176.4706 | 325.54 | a b e f

USE OF MITOCHONDRIAL IRON CHELATORS FOR TREATMENT OF CHRONIC OBSTRUCTIVE PULMONARY DISEASE

CROSS-REFERENCE TO RELATED APPLICATIONS

This application claims priority to U.S. Provisional application no. 62/261,364, filed on Dec. 1, 2015, the disclosure of which is incorporated herein by reference.

STATEMENT REGARDING FEDERALLY SPONSORED RESEARCH

This invention was made with government support under Grant Numbers HL105339, HL114501, and HL125899 awarded by the National Institutes of Health. The government has certain rights in the invention.

BACKGROUND OF THE DISCLOSURE

Chronic obstructive pulmonary disease (COPD) presents as a complex debilitating lung disease that encompasses a variety of clinical and pathologic phenotypes ranging from airway inflammation (chronic bronchitis) to destruction of lung tissue (emphysema) and remodeling of the small airways. The pathogenesis of COPD remains poorly understood, but involves aberrant inflammatory and dysregulated cellular responses of the lung to cigarette smoke (CS) exposure. CS exposure remains the greatest environmental risk factor for COPD; however, multiple studies have suggested that genetic factors influence susceptibility to COPD. Current treatments for COPD have limited efficacy in inhibiting the chronic inflammation associated with the disease. Moreover, they do not reverse the pathology of disease and fail to modify the factors that initiate and drive the long-term progression of the disease. Thus, there is a need for new therapies that can prevent the induction and progression of COPD.

SUMMARY OF THE DISCLOSURE

In this disclosure, we delineate the function of the COPD susceptibility gene Iron Regulating Protein gene, IRP2, in the pathogenesis of CS-induced COPD by integrating human COPD expression data with experimental mouse models of COPD. Our studies are the first to characterize a functional role for IRP2 in the lung wherein IRP2 promotes mitochondrial dysfunction in experimental COPD by regulating mitochondrial iron loading and cytochrome c oxidase. We show that mitochondrial iron chelation alleviates established disease. Based on these data, this disclosure provides methods and compositions for therapeutic approaches for COPD and other lung diseases or conditions.

In one aspect, this disclosure provides a method for treatment of lung conditions, such as, for example, COPD. The method comprises administering to an individual in need of treatment, a composition comprising a mitochondrial iron chelator. For example, a composition comprising deferiprone may be used.

In one aspect, this disclosure provides compositions comprising mitochondrial iron chelators suitable for administration by inhalation. For example, the compositions may be aerosolized and administered via a nebulizer.

In one aspect, this disclosure provides kits for administration of compositions comprising one or more mitochondrial iron chelators. The kits can comprise the formulation in a ready-to-use form, and instructions for use, and optionally, a delivery device, such as a nebulizer (for inhalation), or a patch (for transdermal delivery).

DESCRIPTION OF THE DISCLOSURE

Figure 1:
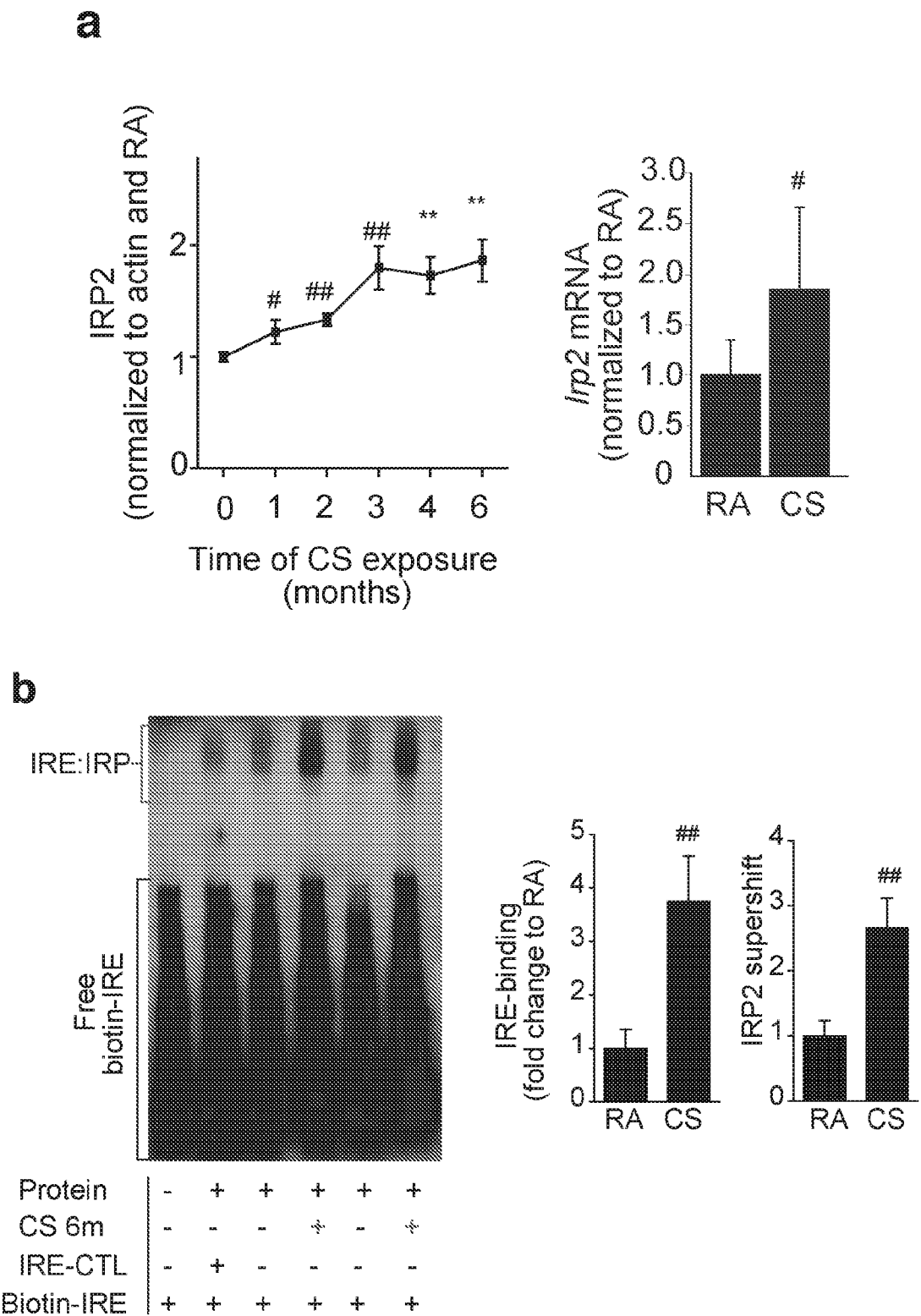
FIG. 1. IRP2 is pathogenic in experimental COPD. (a) IRP2 protein (left), mRNA (right) (n=8 per group) and (b) representative (n=4) EMSA (left) with quantification of total-IRP (n=5 per group) and specific-IRP2 activity (n=3 per group) in wild-type (WT) WT mouse lungs exposed to room air (RA) or CS (1-6 months). (c-d) IRP1 protein expression (n=3 per group) and representative IRP2 (d) immunostaining (arrows indicate IRP2) in mouse lungs exposed to RA or CS. (e) Representative Hematoxylin-Eosin stained lung-sections (left), mean chord length (middle), weighted mean diameters (right) and (f) representative trichrome stained lung-sections (left) and ECM protein thickness around small airways (right) in WT and $Irp2^{-/-}$ mice exposed to RA or CS (6 months), staining; n=2 technical replicates. (g) Cleaved caspase-3 (left) (ELISA, n=7 per group) and MMP-9 (right) (ELISA, WTRA n=5; WTCS n=3; $Irp2^{-/-}$ RA, CS n=6) levels in whole lung of WT and $Irp2^{-/-}$ mice exposed to RA or CS (6 months), n=2 technical replicates. (h) $^{99m}$Tc-sc clearance over 1-3 hours (left) in WT mouse lungs exposed to RA (n=9) or CS (n=10) (1 month). 3 hour $^{99m}$Tc-SC clearance (right), (i) BALF IL-33 (left, ELISA; WTRA n=3; WTCS n=5; $Irp2^{-/-}$ RA n=5; $Irp2^{-/-}$C n=6) and BALF IL-6 protein concentrations (right, ELISA, n=3 per group) in WT and $Irp2^{-/-}$ mice exposed to RA or CS (1 month). Scale bars (d-f) 50 μM. All data are mean±s.e.m.; *P<0.05, P<0.01, *P<0.005 by one-way ANOVA with Bonferroni correction. #P<0.05, ##P<0.01, ####P<0.005 by student's unpaired t-test. n.s.; not-significant.
Figure 1:
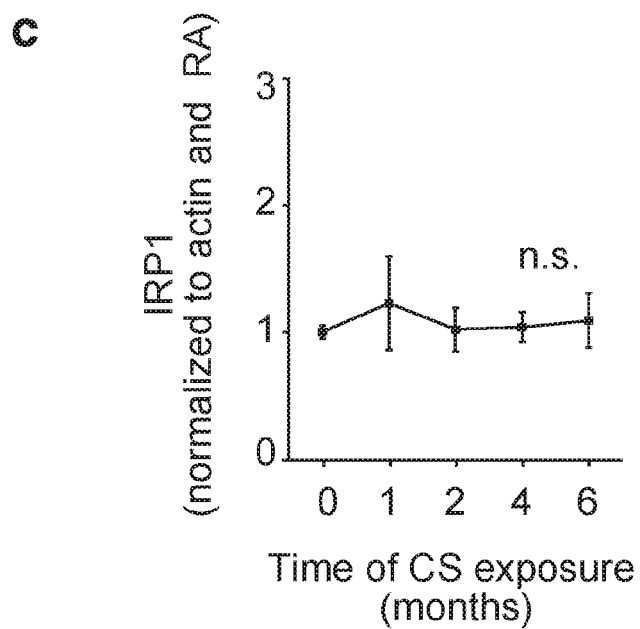
Figure 1:
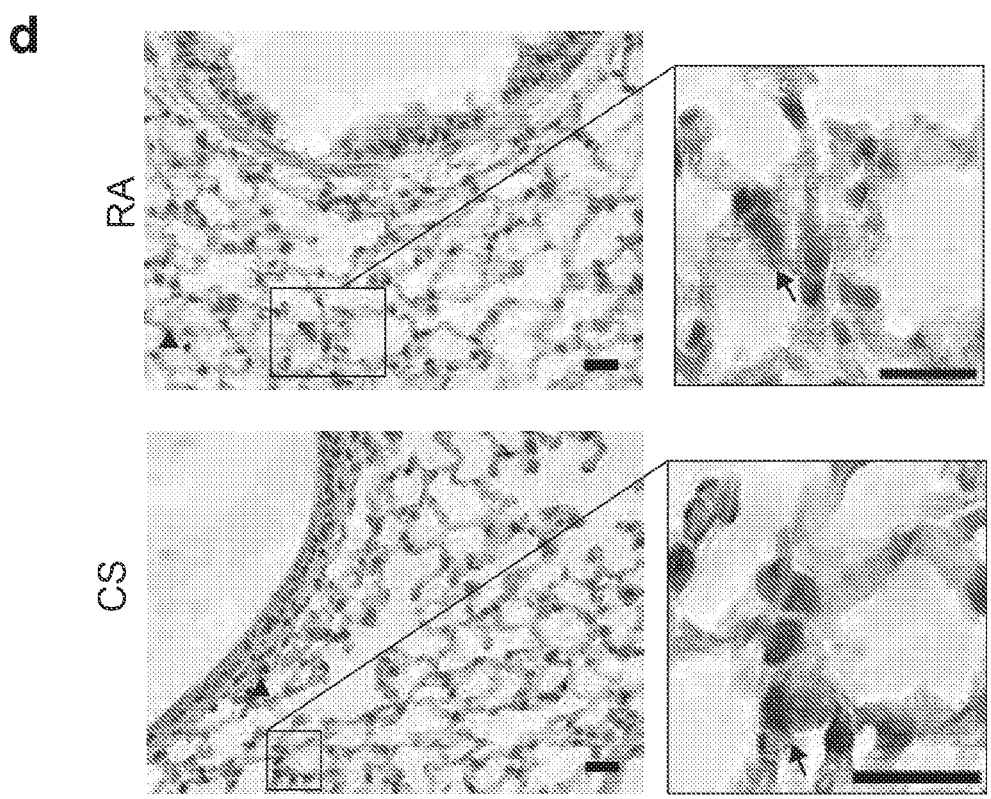
Figure 1:
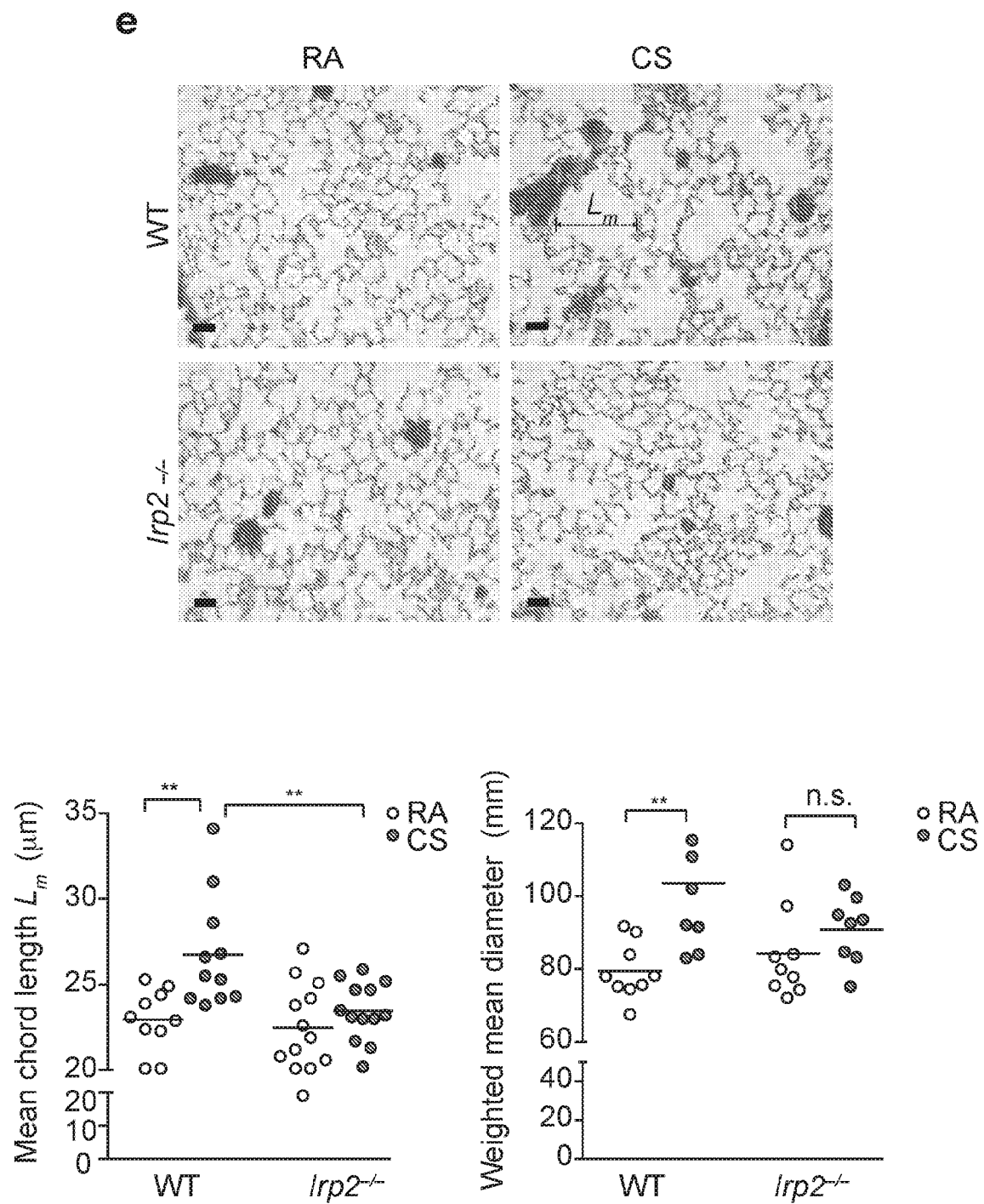
Figure 1:
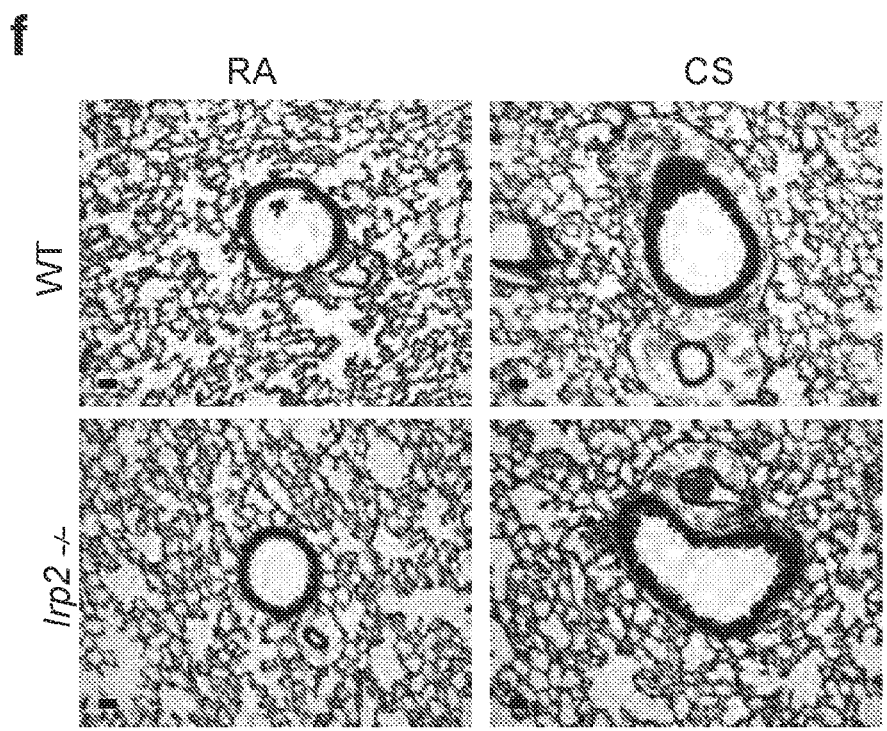
Figure 1:
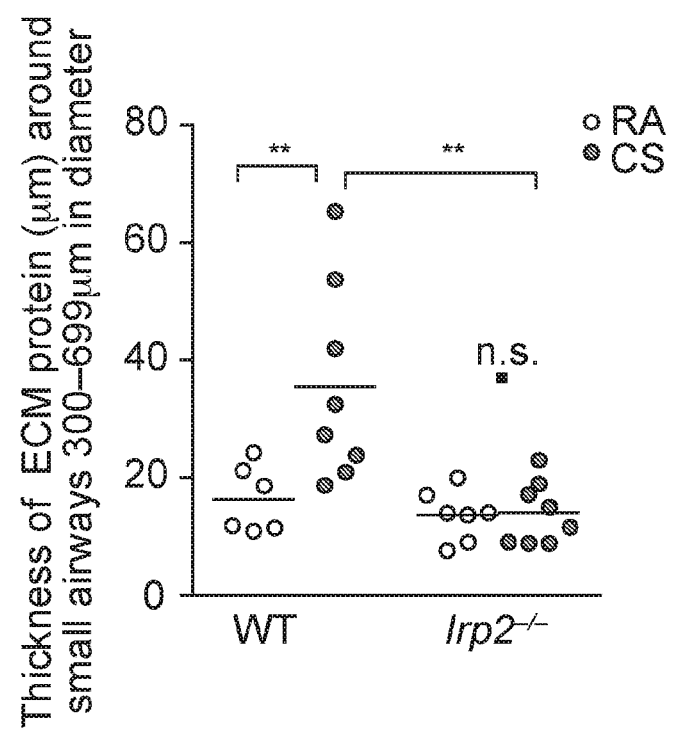
Figure 1:
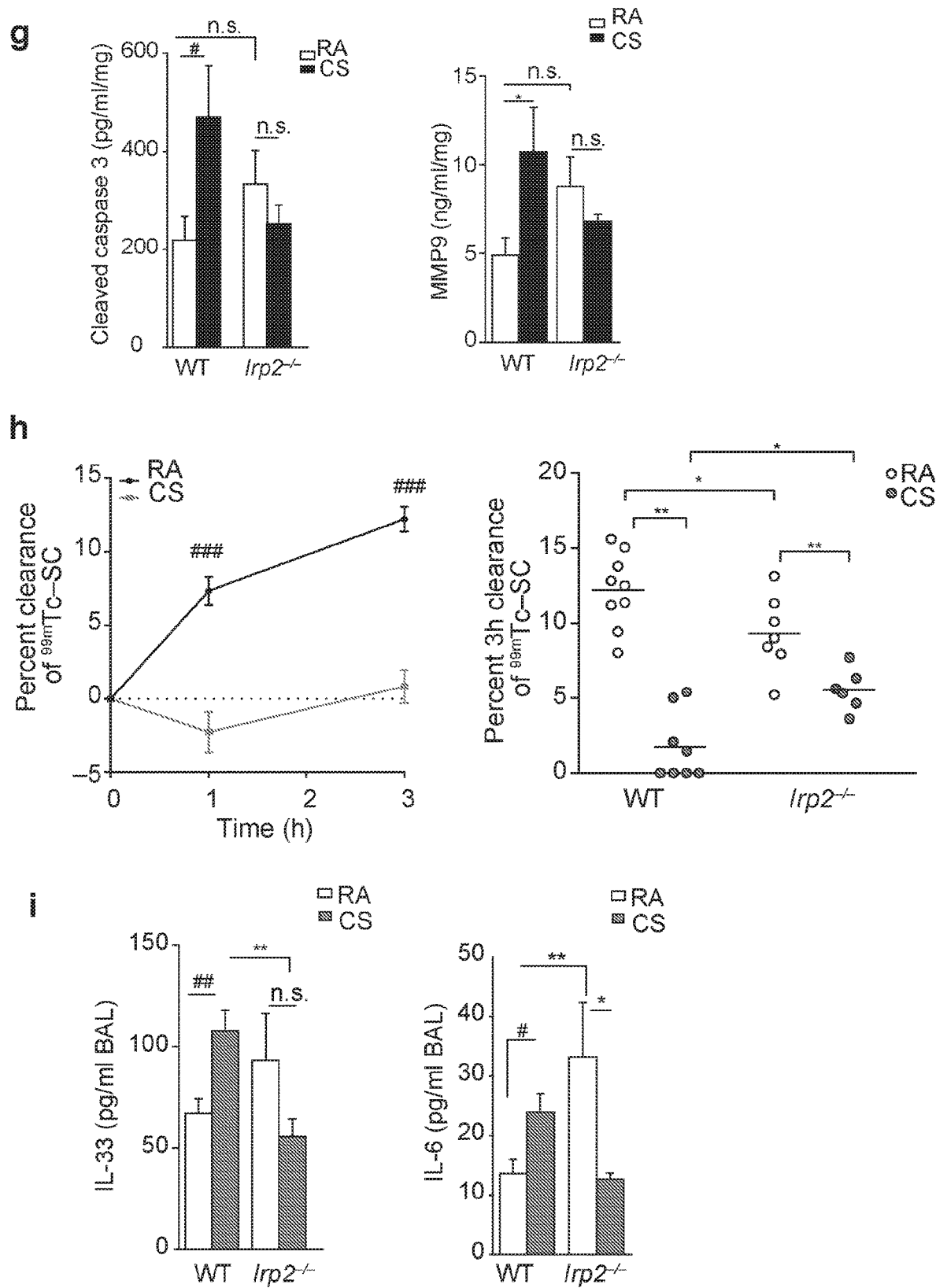

The iron regulatory proteins (IRPs) IRP1 and IRP2 regulate cellular iron homeostasis, with IRP2 serving as the major regulatory protein in mammalian cells. IRPs have important physiological roles in the duodenum, spinal cord and central nervous system, and in the pathogenesis of pulmonary hypertension and neurodegenerative diseases. In the setting of iron depletion, IRPs decrease iron storage and increase iron uptake by the binding to iron response elements (IREs) located in mRNA resulting in translational repression or stabilization of the transcripts. The critical physiologic function of IRP2 in the lung, in particular the mRNA transcripts targeted by IRP2 are not well known, nor is it clear whether IRP2 has a role in the response of the lung to CS exposure or in the pathogenesis of CS-induced COPD.

In this disclosure, using two well-established human COPD cohorts, we demonstrate that IRP2 regulates mitochondrial-related pathways in the lung, showing a strong association between the differential-expression of mitochondrial genes and IRP2 expression in COPD subjects. Excess mitochondrial iron may generate hydroxyl radicals that promote inflammation, cell death and oxidative stress, all of which contribute to the pathogenesis of COPD. Our studies indicate IRP2 is involved in cigarette smoke-induced stress responses, particularly those converging on the mitochondria, which, if sustained for long periods of time, may have deleterious effects at the molecular, cellular and tissue level leading to mitochondrial dysfunction and subsequent cell death and the initiation of inflammation ultimately resulting in the development of COPD. Our study provides basis for the use of mitochondrial iron chelators as therapeutic approaches for COPD.

In one aspect, this disclosure provides a method for alleviating the symptoms of, or treating, a lung condition, such as COPD, in an individual comprising administering to an individual in need of treatment, a therapeutically effective amount of at least one intraorganellar iron chelator. Intraorganellar iron chelators are those that can chelate iron within cellular organelle such as lysosomes, endosomes, autophagosomes, mitochondria and the like. In one embodiment, the intraorganellar iron chelator is a mitochondrial iron chelator. Whenever the term "mitochondrial iron chelator" is used in this disclosure, the teachings are intended to applicable to intraorganellar iron chelators also. A Mitochondrial iron chelators possess the ability to cross or pass through biological membranes, such as plasma, mitochondrial, lysosomal or autophagosomal membranes. An example is deferiprone (DFP). Compared with the positively charged molecule of deferoxamine, deferiprone molecule is neutral and has a significantly greater capacity to permeate biological membranes. After binding iron, the DFP-iron complex becomes hydrophilic, meaning it can also chelate iron from the cytosol and other hydrophilic compartments. In contrast, deferoxamine is only suitable for the chelation of extracellular or plasma membrane bound iron, entering cells only by endocytosis and unable to cross inside intracellular organelles such as mitochondria. At high doses deferoxamine may accumulate inside lysosomal compartments only through direct delivery from the endosome. Mitochondrial iron chelators (and other intraoganellar iron chelators) target different iron pools compared to general iron chelators.

In one aspect, the present disclosure provides compositions useful for treatment of COPD. The compositions comprise or consist essentially of one or more mitochondrial iron chelator. The composition may contain a mitochondrial iron chelator, such as deferiprone, as the only active agent—meaning it does not contain another agent at levels sufficient to alleviate any symptom of COPD. In one embodiment, the composition does not contain any other iron chelator. In one embodiment, it does not contain any other therapeutic agent for COPD or any other lung condition. In one embodiment, the composition contains only deferiprone in a pharmaceutical carrier. The compositions may be formulated for delivery via modes suitable for COPD, such as oral, inhalation, or transdermal routes.

Mitochondrial iron-chelators, such as siderophores, can be used in the present disclosure. Suitable examples of mitochondrial iron-chelators include deferiprone and derivatives thereof, including pegylated derivatives, such as pegylated 3-hydroxypyridin-4-ones derivatives, 8-HQ-based iron chelators, 5-((methylamino)methyl)-8-hydroxy quinoline (Q1) and 5-(morpholinomethyl)-8-hydroxyquinoline (Q4) (Mena et al. Biochemical and Biophysical Research Communications 463 (2015) 787e792); 7,8-dihydroxy-4-((methylamino)methyl)-2H-chromen-2-one (DHC12) (Aguirre et al., ACS Chemical Neurosci., 2015); (4,5)-2-(2-hydroxy-3-{2-[2-(2-methoxyethoxy)ethoxy]-ethoxy}phenyl)-4-methyl-4,5-dihydrothiazole-1,3-thiazole-4-carboxylic acid (deferitazole 3); bidentate, iron (III) chelators (Abbate et al., Biochem. J. (2015) 469,357-366 doi:10.1042/BJ20150149); 1-(N-acetyl-6-aminohexyl)-3-hydroxy-2-methylpyridin-4-one (CM1) (Pangjit et al., Royal Pharmaceutical Society, Journal of Pharmacy and Pharmacology, 67, pp. 703-713); catechol-based hexadentate iron chelators (Reelfs et al., Journal of Investigative Dermatology (2016) 136, 1692e1700; doi:10.1016/j .jid.2016.03.041, examples includes compound #3); 5-{N-methyl-N-propargylaminomethyl}-8-hydroxyquinoline (M30) and 5-{4-propargylpiperazin-1-ylmethyl}-8-hydroxyquinoline (HLA20) (Mechlovich et al., J. Pharmacol Expt. Therap. 2010 June; 333(3):874-82. doi: 10.1124/jpet.109.164269. Epub 2010 March 17).

Lung conditions that can be treated by the present method include COPD, lung fibrosis, and acute lung injury. The present disclosure is particularly relevant to lung injury, including COPD, caused by cigarette smoking. COPD is a pulmonary disease which progresses slowly. The hallmark features of COPD include one or more of the following: lung inflammation, impaired lung function, pulmonary emphysema, impairment of mucociliary clearance, mucus hypersecretion, small airway wall thickening and remodeling, vascular remodeling, lymphoid aggregation, and/or chronic bronchitis. Subsequently, short breath frequently worsens and a cough, associated with extensive and sometimes prolonged discharge and obstructed breathing leading up to breathlessness (dyspnea), manifests itself Smoking is considered to be responsible for most of the cases of COPD.

The term "therapeutically effective amount" as used herein refers to an amount of an agent sufficient to achieve, in a single or multiple doses, the intended purpose of treatment. For example, an effective amount to treat COPD is an amount sufficient to alleviate symptoms of COPD. For example, symptoms associated with COPD can be emphysema, excessive airway mucus, recurrent pulmonary infections and chronic bronchitis.

The exact amount desired or required will vary depending on the particular compound or composition used, its mode of administration, patient specifics and the like. Appropriate effective amount can be determined by one of ordinary skill in the art informed by the instant disclosure using only routine experimentation.

Within the meaning of the disclosure, "treatment" also includes relapse, or prophylaxis as well as the treatment of acute or chronic signs, symptoms and/or malfunctions. The treatment can be orientated symptomatically, for example, to suppress symptoms. It can be effected over a short period, be oriented over a medium term, or can be a long-term treatment, for example within the context of a maintenance therapy. For example, treatment can result in amelioration of one or more of the following symptoms: lung inflammation, impaired lung function, pulmonary emphysema, impairment of mucociliary clearance, mucus hypersecretion, small airway wall thickening and remodeling, vascular remodeling, lymphoid aggregation, and/or chronic bronchitis.

Where a range of values is provided in this disclosure, it should be understood that each intervening value, to the tenth of the unit of the lower limit between the upper and lower limit of that range, and any other intervening value in that stated range is encompassed within the invention, unless clearly indicated otherwise. Narrower ranges within the larger disclosed ranges are also intended to be encompassed within the disclosure.

The pharmaceutical composition of the invention may be administered in any route that is appropriate, including but not limited to parenteral or oral administration. The pharmaceutical compositions for parenteral administration include solutions, suspensions, emulsions, and solid injectable compositions that are dissolved or suspended in a solvent immediately before use. The injections may be prepared by dissolving, suspending or emulsifying one or more of the active ingredients in a diluent. Examples of diluents are distilled water for injection, physiological saline, physiologic buffer, vegetable oil, alcohol, or a combinations thereof. Further, the injections may contain stabilizers, solubilizers, suspending agents, emulsifiers, soothing agents, buffers, preservatives, etc. The injections, are sterilized in the final formulation step or prepared by sterile procedure. The pharmaceutical composition of the invention may also be formulated into a sterile solid preparation, for example, by freeze-drying, and may be used after sterilized or dissolved in sterile injectable water or other sterile diluent(s) immediately before use. The compositions described can include one or more standard pharmaceutically acceptable carriers. Examples of pharmaceutically acceptable carriers can be found in: *Remington: The Science and Practice of Pharmacy* (2005) 21st Edition, Philadelphia, Pa. Lippincott Williams & Wilkins.

Suitable stabilizers include fatty acids, including lecithin, cationic lipids, particularly phospholipids, and proteins, such as albumin. Other stabilizers include Polyvinylpyrrolidone (PVP), and Chitosan. Cationic lipids are molecules that are positively charged molecules, e.g., quaternary ammonium salts. Examples of suitable cationic lipids include 2-distearoyl-sn-glycero-3-phosphocholine (DSPC); 1,2-dipalmitoyl-sn-glycero-3-phosphocholine (DPPC) and the like.

Various methods known to those skilled in the art can be used to introduce (i.e., administer) the compositions of the disclosure to an individual. For example, an agent or mixture of agents, or compositions containing one or more active agents, can be administered in any manner including, but not limited to, orally, parenterally, sublingually, transdermally, rectally, transmucosally, topically, via inhalation, via buccal administration, or combinations thereof. Parenteral administration includes, but is not limited to, intravenous, intraarterial, intracranial, intradermal, subcutaneous, intraperitoneal, subcutaneous, intramuscular, intrathecal, and intraarticular. The agents(s) can also be administered in the form of an implant, which allows a slow release of the compound(s), as well as a slow controlled i.v. infusion.

A method suitable for use for COPD is direct delivery of the therapeutic compositions to the respiratory system. For example, the mitochondrial iron chelator can be delivered in the form of an aerosol spray from a device (such as one having a pressurized metered dose inhaler) with the use of a suitable propellant, e.g., dichlorodifluoromethane, trichlorofluoromethane, dichloro-tetrafluoroethane, or carbon dioxide. The mitochondrial iron chelator in the aerosol spray may be in a powder form administered using a dry powder inhaler, or in aqueous liquid aerosol form using a nebulizer. Such methods are described in Remington's Pharmaceutical Sciences, $18^{th}$ ed. Mack Publishing Co., Easton, Pa. (1990), which is incorporated by reference herein for such teachings.

If formulations are desired to be delivered in liquid form, then the liquid formulations can be directly aerosolized. Lyophilized powder can be aerosolized after reconstitution. The terms "aerosol," "aerosol particles," "aerosolized formulation" and the like mean particles of formulation comprised of pharmaceutically active drug and carrier which are formed for aerosol delivery, e.g. upon forcing the formulation through a nozzle using a jet or ultrasonic nebulizer. The particles can have a diameter in the range of 0.5 to 12 microns (and all values therebetween) for delivery to the pulmonary tract. For example, particles can have an average diameter (size) of 0.5, 1, 2, 3, 4, 5, 6, 7, 8, 9, 10, 11 or 12 microns. The compositions can have at least 50, 60, 70, 80, 90, 95, or 99% of the particles have a size within 2 microns or 1 micron of the average size. To facilitate delivery of DFP to the lung, liposomes can be used. DFP is a hydrophilic molecule and will be located in the aqueous compartment, such as in the aqueous layers between the vesicle bilayer walls or in the aqueous internal compartment. Liposomes have high tolerance and little to no toxicity and are particularly suitable for application in the lung. There are a number of approved liposomal formulations already on the market, including the products DAUNOXOME® (daunorubicin), AMBISOME® (amphotericin B), and Heparin-Pur® Heparin-pur (liposomal heparin spray). The combination of DFP into liposomal delivery systems also allows for the sustained release of DFP over a period of time, in contrast to one dose at one time. It may also prevent or minimize the compound from crossing the air-blood barrier into the systemic circulation and causing systemic side effects (Taylor et al., Thorax, vol. 47, 1992, pp. 257-259).

Mitochondrial iron chelators may also be included in an electronic nicotine delivery system. Electronic nicotine delivery systems (ENDS) include electronic cigarettes, or e-cigarettes, e-pens, e-pipes, e-hookah, and e-cigars. These devices allow users to inhale an aerosol (vapor) containing nicotine or other substances. These electrically-driven devices comprise a battery part (usually a lithium battery) and an atomizer where liquid is stored and is aerosolized by applying energy and generating heat to a resistance encircling a wick. The liquid used may be propylene glycol, glycerol, distilled water and nicotine.

The mitochondrial iron chelator (which may be referred to herein as an active agent) can be in the form of a nanoparticle and the nanoparticles can comprise the active agent and a pharmaceutical carrier. The nanoparticle can comprise or consist essentially of the active agent at a concentration of up to about from 5% to about 90% of the total weight. In one embodiment, the mitochondrial iron chelator is the only active agent in the nanoparticle. In some embodiments the formulations can comprise from 30 to 70% by weight of the mitochondrial iron chelator. The remaining portion of the nanoparticles can be made up of stabilizers, fillers and the like. The nanoparticles can have a size of about 10 nm to 10 µm (and all values therebetween).

Formulations may be delivered using a fluorocarbon formulation or other propellant and a metered dose dispenser. Powder inhalers and nebulizers are known in the art that can be used for administration of the present compositions. Nebulizers, which convert liquids into aerosols of a size that can be inhaled into the lower respiratory tract, can be used in conjunction with a mask or a mouthpiece. Nebulizers suitable for use in certain aspects of the methods described herein can be either pneumatic or ultrasonic, and continuous or intermittent. Nebulizers may be jet nebulizers operated by a pressurized flow of air using a portable compressor or central air supply in a medical facility, ultrasonic nebulizers incorporating a piezo-crystal to provide the energy for generating the aerosol out of an ultrasonic fountain, or electronic nebulizers based on the principle of a perforated vibrating membrane. Nebulizers are available commercially. For example, Omron Micro-Air Electronic Nebulizer System or similar can be used.

A nebulizer can comprise a ready-to-use inhalation composition comprising therapeutically effective amount of a mitochondrial iron chelator, such as deferiprone. The nebulizer units can contain suitable amounts of pre-sterilized formulations, such as, for example, 0.25 ml to 10.0 ml (and all volumes there between) of the formulations. The ready-to-use units can be made of glass, polyethylene, or any other containers suitable for use with nebulizers.

The present formulations may be delivered via the cutaneous route. For example, transdermal, intradermal, subcutaneous delivery modes may be used. A mitochondrial iron chelator may be admixed with one or more excipients, e.g., pH adjusters, preservatives, and/or penetration enhancers in order to form a solution, ointment, cream, lotion, or gel. Examples of skin penetration enhancers include physical enhancers (ultrasound, iontophoresis, electroporation, magnetophoresis, microneedle), vesicles, particulate systems (liposome, niosome, transfersome, microemulsion, solid lipid nanoparticle), and chemical enhancers (sulfoxides, azones, glycols, alkanols, terpenes, etc.). Further examples of chemical enhancers include, e.g., propylene glycol, polyethylene glycol, isopropanol, ethanol, oleic acid, N-methylpyrrolidone, which increase the permeability of the skin to the compounds, and permit the compounds to penetrate through the skin to deeper tissues. Such a composition may form a constituent of a transdermal delivery system, such as, for example, a skin patch.

The present method can be used in humans as well as non-human animals. The formulations can be administered to an individual in need of treatment. For example, an individual in need of treatment can be an individual who smokes, who has ceased smoking or who is trying to cease smoking. An individual in need of treatment can be an individual with diagnosed COPD and its subtypes (emphysema, chronic bronchitis, and chronic obstructive asthma). Diagnosis of COPD includes one or more of the following symptoms; dyspnea at rest or on exertion, cough with or without sputum production, progressive limitation of activity, history of exposure to triggers of COPD (e.g., tobacco smoke, occupational dust, indoor biomass smoke), a family history of chronic lung disease. The diagnosis of COPD can be confirmed by the following; a) spirometry demonstrating airflow limitation (i.e., a forced expiratory volume in one second/forced vital capacity [FEV1/FVC] ratio less than 0.7 or less than the lower limit of normal [LLN] PLUS an FEV1 less than 80 percent of predicted) that is incompletely reversible after the administration of an inhaled bronchodilator, and/or b) absence of an alternative explanation for the symptoms and airflow limitation.

Imaging—Chest radiography and computed tomography (CT) are typically performed in patients with COPD when the cause of dyspnea or sputum production is unclear and during acute exacerbations.

Mitochondrial iron chelation can be used for patients with early onset (Alpha-1 antitrypsin or other genetically related forms of COPD), smoking-related (including passive smoking) COPD as well as other infection-related triggers of COPD exacerbations. Given that respiratory and systemic inflammation continues unabated despite smoking cessation, mitochondrial iron chelation will be useful for both current smokers and ever smokers. Specifically, whilst mortality rates decline after smoking cessation compared with continuing smoking, the mortality risk in ex-smokers is still elevated in comparison with never-smokers, even after many years of abstinence from smoking and so deferiprone or similar mitochondrial iron chelator can be used to enhance survival and mortality rates after long term smoking. Mitochondrial iron chelators such as deferiprone may help to mitigate the ongoing inflammation and provide an innovative approach to minimize further airway and parenchymal remodeling that is independent of smoking status. Deferiprone can have therapeutic benefits in reducing the risk or impact of acute exacerbations, which may in turn restore the balance of the pulmonary and systemic inflammatory response and enhance the subsequent innate repair processes. DFP may attenuate the inflammatory process during and after acute exacerbations. This should minimize clinical impact during an acute event and prevent future exacerbations. We have shown that excessive iron deposition inside mitochondria of the lung associates with COPD disease progression in murine models. Therefore, identifying and treating active pathological processes, such as using DFP to alleviate mitochondrial iron loading may mitigate disease progression and/or prevent or treat active exacerbation. There are many relevant phenotypes for whom DFP may prove useful, including α1-antitrypsin deficiency, frequent exacerbations, chronic bronchitis and upper lobe emphysema.

In one aspect, the disclosure provides a method for making a medicament comprising a mitochondrial iron chelator for use in the treatment of COPD and related lung conditions comprising providing a mitochondrial iron chelator in a suitable carrier, aerosolizing the formulation such that the formulation can be administered via inhalation, and optionally providing the formulation in a suitable dispenser, such as a nebulizer. Instead of providing the formulation in an aerosolized form, the disclosure also provides methods for providing the formulations for administration via oral or cutaneous routes.

The following example is provided to illustrate the invention and is not intended to be restrictive.

EXAMPLE 1

Results

IRP2 Deficient Mice Resisted Experimental COPD

To characterize the functional role of IRP2 in the pathogenesis of COPD, we used two well-established experimental models of CS-induced COPD, namely CS-induced emphysema (4-6 months exposure) (Yoshida et al. *Nat Med* 16, 767-773 (2010), Mizumura et al. *The Journal of clinical investigation* 124, 3987-4003 (2014), Lam et al. *The Journal of clinical investigation* 123(12), 5212-5230 (2013) and CS-induced impairment of MCC (1 month exposure) (Mizumura et al. *The Journal of clinical investigation* 124, 3987-4003 (2014), Lam et al. *The Journal of clinical investigation* 123(12), 5212-5230 (2013)). MCC, characterized by the upward movement of mucus by ciliary motion, can be impaired by airway cell dysfunction, or infiltration of immune cells into the lung. Impaired MCC leads to excessive airway mucus, recurrent pulmonary infection and chronic bronchitis.

Figure 7:
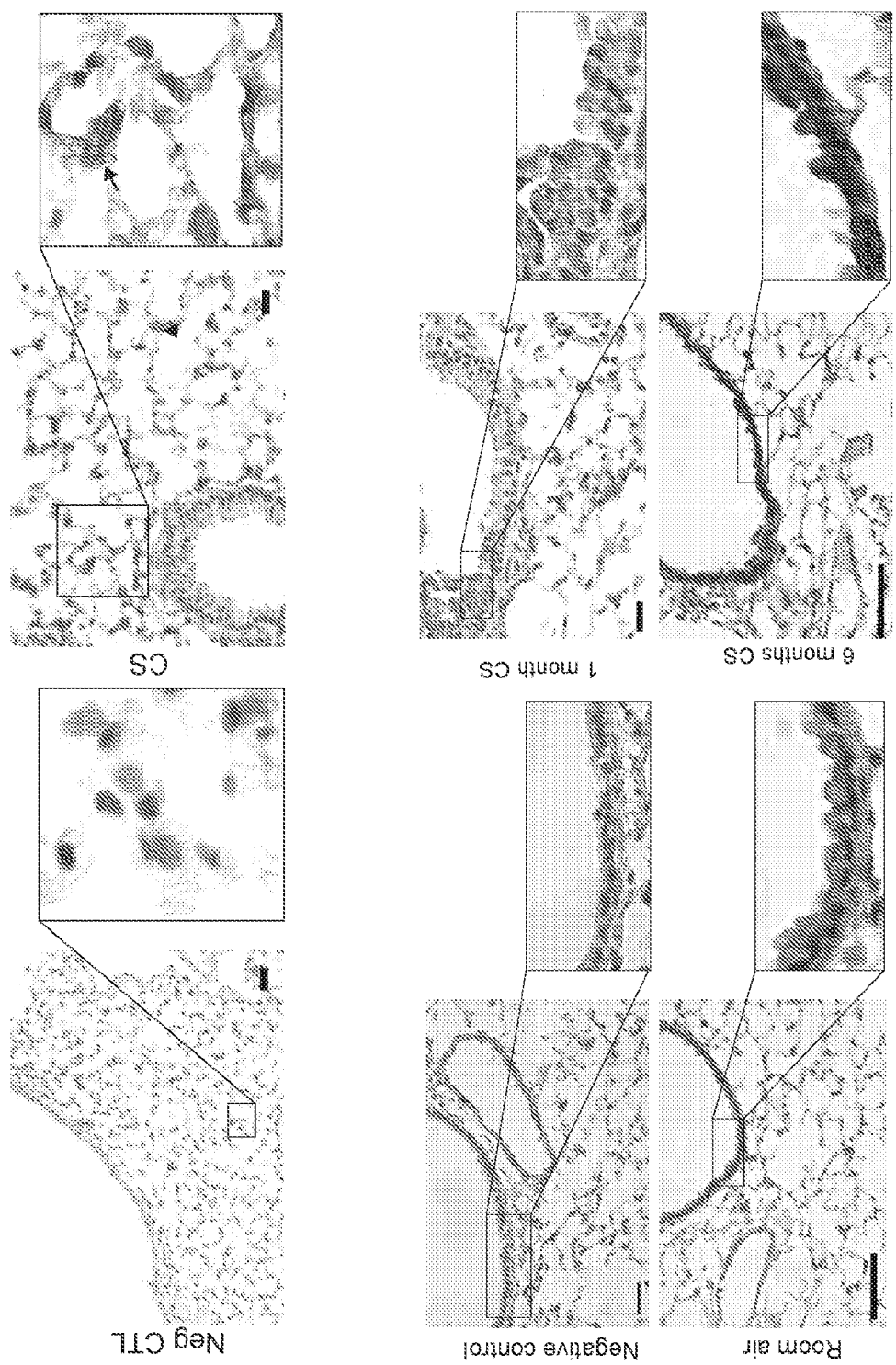
FIG. 7. IRP2 and experimental COPD. (a) Representative IRP2 immunostaining in the airways of mice exposed to RA or CS for 1 month or 6 months. (b) Co-staining of IRP2 (red), podoplanin (type I-cell), pro-SPC (type II-cell), acetylated alpha-tubulin (ciliated cell), uteroglobin (secretory cell), F4/80 (macrophage cell marker) or cytokeratin-5 (basal cell marker) or Pro3/Hoechst (nuclei) in mice exposed to RA or CS (6 months) (n=2 biological and n=2 technical replicates). Scale bar 50 μm or 10 μm (F4/80 only). (c-e) IRP2 immunoblot expression in (c) primary human bronchial epithelial cells and (d) in the human airway epithelial cell line Beas2B exposed to cigarette smoke extract (20%) for the indicated times (left) with confocal analysis of IRP2 staining in Beas2B cells treated with CSE (20%) for 30 minutes (right). Scale bar 10 μm. n=3 biological replicates. All data are representative of three independent experiments.
Figure 7:
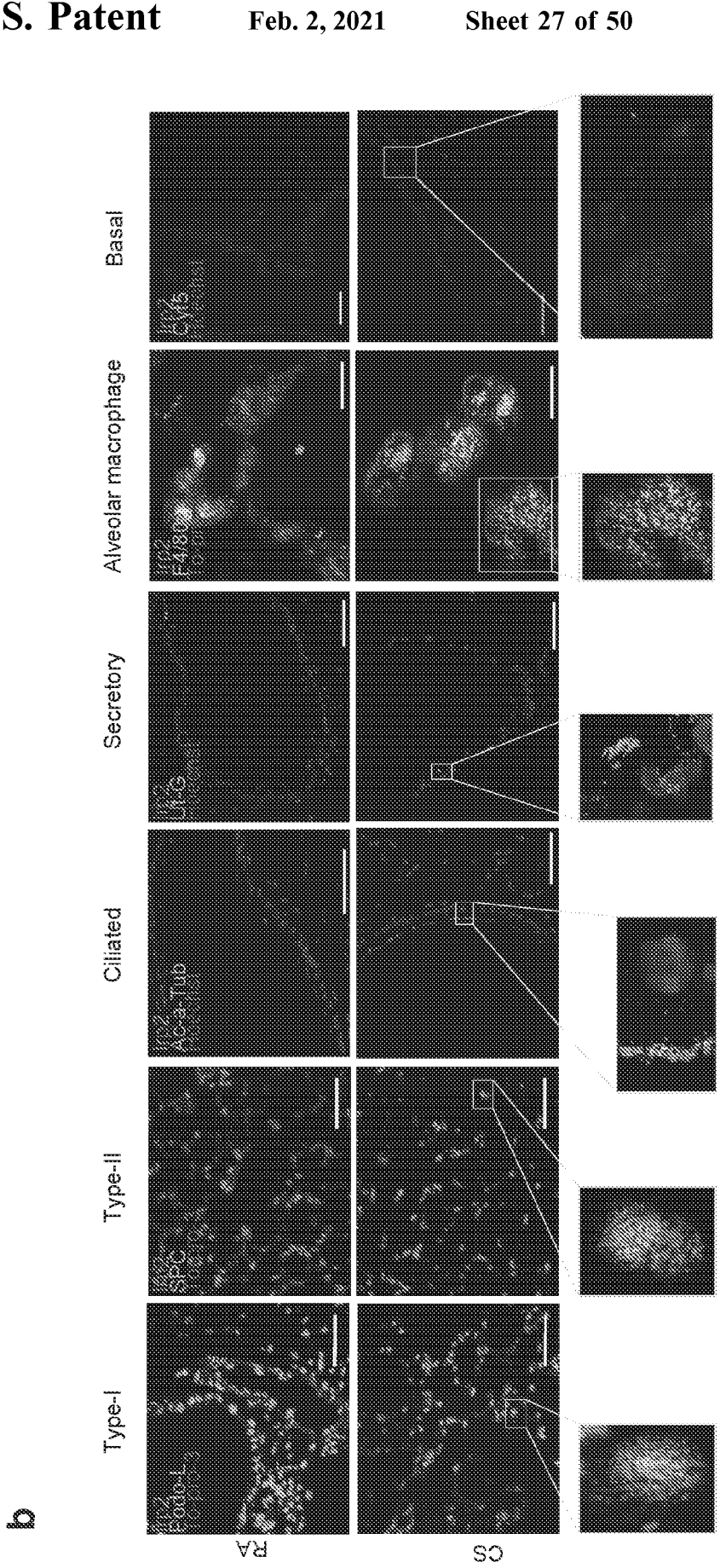
Figure 7:
Figure 7:
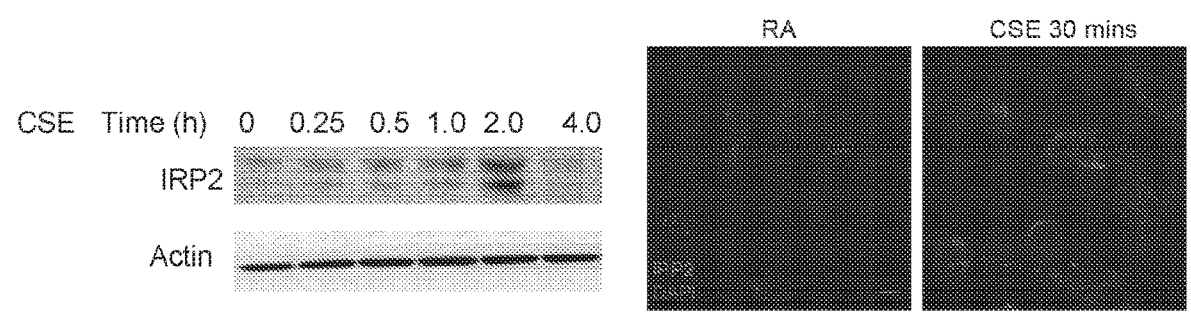

We observed higher IRP2 expression (with no change in IRP1 expression) and activity in the lungs of WT mice exposed to CS for 1-6 months when compared to room air (RA)-exposed controls (FIG. 1*a-c*). IRP2 expression localized in lung epithelial cells, including type I alveolar (podoplanin positive), type II alveolar (SPC positive), secretory airway (uteroglobin positive) and ciliated airway (acetylated alpha tubulin positive) cells (FIG. 1*d* and FIG. 7*a,b*). IRP2 expression also appeared to localize to the walls of intermediate size vessels with negligible staining in basal (cytokeratin 5 positive) epithelial cells (FIG. 7*b*). IRP2 expression was higher in type I, type II, secretory and ciliated epithelial cells as well as in infiltrating alveolar macrophages in response to CS (6 months), when compared to RA controls (FIG. 1*d* and FIG. 7*a,b*). We also observed higher IRP2 expression upon aqueous CSE (cigarette smoke extract) treatment (an in vitro model of CS exposure), in primary human bronchial airway epithelial cells and in the human bronchial airway epithelial cell line Beas2B, compared to RA exposed controls (FIG. 7*c,d*).

Figure 8:
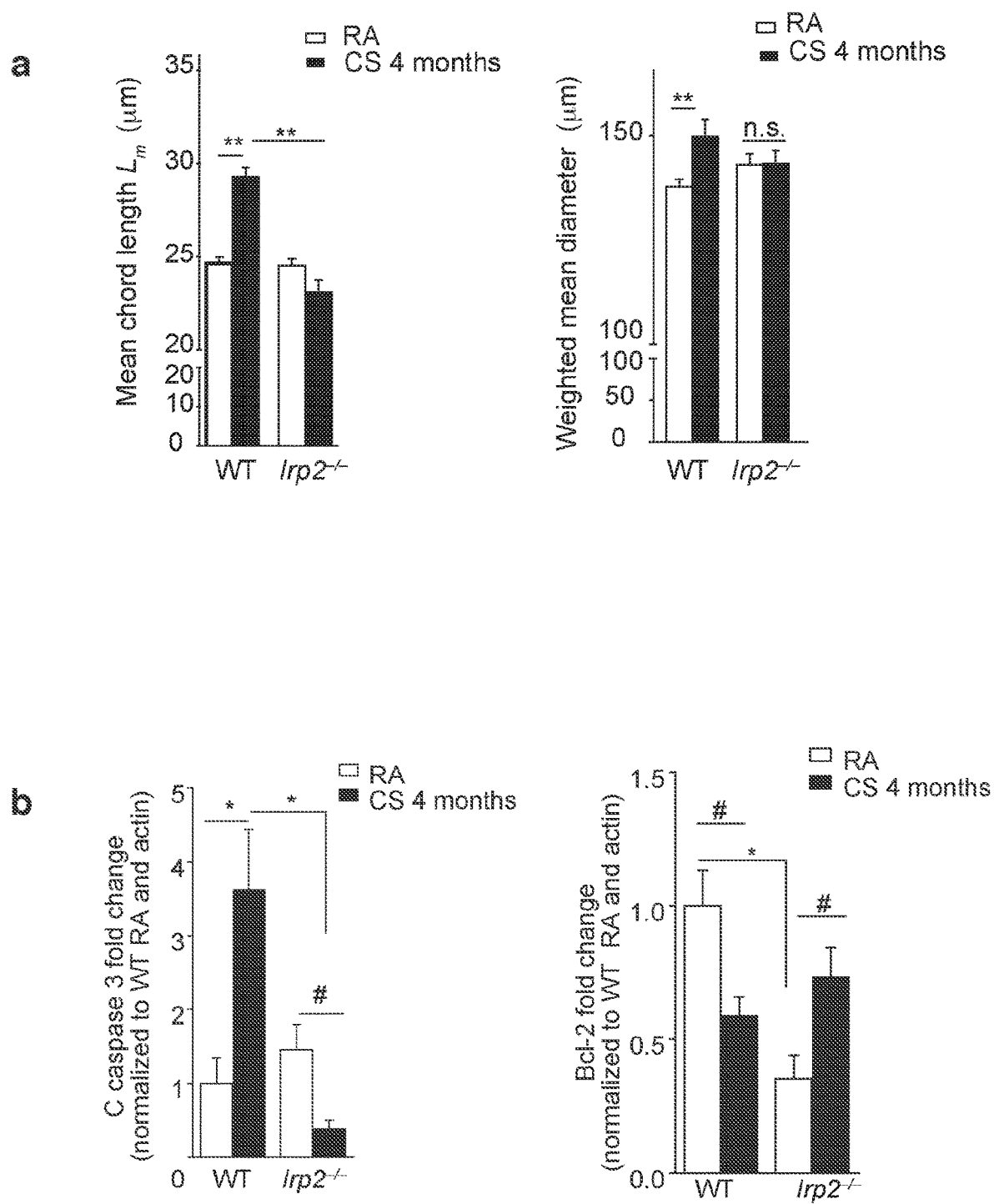
FIG. 8. Irp2$^{-/-}$ mice are protected from CS-induced emphysema independently of IRP1. (a) Mean chord lengths (left) and weighted mean diameters (right) of Irp2$^{+/+}$ (RA, n=5;CS, n=3) or Irp2$^{-/-}$ (RA n=6, CS n=6) C57/BL6 mice exposed to room air (RA) or cigarette smoke (CS) for 4 months (n=10 images per mouse). (b) Cleaved caspase-3 or Bcl 2 expression levels by immunoblot analysis (WTRA n=5; WTCS n=3; Irp2$^{-/-}$RA, CS n=6; n=2 technical replicates). (c) LC3B (left) and Atg 7 (middle) immunoblot expression and LC3B immunostaining (right) (representative images of n=2 technical and n=4 biological replicates per group) of WT and Irp2$^{-/-}$ murine lungs exposed to RA or CS (4 months). (d) IRP1 immunoblot (left) analysis with densitometry (right) in WT or Irp2$^{-/-}$ mice exposed to RA or CS for 4 months. (e) Total leukocyte counts, total alveolar macrophages, total lymphocytes, total PMN's and (f) total BAL protein in Irp2$^{+/+}$ mice exposed to CS (1 month), n=3 technical replicates. All data are mean±s.e.m. *P<0.05, **P<0.01 by Two-Way ANOVA followed by Bonferroni correction. #P<0.05 by unpaired Student's t-test. #P<0.05, ####P<0.01 by unpaired Student's t-test. n.s.;not-significant.
Figure 8:
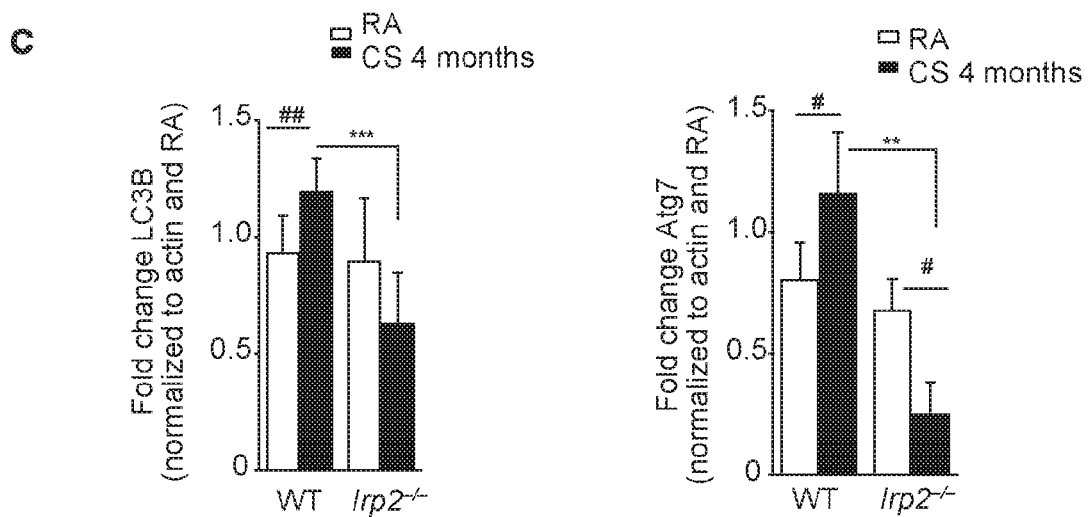
Figure 8:
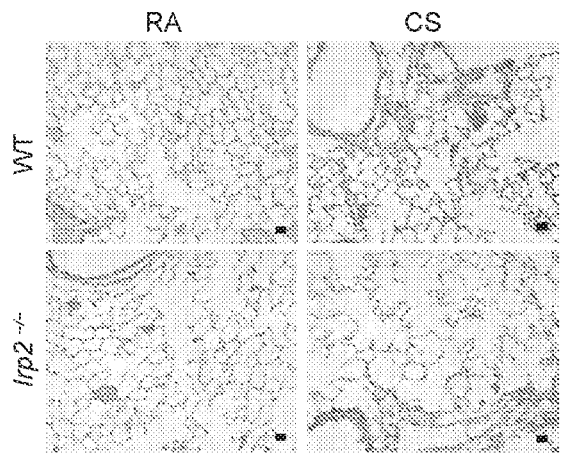
Figure 8:
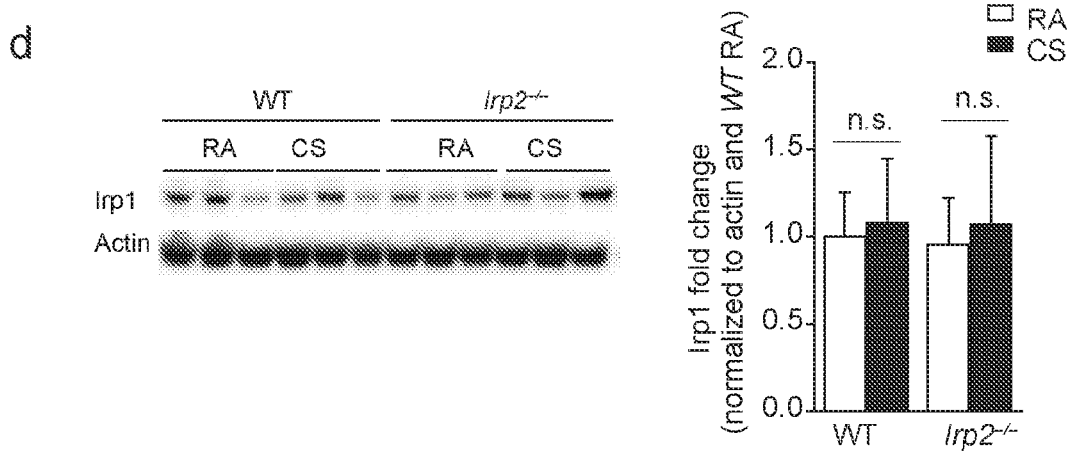
Figure 8:
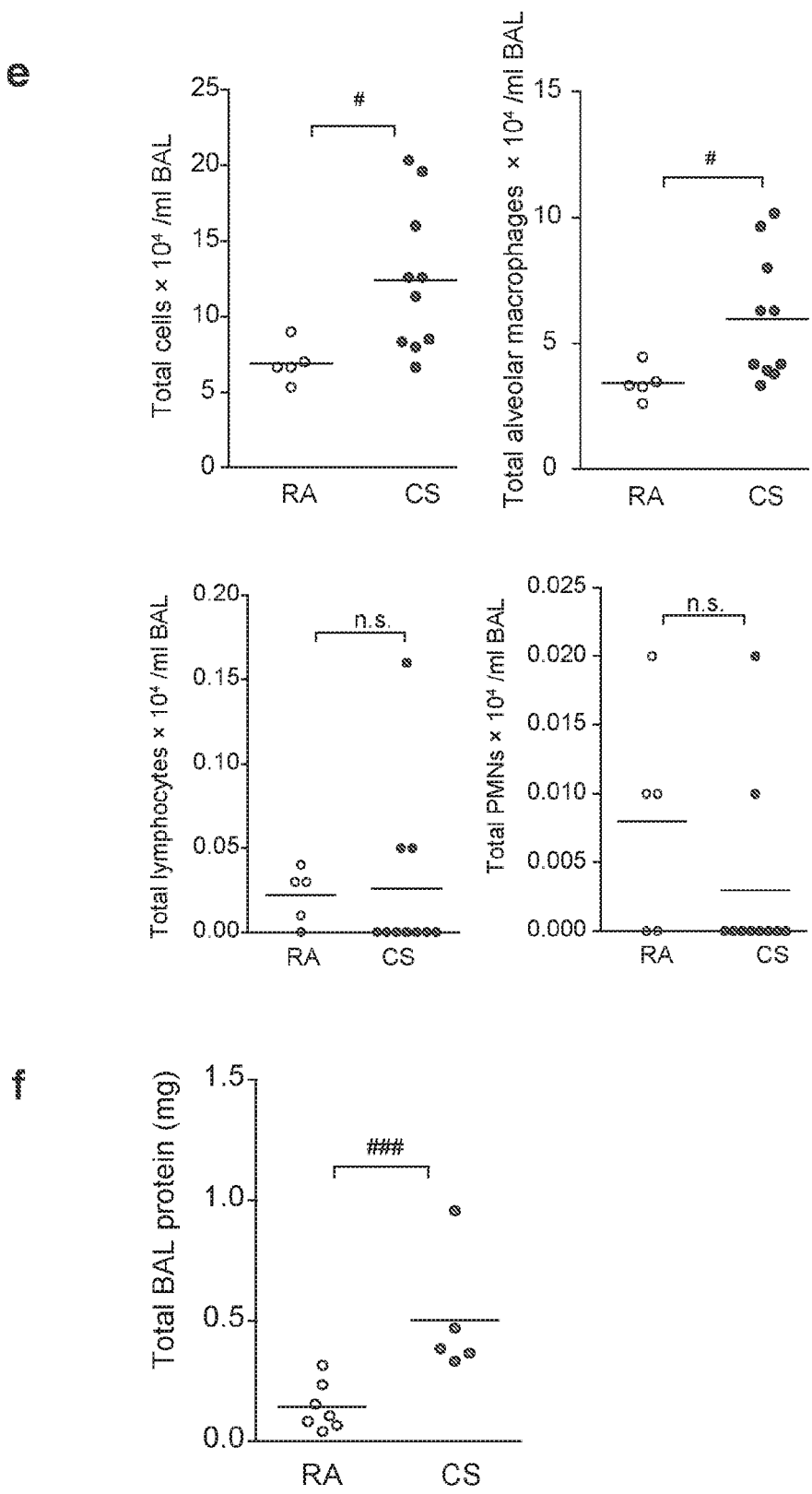
Figure 9:
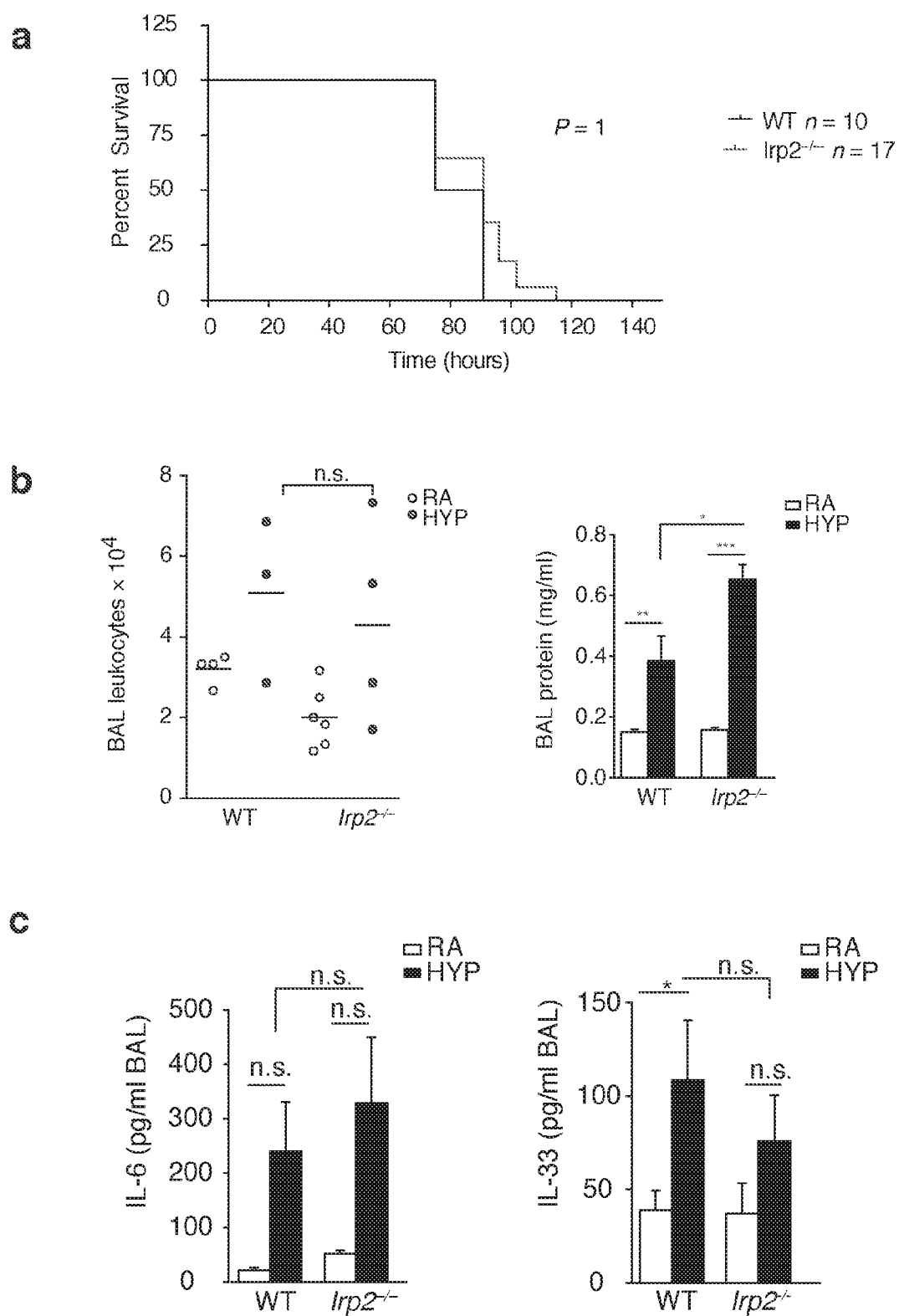
FIG. 9. IRP2 deficient mice and hyperoxia induced lung injury and CLP models. (a) Survival to hyperoxia (>99% O$_2$) over 0-120 hours in WT (n=10) and Irp2$^{-/-}$ (n=17) mice. (b) Total BAL leukocytes (left), total BAL protein (right), (c) BAL IL-6 (left ELISA) and BAL IL-33 (right ELISA) concentrations in WT (control n=4; hyperoxia n=5) and Irp2$^{-/-}$ mice (control n=5; hyperoxia n=4) exposed to hyperoxia for 70 hours. (d) CLP survival over 0-168 hours in Irp2$^{+/+}$ (n=7) and Irp2$^{-/-}$ (n=8). (e) Total BAL leukocytes (left), total BAL protein (right) levels, (f) BAL IL-6 (left ELISA) and BAL IL-33 (right ELISA) concentrations in WT and Irp2$^{-/-}$ mice 24 hours after CLP surgery. (g) Plasma IL-1β (left ELISA) and plasma IL-18 (right ELISA) levels WT (sham n=2;CLP n=4) and Irp2$^{-/-}$ mice (sham n=3;CLP n=4) 24 hours after CLP surgery. All data are mean±s.e.m. *P<0.05. P<0.01, *P<0.005 by one-way ANOVA.
Figure 9:
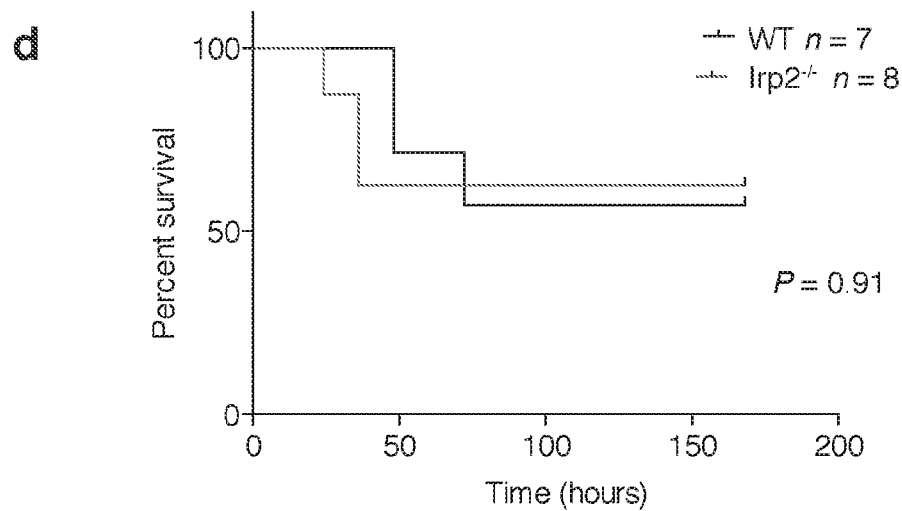
Figure 9:
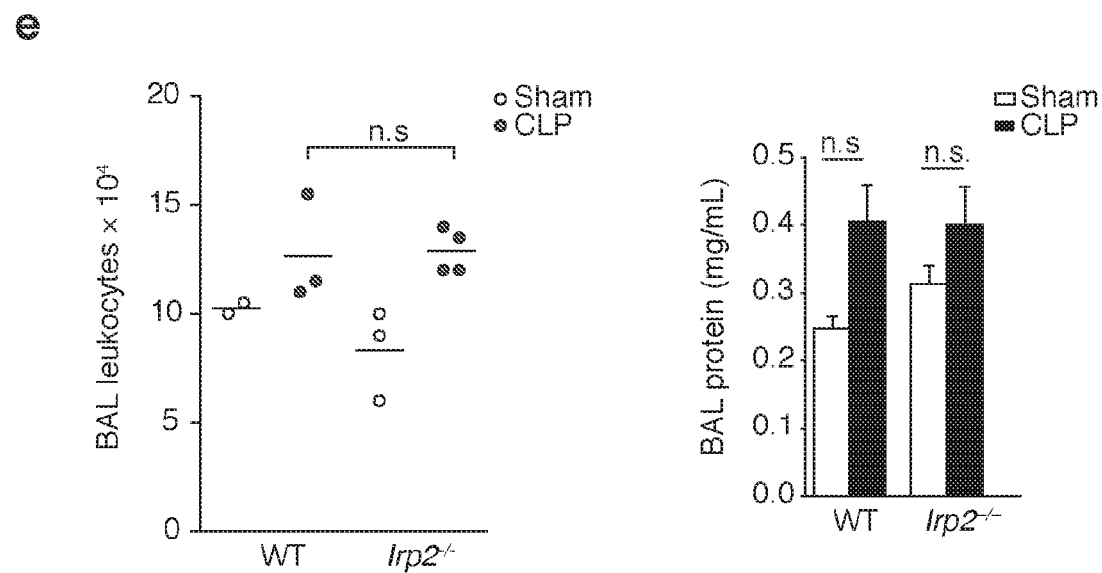
Figure 9:
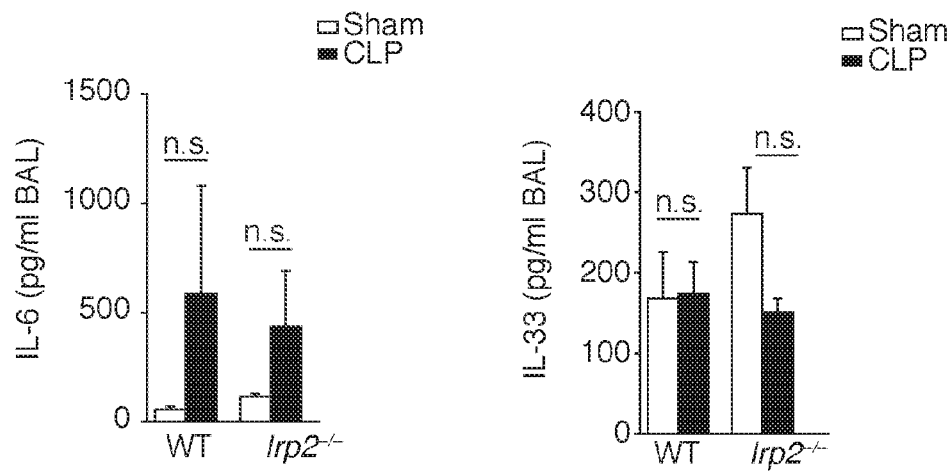
Figure 9:
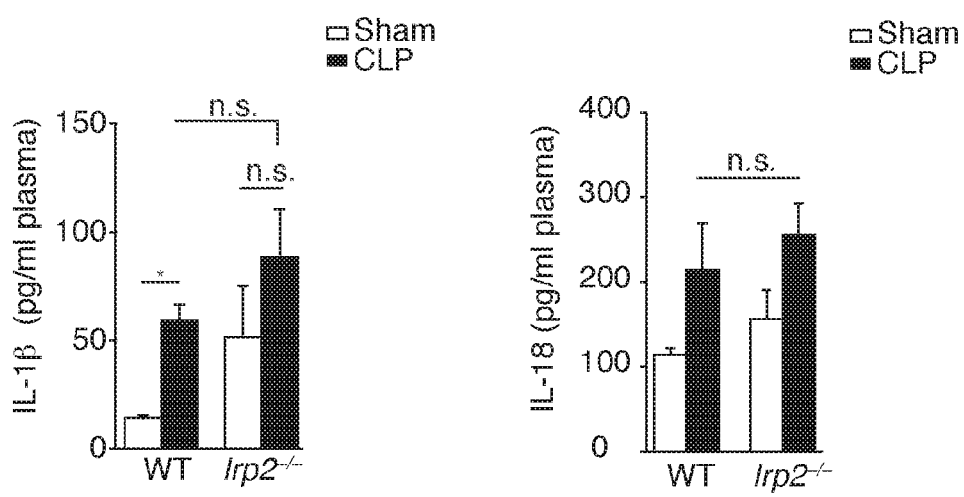

Overexpression of IRP2 has been associated with embryonic lethality in mice; we therefore used a loss of function approach to study the function of IRP2 in experimental COPD. WT mice exposed to CS for 4-6 months had higher mean chord lengths, air space diameters (FIG. 1*d* and FIG. 8*a*) and greater thickness of the small airways (all established indices of experimental COPD (Hogg et al. *N Engl J Med* 350, 2645-2653 (2004), Mizumura et al. *The Journal of clinical investigation* 124, 3987-4003 (2014)) when compared to air-exposed WT mice (FIG. 1*e*). Irp2$^{-/-}$ mice resisted CS-induced changes in mean chord length and air space diameter and were protected from small airway remodeling (FIG. 1*e,f* and FIG. 8*a*). Irp2$^{-/-}$ mice were also protected from CS-induced injury markers, previously shown to be associated with emphysema, including cleaved caspase-3 (increased apoptosis), matrix metalloproteinase 9 (MMP9) expression and the autophagy markers LC3B and Atg7 (FIG. 1*g* and FIG. 8*b,c*). IRP1 expression did not change in air- or CS-exposed Irp2$^{-/-}$ mice (FIG. 8*d*).

We developed an experimental model of CS-induced bronchitis by exposing mice acutely to CS (1 month) and measuring their mucociliary clearance (FIG. 1*h*). In this model, bronchoalveolar lavage fluid (BALF) from CS-exposed WT mice had greater leukocyte counts and had greater total BALF protein levels (an indicator of increased epithelial cell injury and permeability) when compared to air-exposed WT mice (FIG. 8*e,f*). CS-exposed mice also had higher BALF interleukin (IL)-33 protein concentrations (a pleiotropic cytokine predominantly expressed in lung tissue that induces airway inflammation in naive mice (Qiu, C., et al. *Immunology* 138, 76-82 (2013)) and higher BALF IL-6 protein concentrations (a cytokine associated with the severity of acute COPD exacerbations and decline in lung function (Hubeau et al., *Clinical science* (London, England: 1979) 125, 483-493 (2013)), when compared to air-exposed WT mice (FIG. 1*i*). Using this model, the mucociliary clearance of WT lungs exposed to CS was significantly lower compared with air-exposed controls (P<0.05) (FIG. 1*h*). Irp2$^{-/-}$ mice were protected from CS-impaired MCC and CS-exposed Irp2$^{-/-}$ mice exhibited less BALF IL-6 and IL-33 protein concentrations when compared to CS-exposed WT mice (FIG. 1*h,i*). IRP2 deficiency failed to protect against lung injury (greater BAL leukocytes, BALF protein and BAL IL-6 and IL-33 protein) and mortality in a mouse hyperoxia-induced acute lung injury model and in a mouse cecal ligation and puncture-induced polymicrobial sepsis model (FIG. 9*a-g*), highlighting the specificity of the functional role of IRP2 in CS-induced lung injury associated with COPD.

Identification of Novel Target Pathways of IRP2 in the Lung

Figure 10:
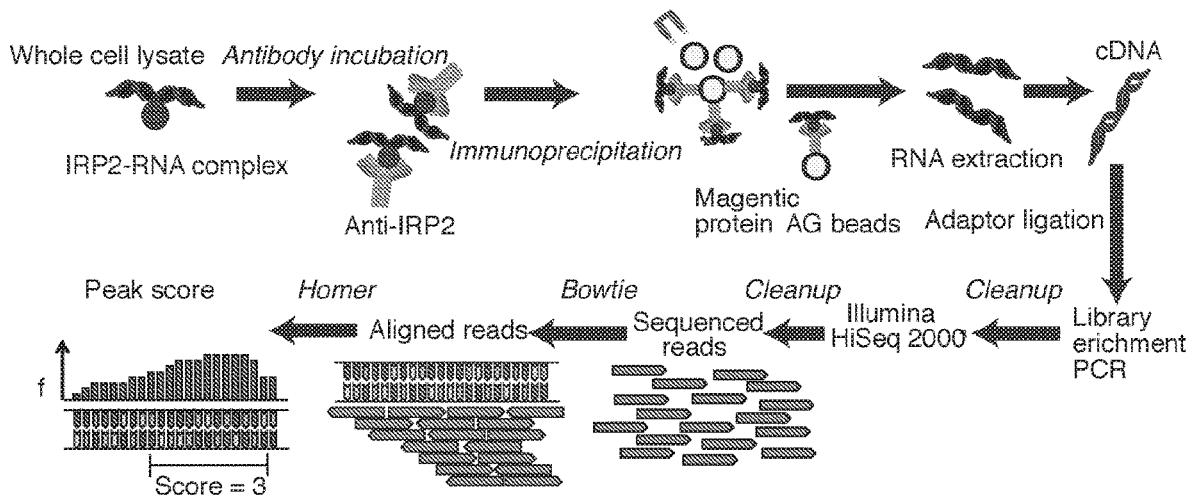
FIG. 10. RNA-immunoprecipitation of IRP2-RNA complexes from Beas2B cells treated with and without DFO. (a) Workflow of RIP-Seq. (b) Immunoblot of IRP2 immunoprecipitation with IgG, 2 μg or 5 μg IRP2 antibody in Beas2B cells. (c) Quality of RNA-Seq library generated. (d) To identify RIP-Seq peaks four primary comparisons were made: CTL compared to IgG-CTL (CTL/IgG), DFO compared to IgG-DFO (DFO/IgG), CTL compared to DFO (CTL/DFO) and DFO compared to CTL (DFO/CTL). (e) Enrichment of Peak scores of known IRP2 targets, ferritin (FTL) and transferrin receptor 1 (TfR) in the RIP-Seq data set and (f) validated by q-PCR. (g) A clustering of the annotations (black ticks) between the 4375 genes (x-axis) that had a RIP-Seq peak in any of the defined sets (CTL-specific, DFO-specific or Common) and the GO categories found to be enriched (FDR <10$^{-3}$) in these genes (y-axis) based on DAVID analysis. Five clusters, or "communities", of genes and enriched GO categories emerged (denoted by blue: community 1, yellow: community 2, turquoise: community 3, red: community 4 and green: community 5). This data was used to define each of the "community" segments of the Circos plot. All data are mean±s.e.m. *P<0.05, by Two-Way ANOVA followed by Bonferroni correction. #P<0.05, ###P<0.001 by unpaired Student's t-test. ND, not detected.
Figure 10:
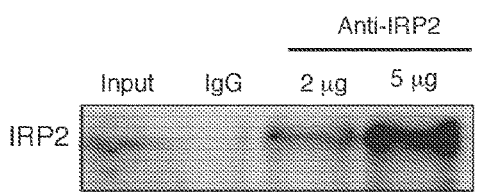
Figure 10:
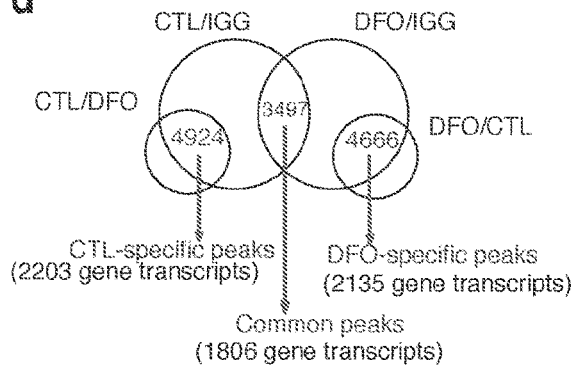
Figure 10:
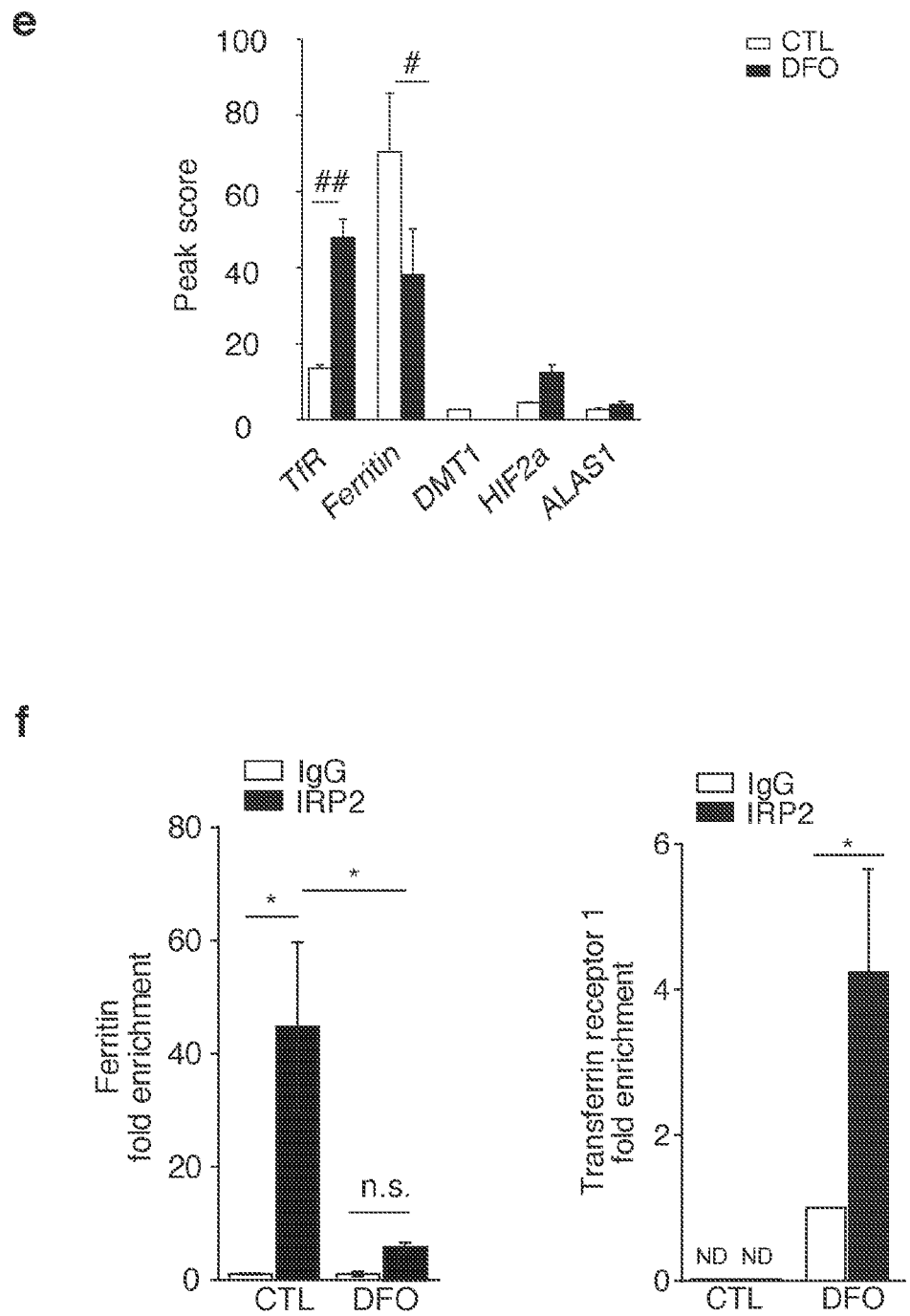
Figure 10:
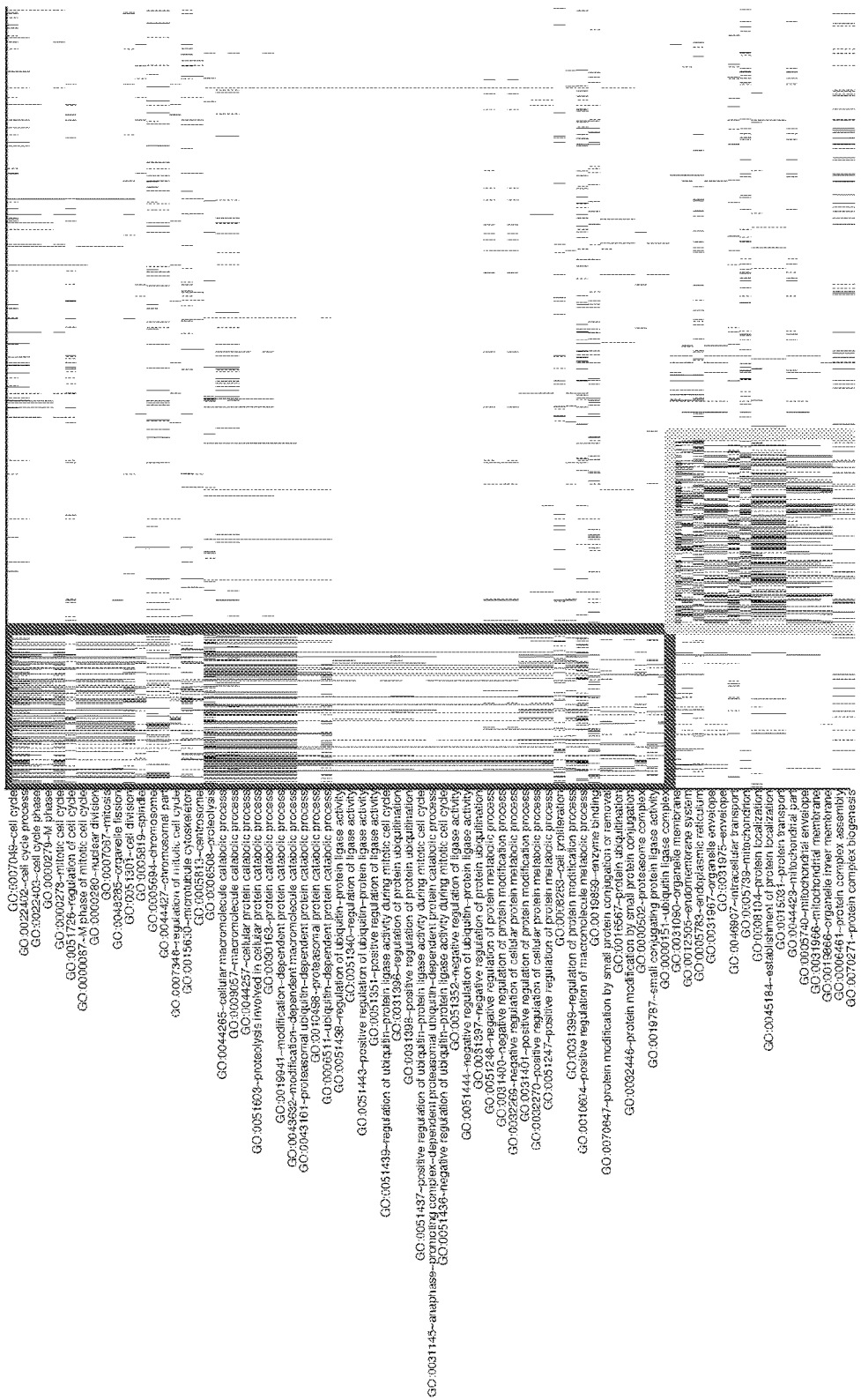
Figure 10:
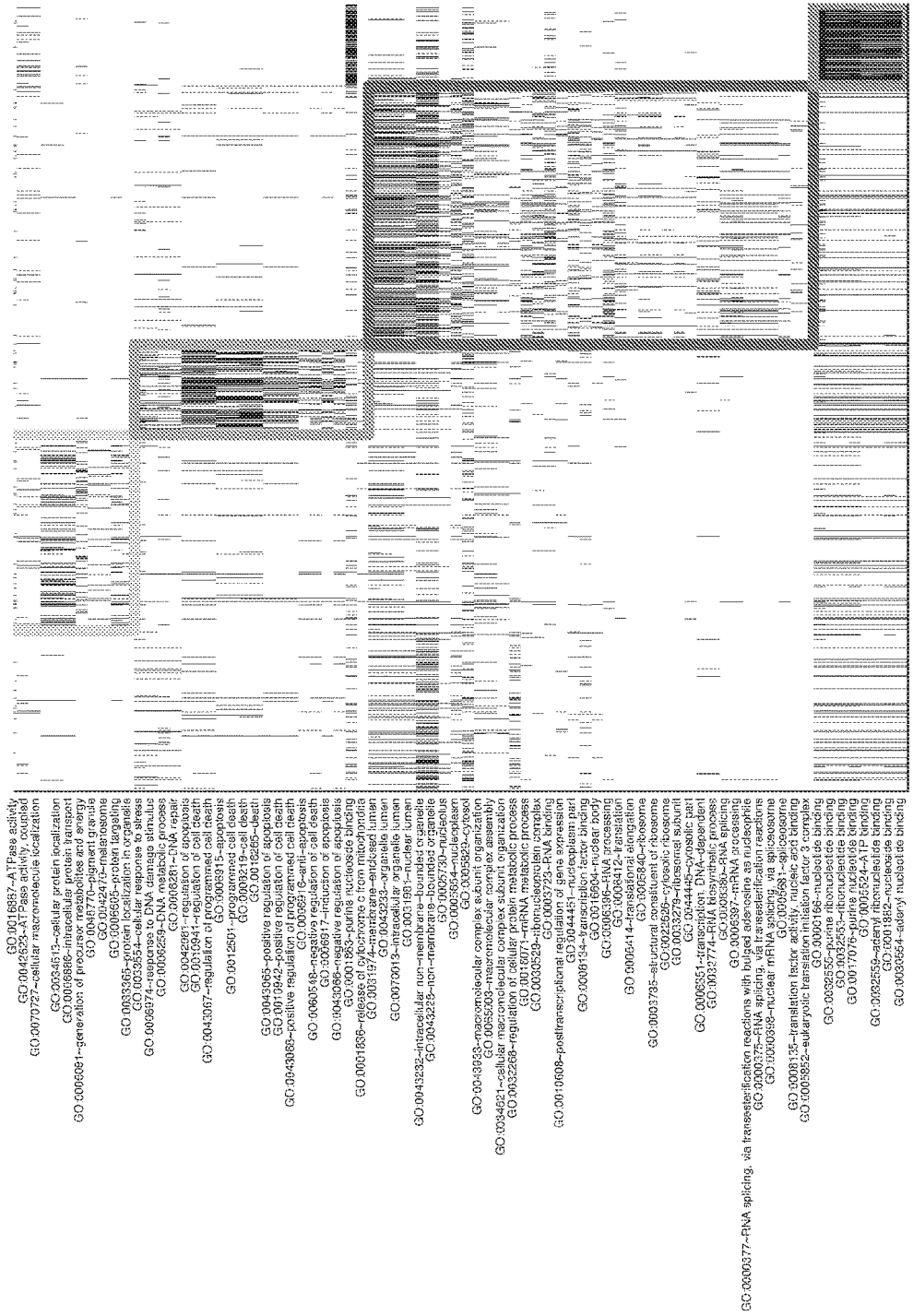

As described above, IRP2 conferred important functional impact in the pathogenesis of COPD in two experimental COPD models. We therefore sought to delineate the mechanism by which IRP2 promoted experimental COPD by first identifying the downstream targets of IRP2 in the lung. For unbiased identification of RNA targets of IRP2, we used the human airway epithelial cell line Beas2B stimulated with or without deferoxamine (DFO) (to stabilize IRP2 expression[27]), immunoprecipitated IRP2-RNA complexes and performed whole transcriptome sequencing (RIP-Seq) (FIG. 10*a-c*). This analysis identified 1806 IRP2-target genes, which included transcripts for known IRP2 targets, including ferritin and transferrin receptor (TfR) (confirmed by qPCR) (FIG. 10*d-f*), thus validating the model system.

Figure 2:
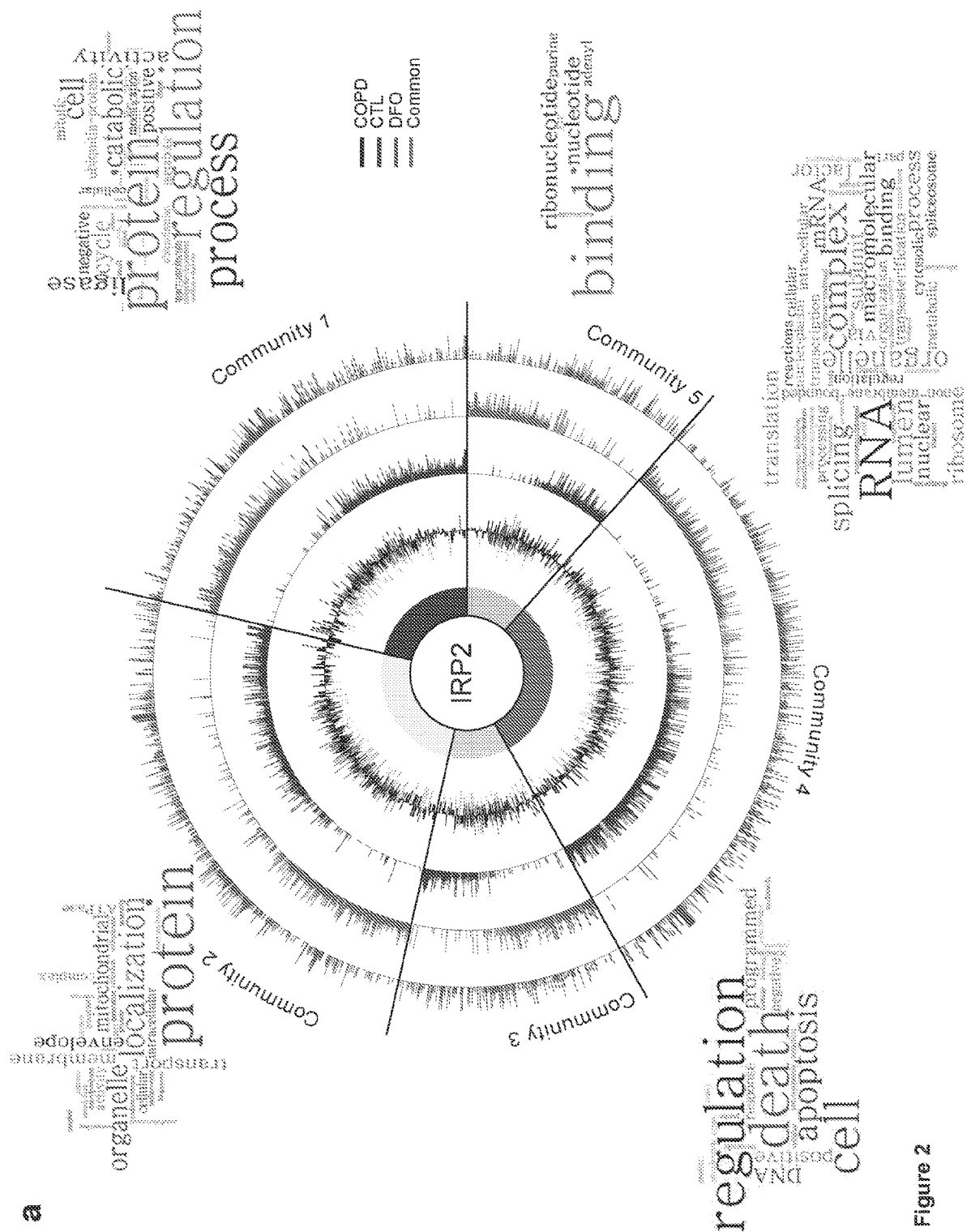
FIG. 2. Novel targets of IRP2 in the lung. (a) Circos plot of communities of genes and gene ontology (GO) terms to demonstrate the gene transcripts and pathways enriched and/or altered in the RIP-Seq data set. Control (CTL)-specific (blue), DFO-specific (red) and common (purple) peak data sets are represented by individual rings, with the height of bars corresponding to the peak score (n=2 biological replicates). Gene expression data (mRNA) data downloaded from the LGRC, which included controls and subjects with COPD (n=121 COPD subjects, n=20 non-smokers and n=18 smokers) represented on inner black ring. The height of these bars corresponds to the log2 fold-change (FC) in gene expression levels between subjects with COPD and controls. Green denotes lower expression in COPD and magenta denotes higher expression in COPD. Word Clouds representing GO terms in each community with the size of each word reflecting its frequency among the names of the pathways in the community. Community 1 shows enrichment for the cell cycle, metabolism of RNA, the proteasome and immune system; community 2 for metabolism, mitochondria and membrane trafficking; community 3 for DNA repair, apoptosis, the cell cycle and signal transduction; community 4 for metabolism of proteins, transcription and translation; community 5 for nucleotide/purine metabolism pathways (b) Functional enrichment clustering analysis workflow to evaluate collective differential expression of genes in "communities" of RIP-Seq and in $Irp2^{-/-}$ versus WT gene expression data. (c) Results of functional enrichment clustering analysis. ***P=1.08×10$^{-8}$ by a two-tailed unpaired t-test.
Figure 2:
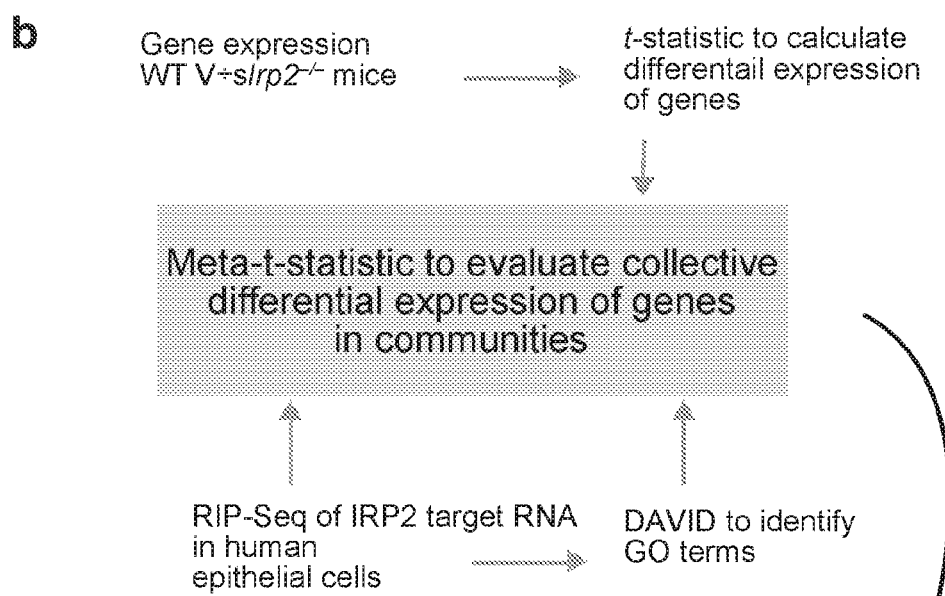
Figure 2:
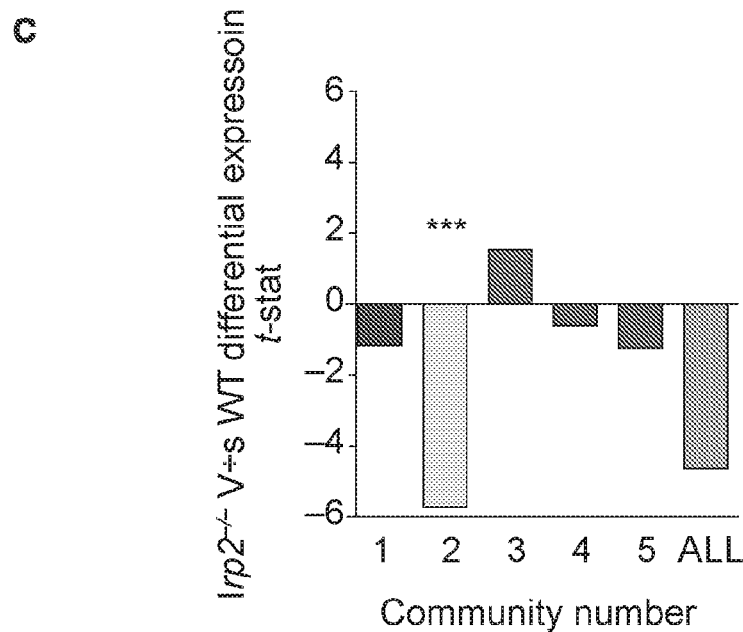

To better understand the biological meaning behind the IRP2-target genes, functional enrichment clustering analysis (See Methods and FIG. 10*g*) identified five core functional "communities" or pathways (depicted as word clouds), as demonstrated by the Circos plot in FIG. 2*a*. On this plot, the differential-expression of genes in lung tissue of individuals with COPD (Lung Genomics Research Consortium or LGRC) compared to controls (black ring) is also shown (FIG. 2*a*). We observed that many of the genes in each of the five communities had altered expression in COPD subjects and were known to be involved in the progression or pathogenesis of COPD.

To associate this human data to the heterogeneous in vivo environment of the lung in the absence of IRP2, we evaluated each of the five RIP-Seq communities for differential-expression patterns using a microarray study of lungs from WT and Irp2$^{-/-}$ mice (FIG. 2b). This analysis identified one community, Community 2, as having the most significant differential expression between the Irp2$^{-/-}$ and WT mice (FIG. 2c) (P<1.08–10$^{-8}$). In Community 2, the main pathway (from Gene Ontology terms, see FIG. 3a and FIG. 11) that emerged was related to mitochondrial function, with identified differentially expressed genes presented in FIG. 3a.

Figure 3:
FIG. 3. Irp2$^{-/-}$ mice resist CS-induced mitochondrial dysfunction. (a) Community 2 genes that annotated to 'mitochondria' GO categories. Red text indicates mitochondrial OXPHOS genes. (b-c) Differential-expression of genes from (a) in the human COPD cohorts (b) LGRC (n=121 COPD, n=18 smokers and n=20 non-smokers) and (c) ECLIPSE (n=136 COPD, n=84 smokers, n=6 non-smokers) related to low or high IRP2 expression. (d) Representative TEM images (left) and quantification (right) of WT or Irp2$^{-/-}$ mouse airways exposed to RA or CS (4 months)(15 EM fields, n=1 per group). Scale bar: 500 nm. Arrows indicate 'abnormal' mitochondria with damaged cristae. n; nuclei; m; mitochondria. (e) Representative cytochrome c immunostaining of WT and Irp2$^{-/-}$ mouse lungs exposed to RA or CS (6 months), n=2 technical replicates. Arrows indicate staining. Scale bar: 50 μm. (f) Percentage JC1 uptake in mitochondrial-enriched fractions of WT or Irp2$^{-/-}$ mouse lungs exposed to RA or CS (4 months), n=3 technical replicates. (g) Representative TMRE staining (bottom) (n=2 technical replicates) with fold change mean fluorescent intensity (top) of TMRE in WT and Irp2$^{-/-}$ primary lung epithelial cells treated with 20% CSE (4 hours) or FCCP (30 minutes). (h) OCR (left) and ECAR (right) normalized to Hoechst of WT and Irp2$^{-/-}$ primary lung epithelial cells treated with 20% CSE (4 hours), n=12 technical replicates. (i) Schematic of the role of IRP2 in mitochondrial responses to CS. All data are mean±s.e.m.: $^{\#}$P<0.05, $^{\#\#}$P<0.01 by student's unpaired t-test. *P<0.05, **P<0.01 by one-way ANOVA with Bonferroni correction.
Figure 3:
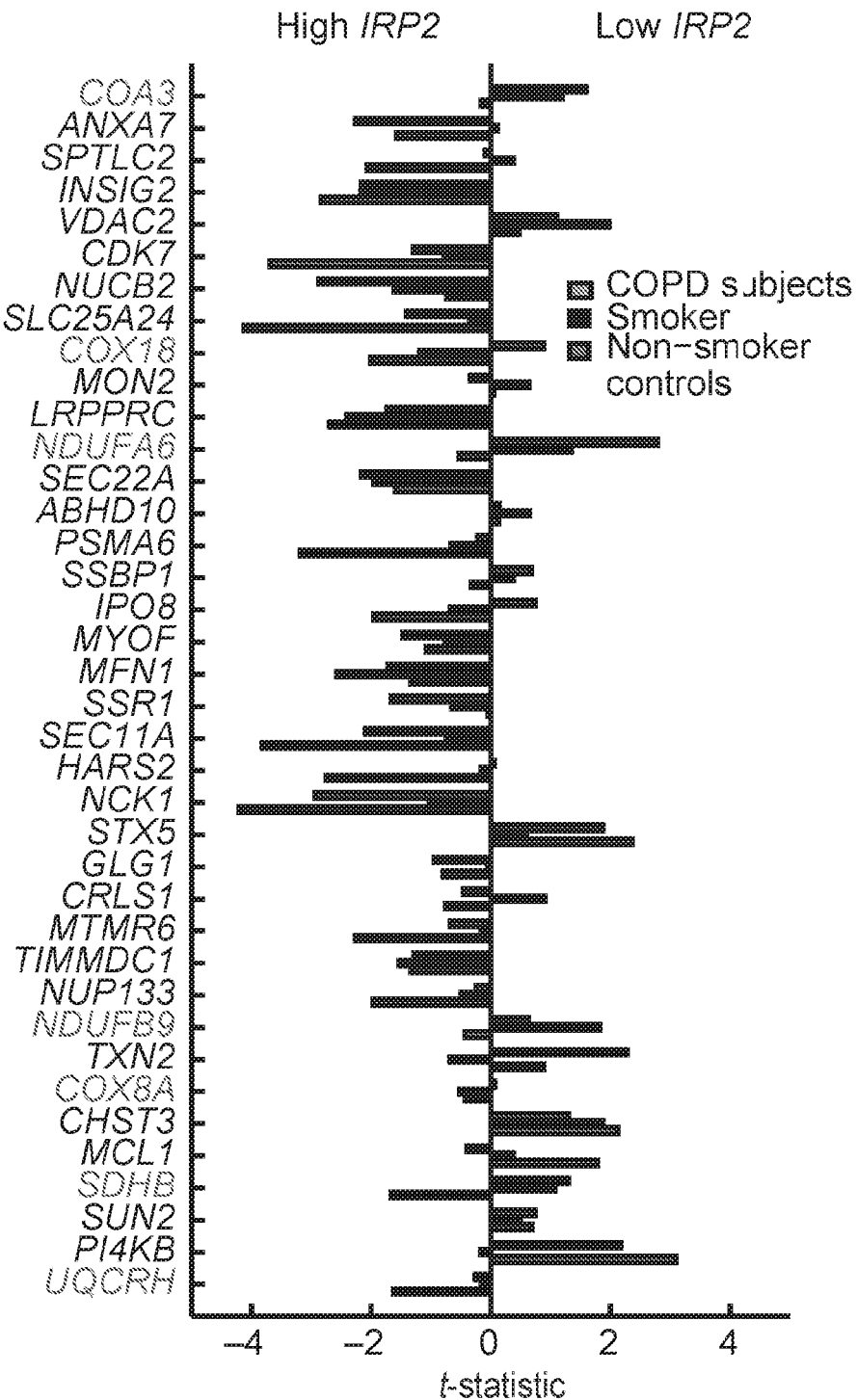
Figure 3:
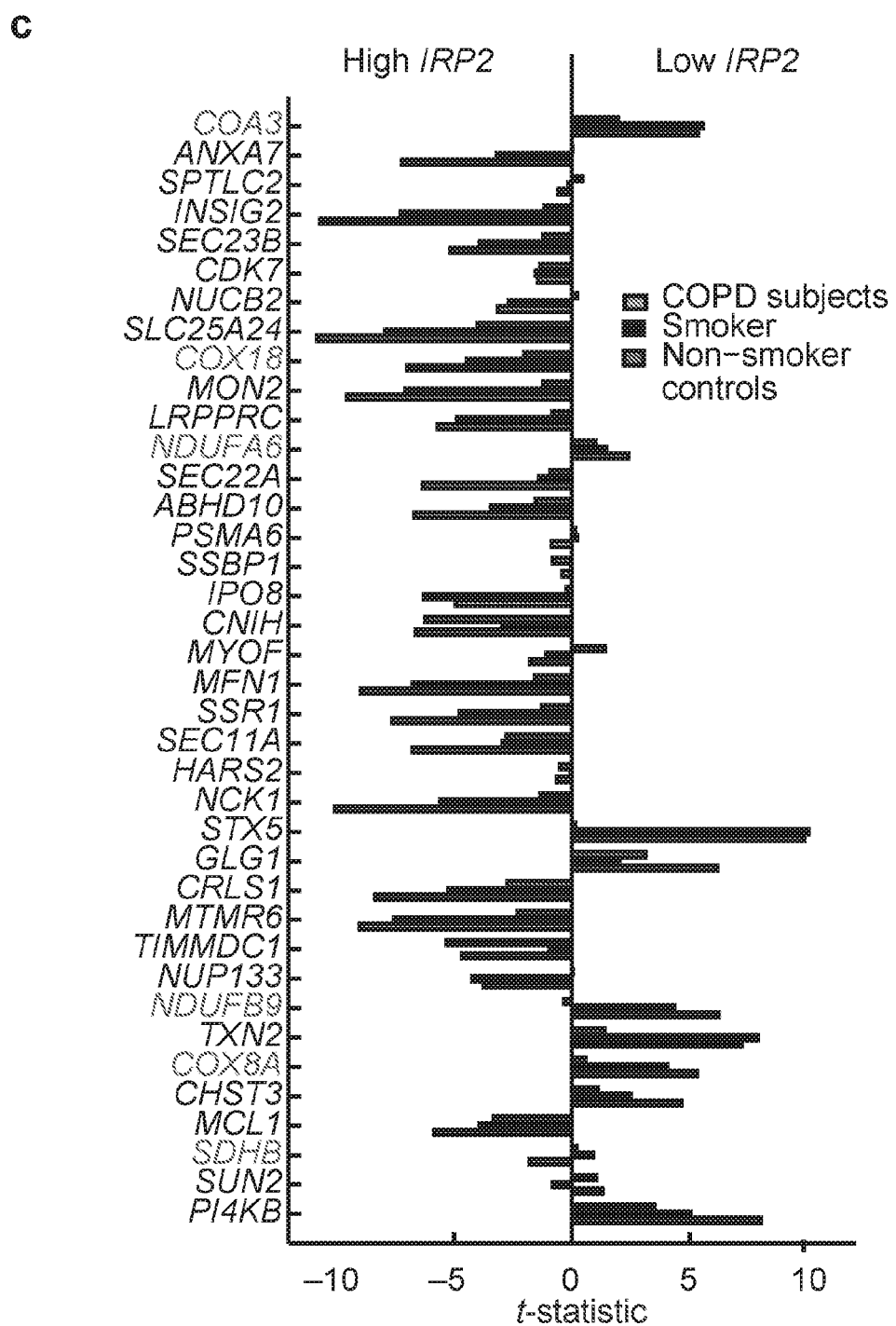
Figure 3:
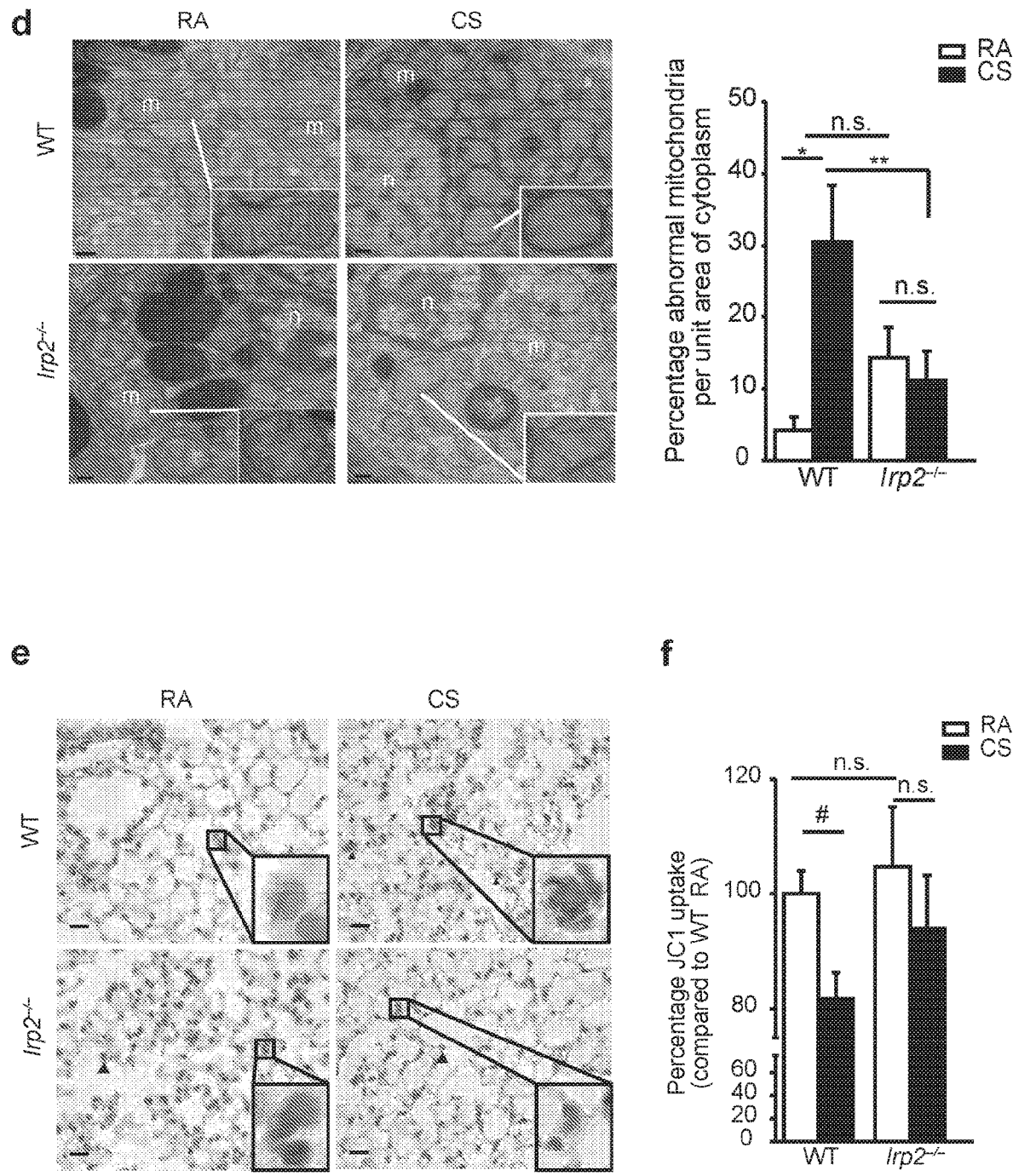
Figure 3:
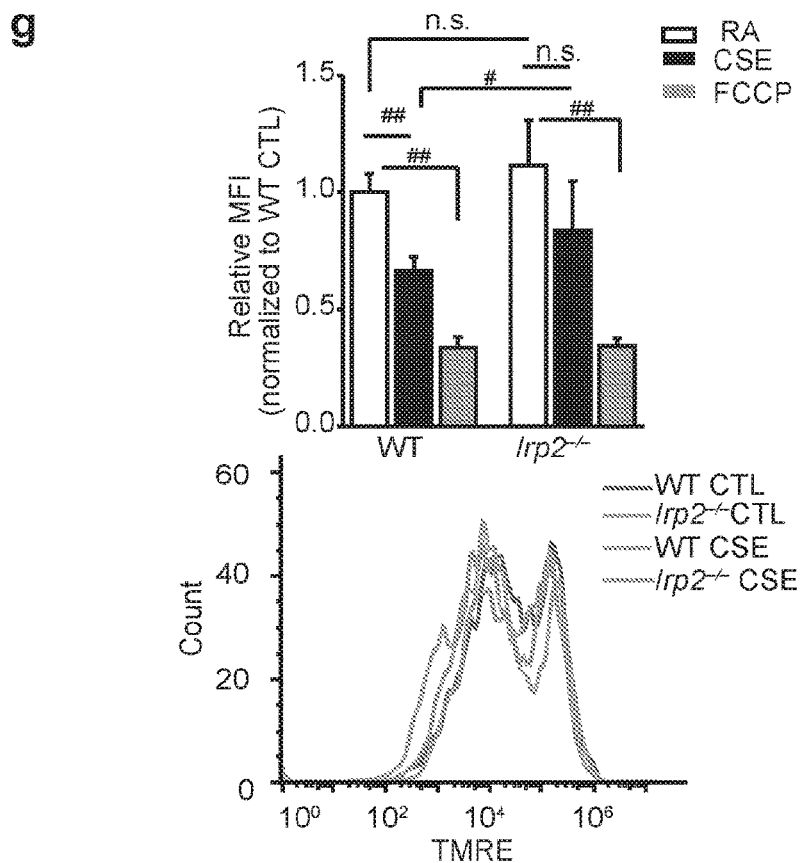
Figure 3:
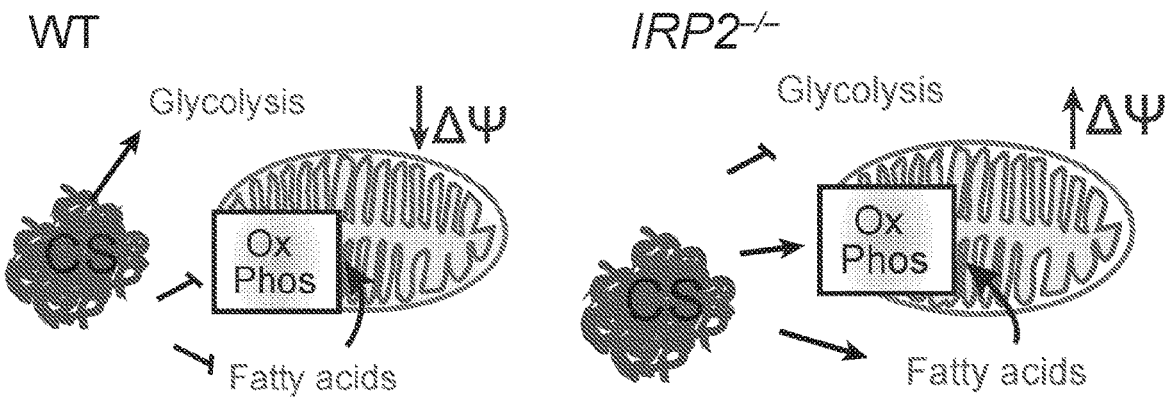
Figure 3:
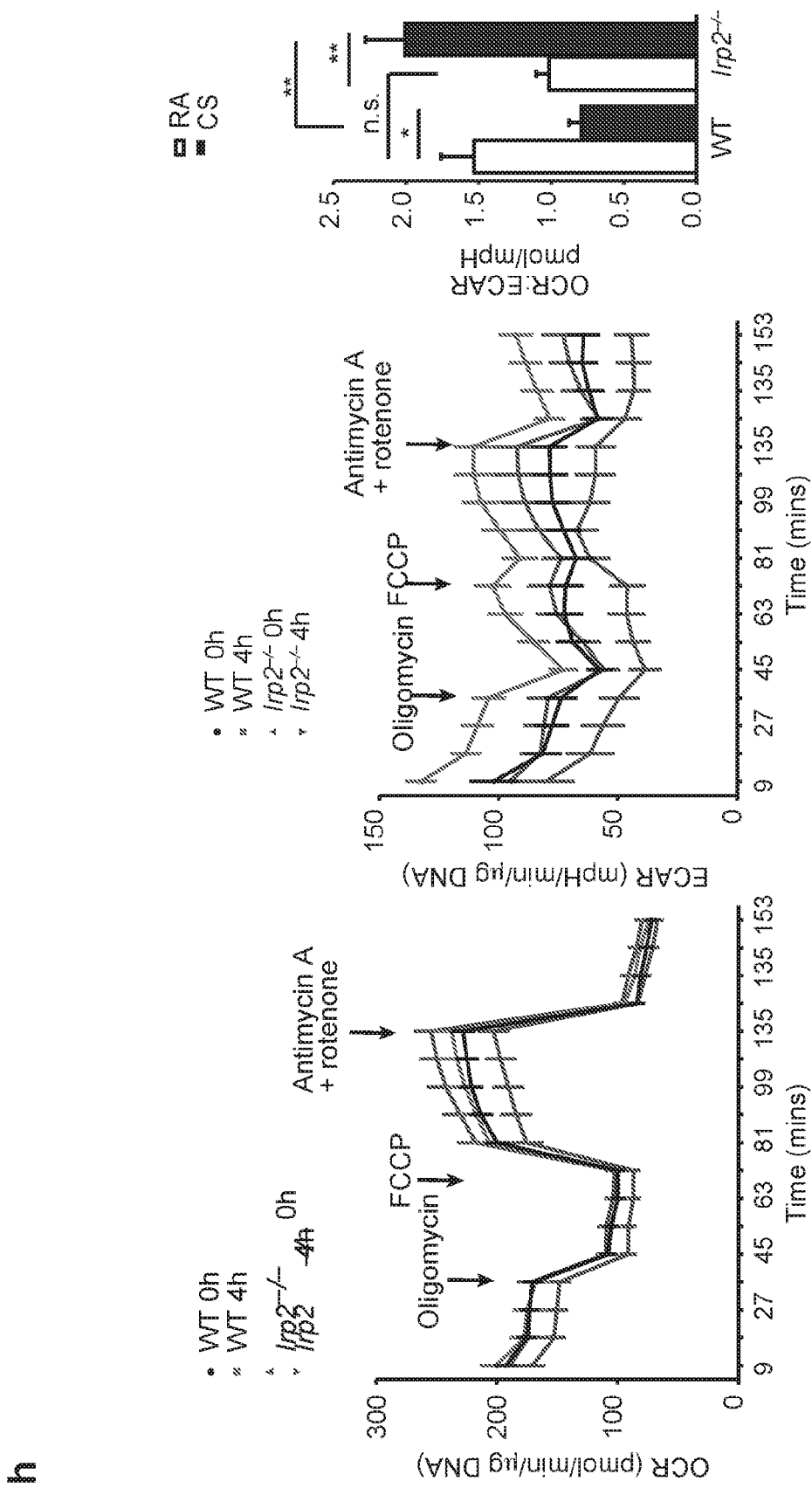
Figure 12:
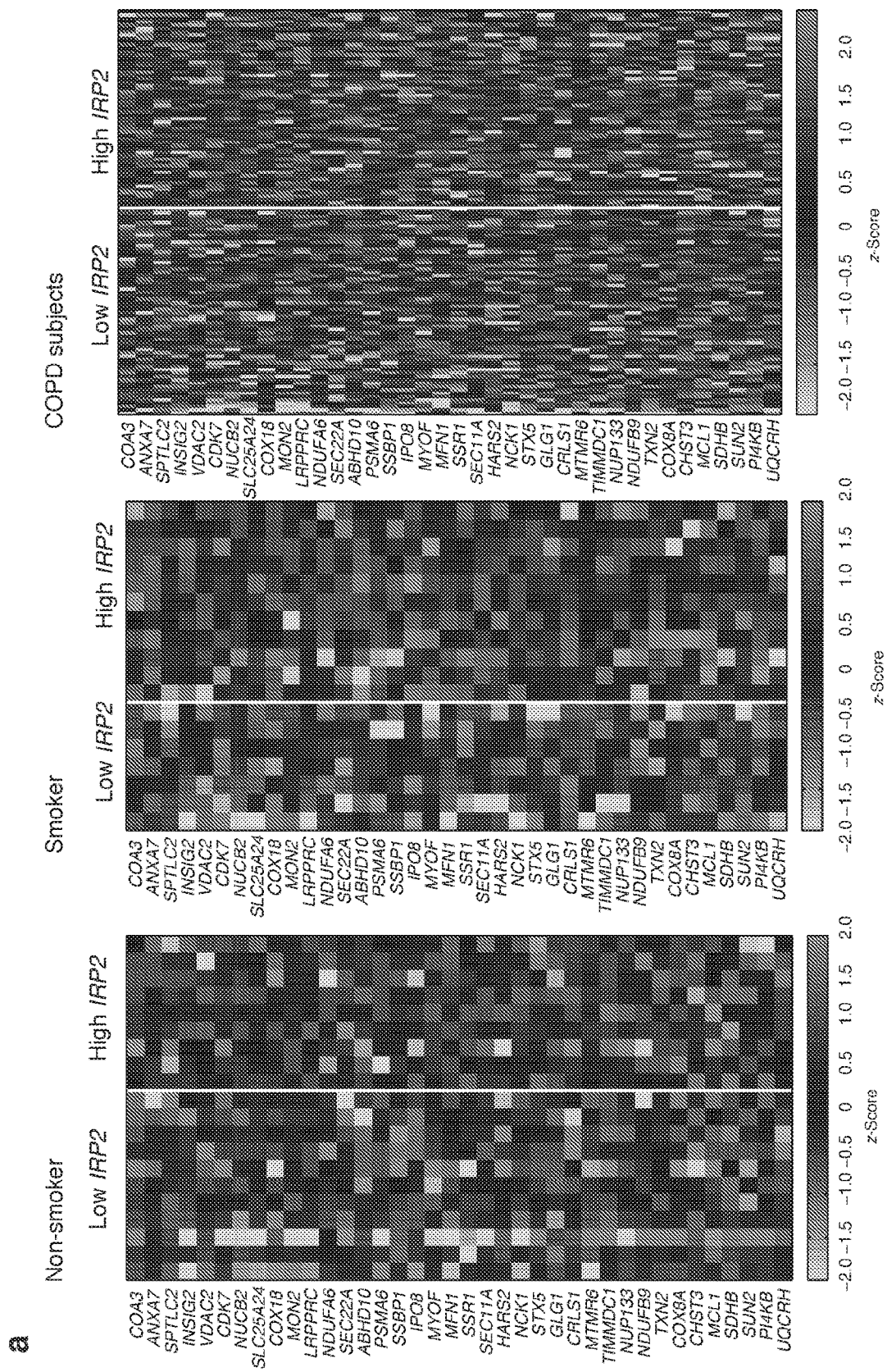
FIG. 12. Expression of mitochondrial genes in the (a) LGRC and (b) ECLIPSE COPD cohorts. Expression data was downloaded (FPKM values) from LGRC (GSE47460); selected mitochondrial genes (FIG. 3a) were measured in patients with high or low IRP2 expression. In each heat map, the subjects are ordered (from left to right) based on increasing values of IRP2 gene expression, with a white bar delimiting which individuals were identified as having "low" IRP2 expression (less than the median across all subjects) or "high" IRP2 expression (greater than the median across all subjects). Rows are ordered the same as FIG. 3a and each row is z-score normalized for visualization purposes. LGRC; n=121 COPD patients, n=20 non-smokers and n=18 smokers. ECLIPSE; n=136 COPD subjects, n =84 smoker controls, n=6 non-smoker controls. The overall "meta" P-values (for the genes in the heat map) were: COPD-subjects: 1.4e-3, Smoker-controls: 0.9564, Non-smoker controls: 0.5303.
Figure 12:
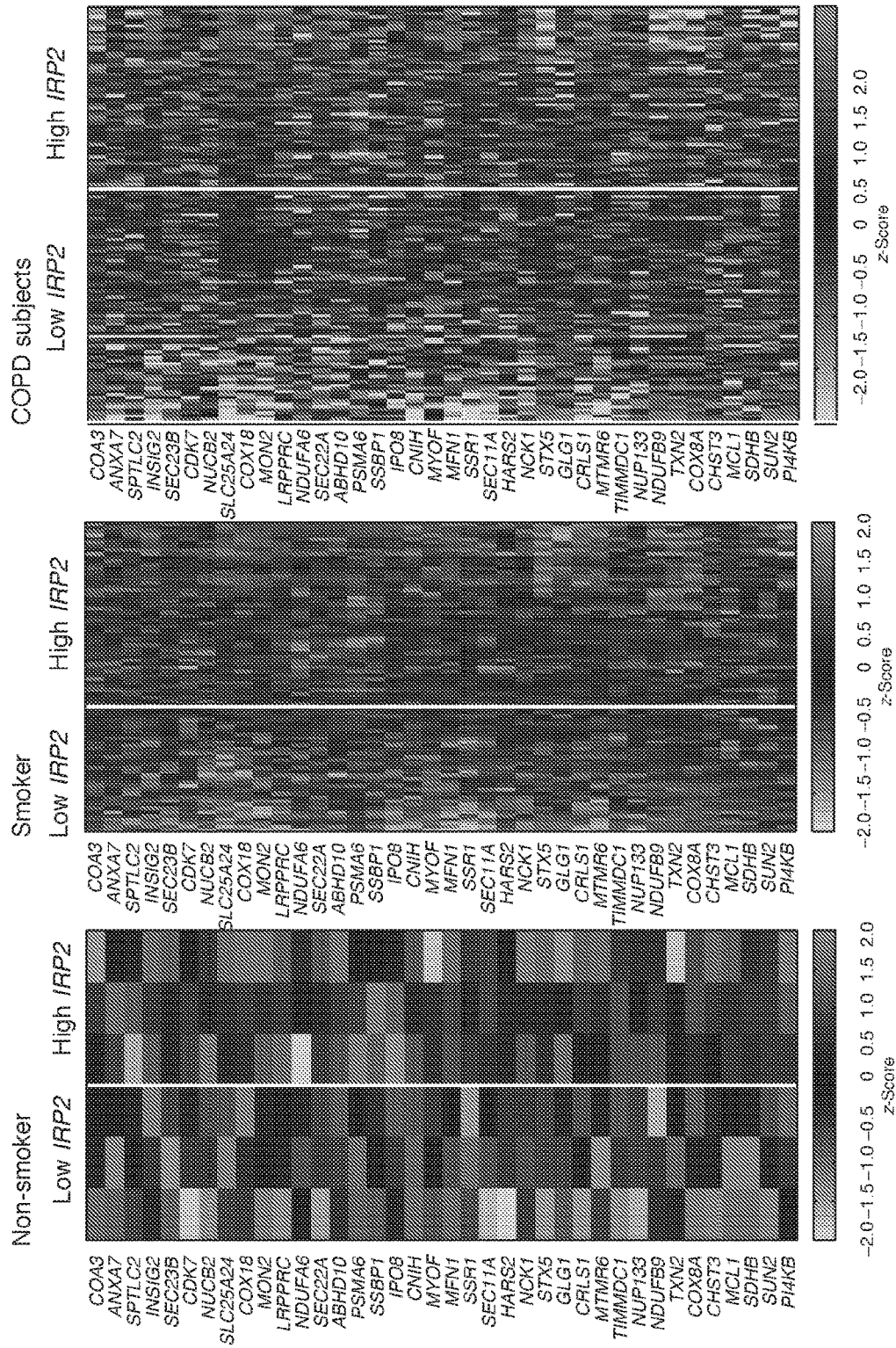

To assess the relationship between the differentially expressed mitochondrial genes in FIG. 3a to IRP2 expression in human subject with COPD, we evaluated the expression pattern of these genes in individuals (COPD and controls) with high or low IRP2 expression, using two human COPD cohorts, namely the LGRC (gene expression in lung tissue) and ECLIPSE (Evaluation of COPD Longitudinally to Identify Predictive Surrogate End-points) (gene expression in blood) cohorts. A strong association between the differential-expression of mitochondrial genes and differences in IRP2 expression was observed, with an overall stronger association observed in COPD subjects (FIG. 3b,c and FIG. 12).

Irp2$^{-/-}$ Mice Resisted CS-Induced Mitochondrial Dysfunction

Figure 13:
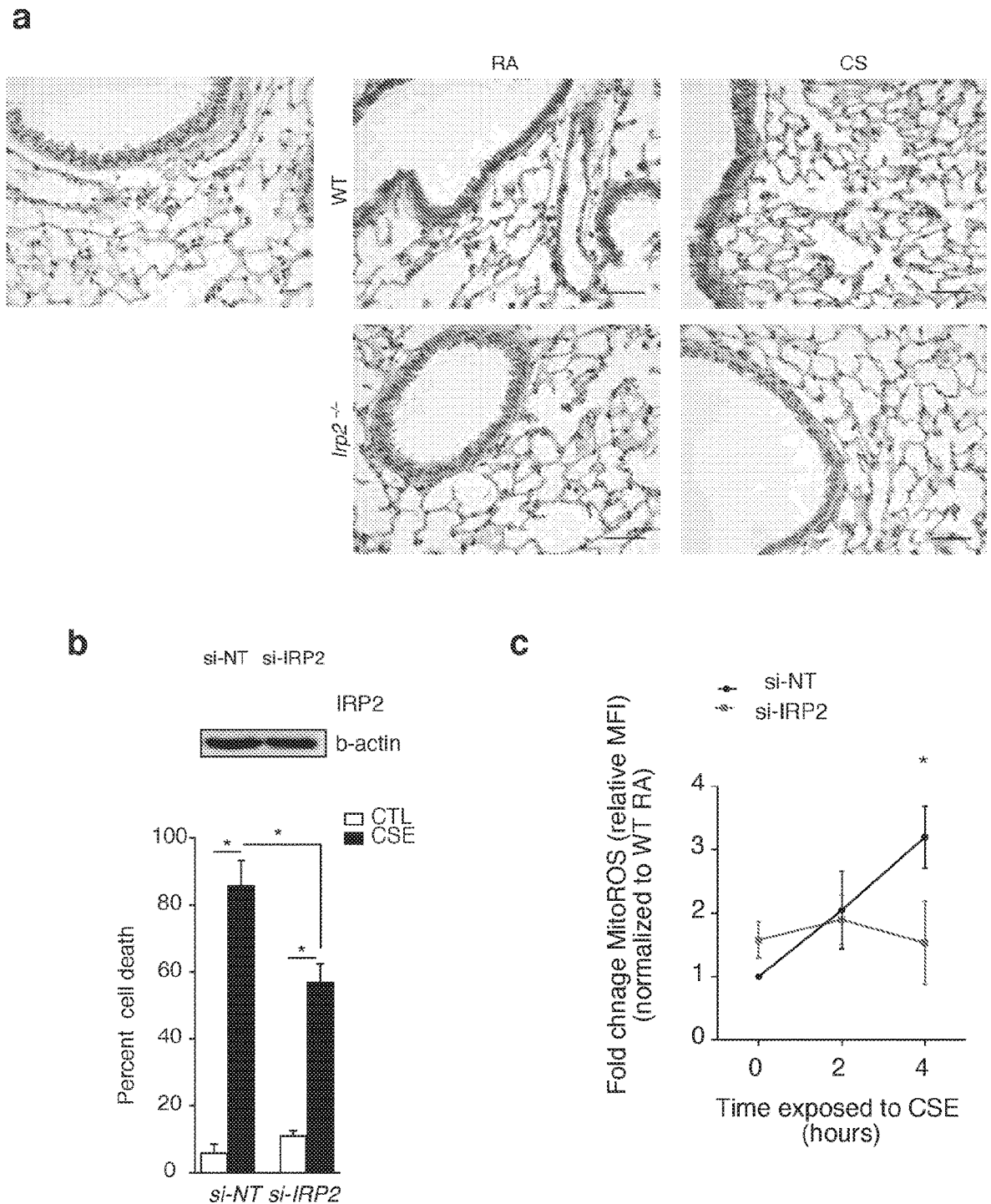
FIG. 13. Representative cytochrome c immunostaining of WT and Irp2$^{-/-}$ murine airways exposed to RA or CS (6 months), n=2 technical replicates (a). Scale bar: 100 μm. Human airway epithelial cells (Beas2B) treated with siRNA to IRP2 are protected from CS-induced cell death and mitochondrial reactive oxygen species (mROS) production. n=2 technical duplicates of n=3 biological replicates (b). Flow cytometry analysis of mROS production using Mito-SOX in CSE-treated Beas-2B cells with non-target (NT) siRNA or siIRP 2 siRNA (c). Data was normalized to Beas2B cells transfected with control non-target (NT) siRNA. n=2 technical duplicates of n=3 biological replicates. All data are mean±s.e.m. of three independent experiments *P<0.05, by Two-Way ANOVA followed by Bonferroni correction.

Based on the functional pathways highlighted in the RIP-Seq and differential-expression analysis observed in mice and humans, the functional role of IRP2 in mitochondrial responses to CS in experimental COPD was assessed. Lung epithelial cells from WT mice exposed to CS had abnormal mitochondrial morphology with evidence of cristae loss and mitochondrial swelling (FIG. 3d). Irp2$^{-/-}$ mice had increased abnormal mitochondrial morphology at baseline compared to WT controls and in response to CS; Irp2$^{-/-}$ mouse airway cells had fewer mitochondria with abnormal morphology (FIG. 3d). Immunohistochemical staining for cytosolic cytochrome c, a marker of mitochondrial damage[28] demonstrated that CS-induced mitochondrial damage localized to alveolar and airway epithelial cells in WT mice. Irp2$^{-/-}$ mice, however, exhibited negligible staining for cytosolic cytochrome c in airway or alveolar epithelial cells after CS exposure (FIG. 3e and FIG. 13).

Figure 14:
FIG. 14. CS increases the labile iron pool and disrupts Fe—S assembly in human epithelial cells. (a) Immunoblot expression of IRP2 in human epithelial Beas2b cells treated with empty vector (CTL) or five shIRP2 clones showing efficiency of IRP2 knockdown in Clone #3 (left). Labile iron pool was measured in CSE-treated (20% 4 h) Beas2B cells (+/− clone 3 shIRP2) (right). Cells were treated with ferric ammonium citrate (Fe$^{3+}$) (FAC) as a positive control. (b) Perls' staining quantification (n=10 images per mouse, n=2 technical replicates) (NC, negative control) in WT and Irp2$^{-/-}$ mice exposed to RA or CS (4 months), n=3 per group. (c) Frataxin expression by immunoblot or RT-PCR analysis in Bea2B cells treated with 20% CSE for the indicated times. (d) Immunoblot analysis of ferritin expression in WT or Irp2$^{-/-}$ mice exposed to RA or CS for 4 months, n=3 per group. (e) Fold change non-heme iron in cytosolic fractions WT (RA, n=12; 1 month CS n=5; 4 months CS n=3; 6 months CS, n=5) or Irp2$^{-/-}$ (RA, n=12; 1 month CS n=5; 4 months CS n=3; 6 months CS, n=5) mice exposed to RA or CS for 1-6 months. (f) Fold change heme iron levels in cytosolic fractions WT (RA, n=8; 1 month CS n=5; 6 months CS, n=5) or Irp2$^{-/-}$ (RA, n=8; 1 month CS n=5; 6 months CS, n=5) mice exposed to RA or CS for 1 or 6 months. (g) Immunoblot analysis of FBXL5 expression in WT or Irp2$^{-/-}$ mice exposed to RA or CS for 1-6 months. n=3 per group. (g) Fluorescent assay for the detection of 2Fe2S mitochondrial (left) or cytosolic (right) Fe—S clusters. (h) Immunoblot analysis of heme oxygenase 1 expression in WT or Irp2$^{-/-}$ mice exposed to RA or CS for 4 months, n=3 per group. All data are mean±s.e.m. *P<0.05, ***P<0.005 by one-way or ANOVA followed by Bonferroni correction. #P <0.05, ##P<0.01 by student's unpaired t-test.
Figure 14:
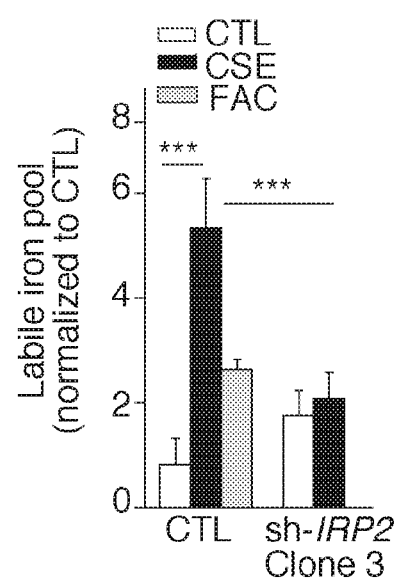
Figure 14:
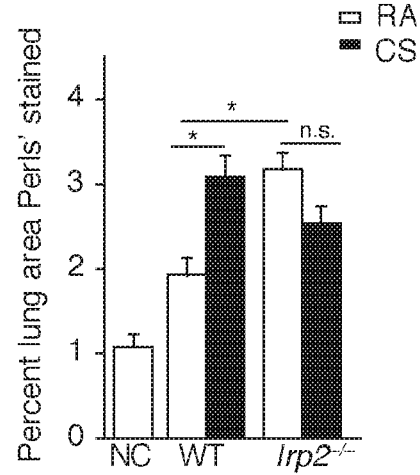
Figure 14:
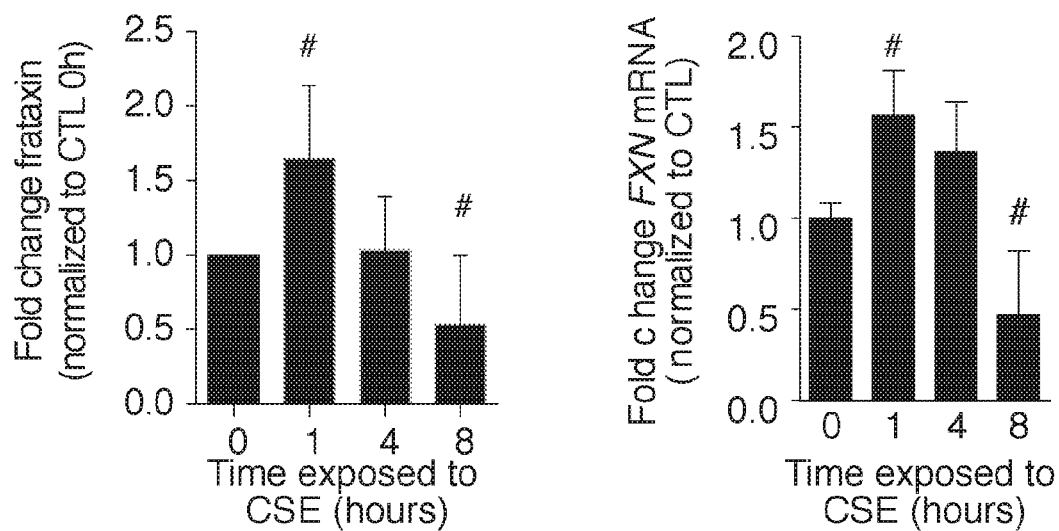
Figure 14:
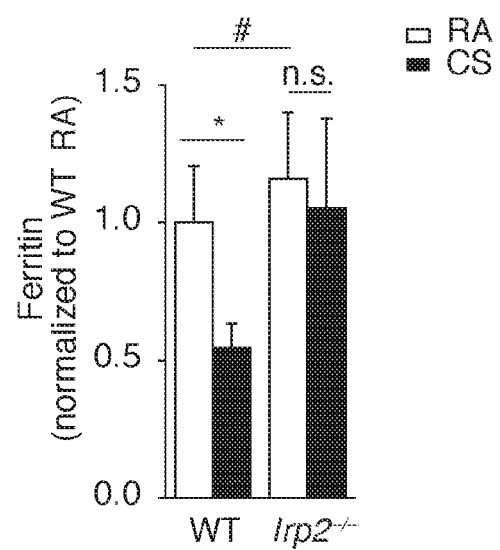
Figure 14:
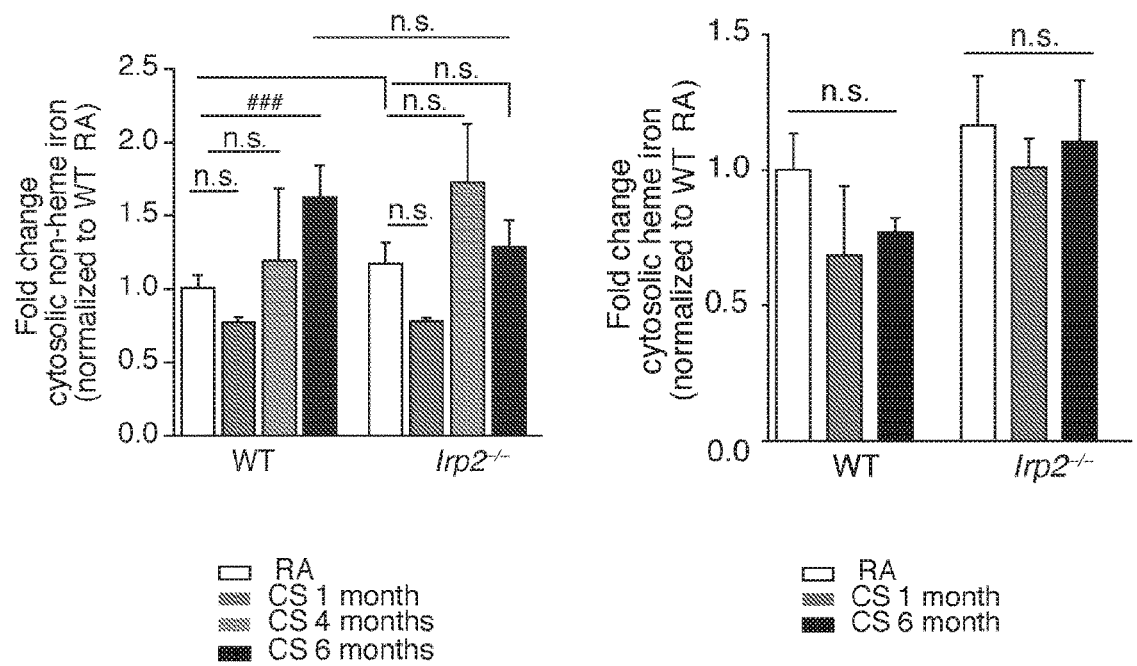
Figure 14:
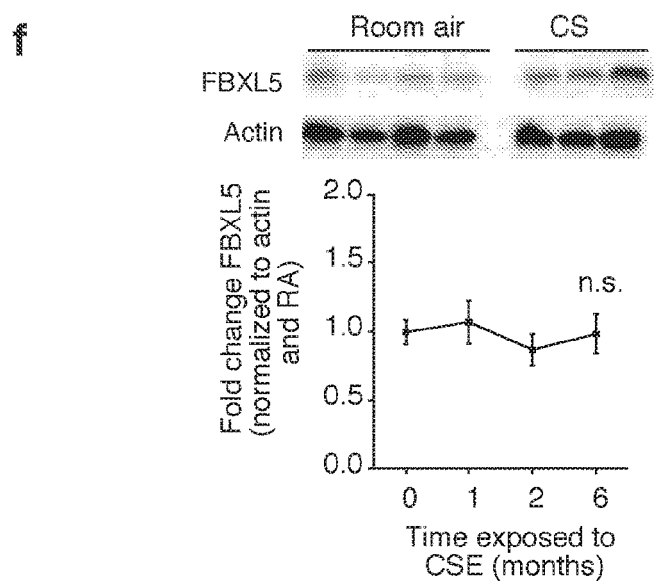
Figure 14:
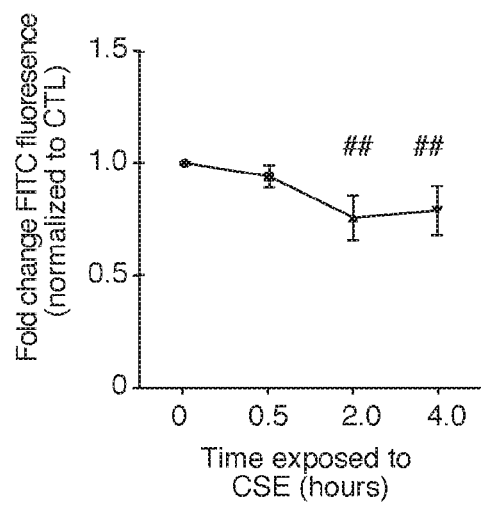
Figure 14:
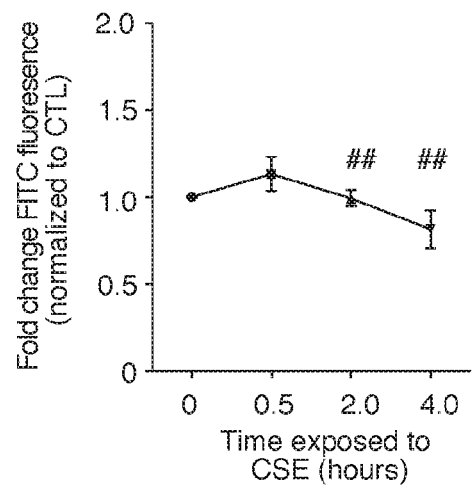
Figure 14:
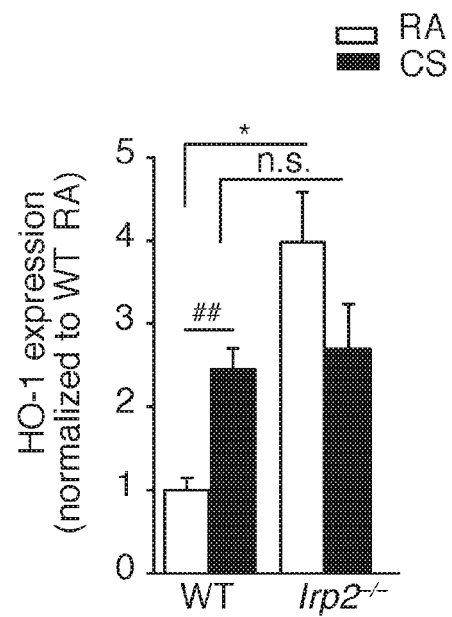

Mitochondria isolated from whole lung homogenates of CS-exposed WT mice had lower membrane potential ($\Delta\Psi$), as indicated by JC1 uptake compared to air-exposed controls (FIG. 3f). Mitochondria isolated from whole lung homogenates of Irp2$^{-/-}$ mice were protected from CS-induced decreases in $\Delta\Psi$ (FIG. 3f). Similarly, primary lung epithelial cells isolated from Irp2$^{-/-}$ mice were resistant to CSE-induced mitochondrial depolarization compared to the WT cells, as measured by TMRE staining (FIG. 3g). Human airway epithelial cells deficient in IRP2 (treated with siRNA for IRP2) were protected from CSE-induced cell death and from the production of CSE-induced mitochondrial reactive oxygen species (mtROS) (FIG. 14a,b). Taken together, these data implicated IRP2 as a regulator of CS-induced mitochondrial dysfunction in experimental COPD.

Using a Seahorse XF96 apparatus, which provides information on mitochondrial function through real-time measurements of oxygen consumption rate (OCR), a marker of oxidative phosphorylation (OXPHOS), and extracellular acidification (ECAR), a surrogate of glycolysis, we determined the rates and reserve capacity of OXPHOS and glycolytic activity, in CSE-exposed WT and Irp2$^{-/-}$ primary lung epithelial cells (FIG. 3h). CSE-exposed WT cells had lower OCR: ECAR ratios, indicative of cells shifting energy metabolism from OXPHOS to glycolysis. CSE-exposed Irp2$^{-/-}$ cells had the opposite response in OCR: ECAR ratio, characterized by greater OXPHOS relative to glycolysis, indicative of enhanced aerobic mitochondrial metabolism with less reliance on glycolysis (FIG. 3h). Thus suggesting that in lung epithelial cells, IRP2 regulated switching from aerobic (OXPHOS) to anaerobic metabolism, as an adaptive response to mitochondrial dysfunction (FIG. 3i).

IRP2 Promoted CS-Induced Mitochondrial Iron Loading

Mitochondria are the main consumers of iron and a number of vital cellular processes rely on precise mitochondrial iron regulation. Failure to control mitochondrial iron leads to mitochondrial iron loss or excessive mitochondrial iron overload, both of which can lead to mitochondrial dysfunction. We wished to investigate whether the observed IRP2-mediated mitochondrial responses to CS (FIG. 3d-h) were related to IRP2-mediated alterations in mitochondrial iron pathways in the lung.

Figure 4:
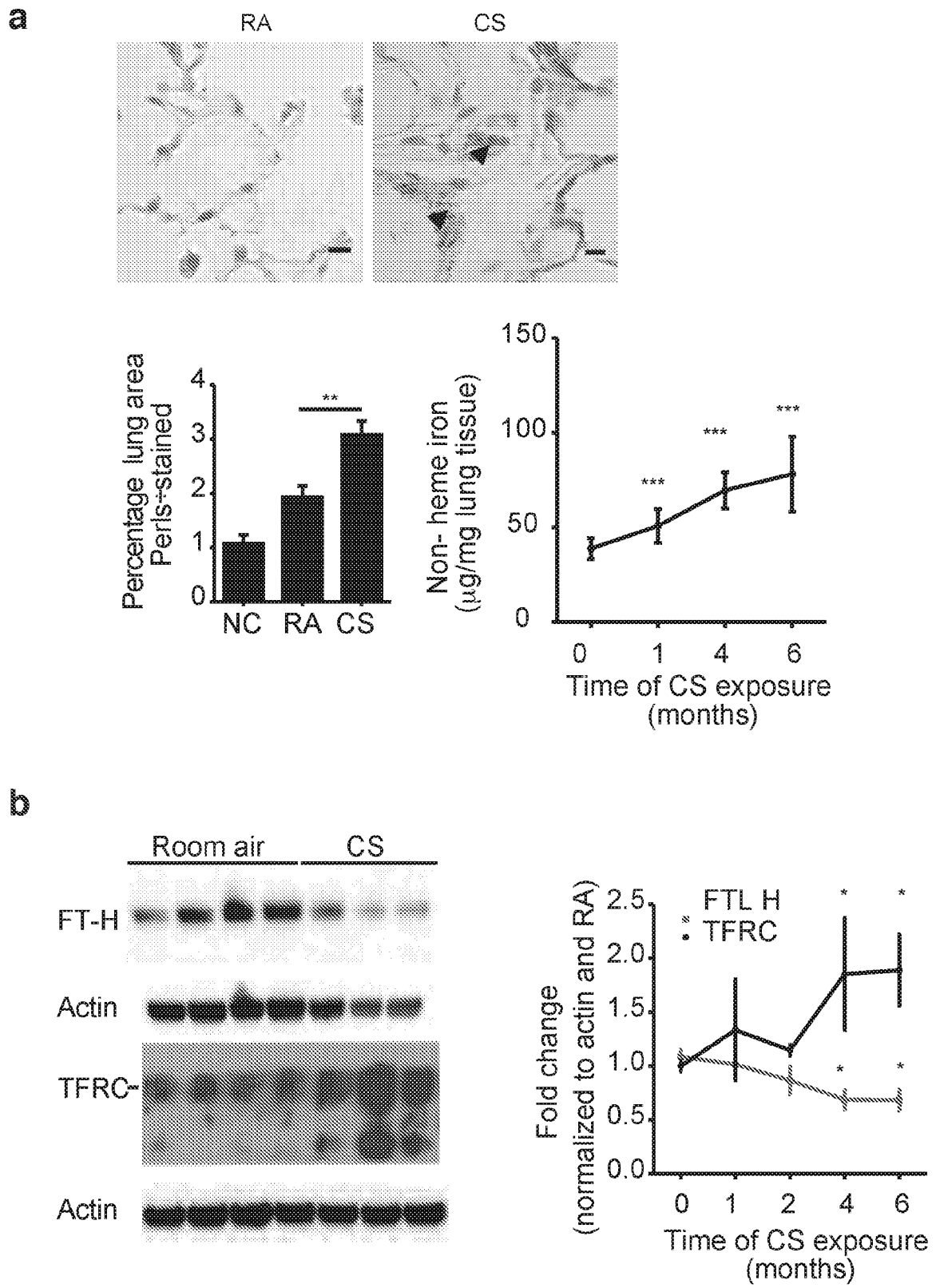
FIG. 4. IRP2-associated mitochondrial iron loading and CS. (a) Representative Perls' stained lung sections (left) (n=2 technical replicates) with quantification (middle) (n=10 images per mouse, n=3 mice per group) and non-heme iron levels (right, n=4 mice per group, n=4 technical replicates) in WT mice exposed to RA or CS (1-6 months). Scale;50 μM. Arrows indicate staining. n.c.; negative control. (b) Representative immunoblot (left) with quantification (right) of transferrin and ferritin (heavy chain) expression in whole lung of WT and Irp2$^{-/-}$ mice exposed to RA or CS (1-6 months) (n=2 technical replicates, n=5 per group). (c) Total non-heme iron (left, n=4 technical replicates) and fold change mitochondrial and cytosolic non-heme iron (right) in WT mouse lungs exposed to RA or CS (1-6 months), n=3 technical replicates, n=5 mice per group. (d) Fold change non-heme iron (left) and heme iron (right) in mitochondrial fractions from WT mouse lungs exposed to RA or CS (1-6 months), n=2 technical replicates. (e) Mitoferrin 2 and (f) frataxin expression in whole lung homogenates from WT and Irp2$^{-/-}$ mice exposed to RA or CS (1-4 months). (g) Mitochondrial non-heme (left), mitochondrial heme iron (right), (h) MCC (left) and IL-6 protein concentrations (right) in the lungs of WT and Fxn$^{ki/ko}$ mice exposed to RA or CS (1 month). (i) Schematic of mitochondrial iron loading regulated by IRP2 in experimental COPD. All data are mean±s.e.m. *P<0.05, P<0.01, *P<0.005 by one-way ANOVA followed by Bonferroni correction. $^{\#}$P<0.05 by student's unpaired t-test.
Figure 4:
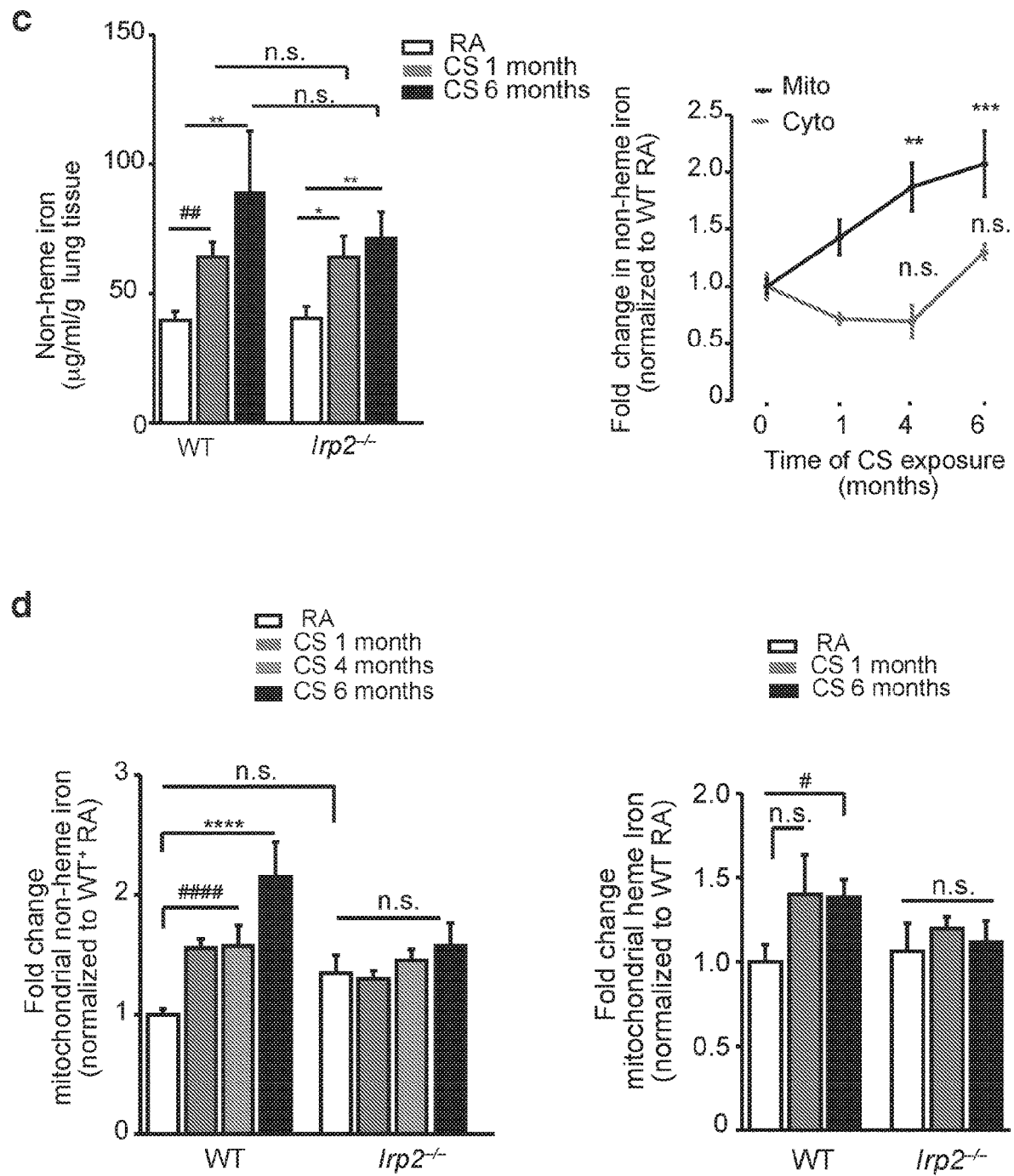
Figure 4:
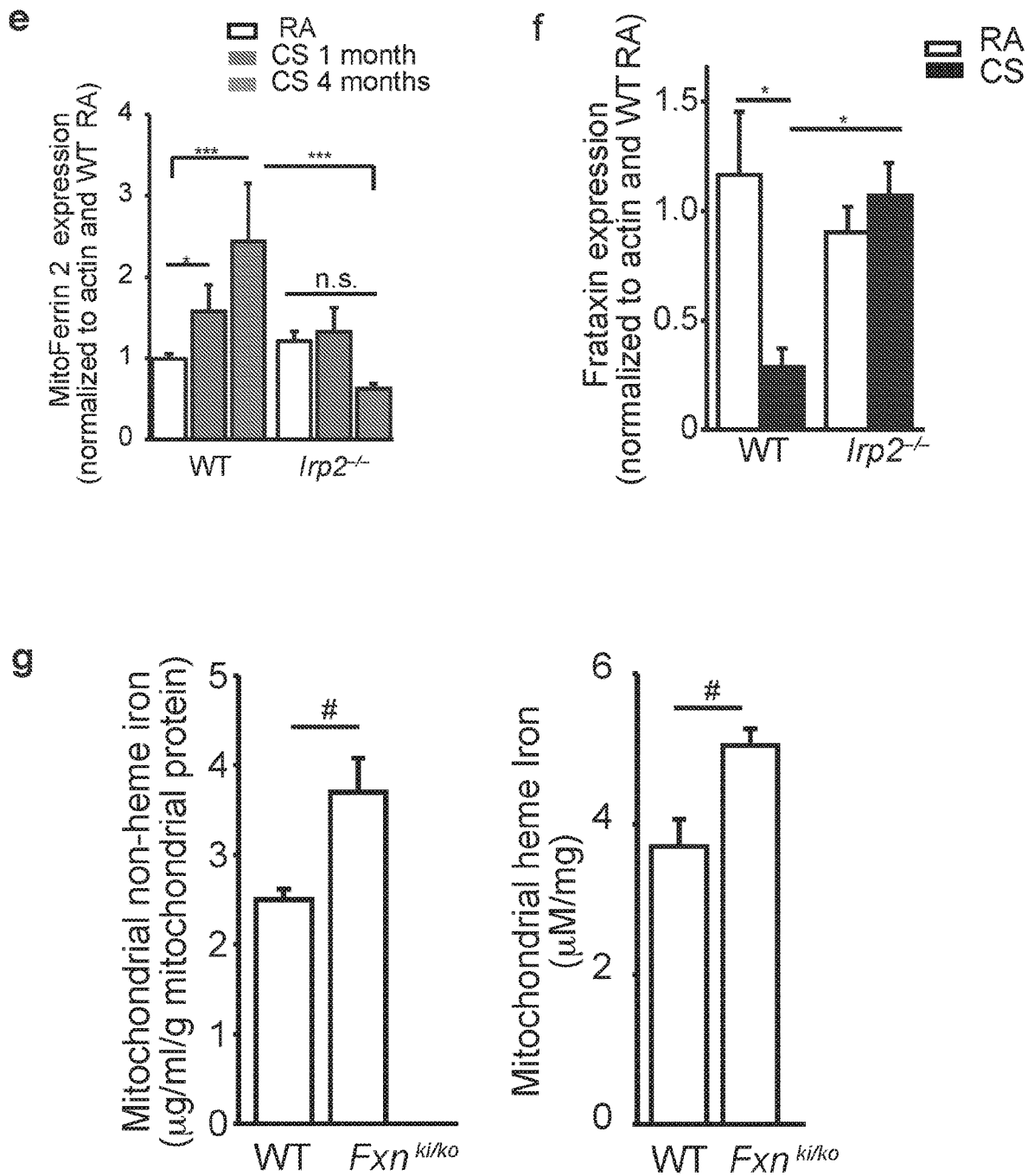
Figure 4:
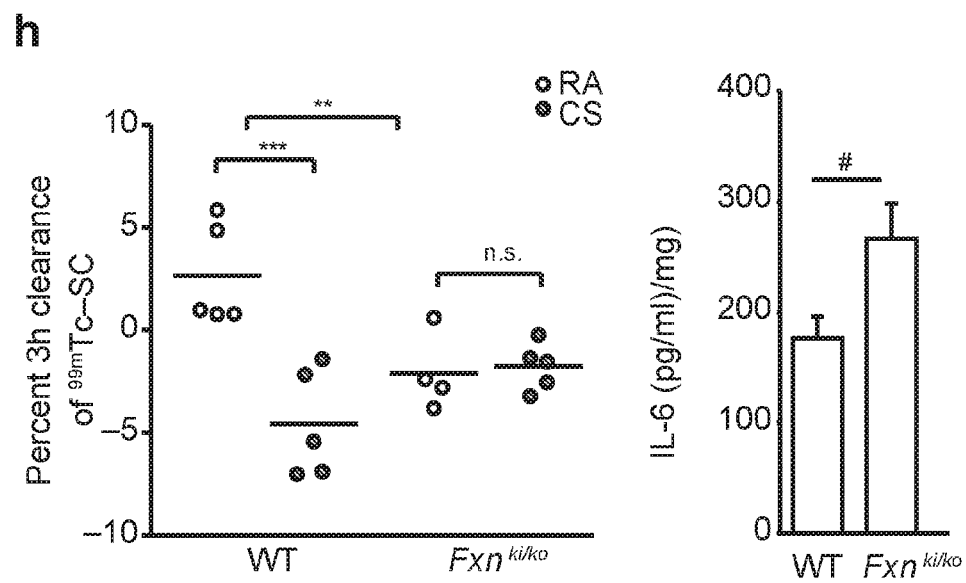
Figure 4:
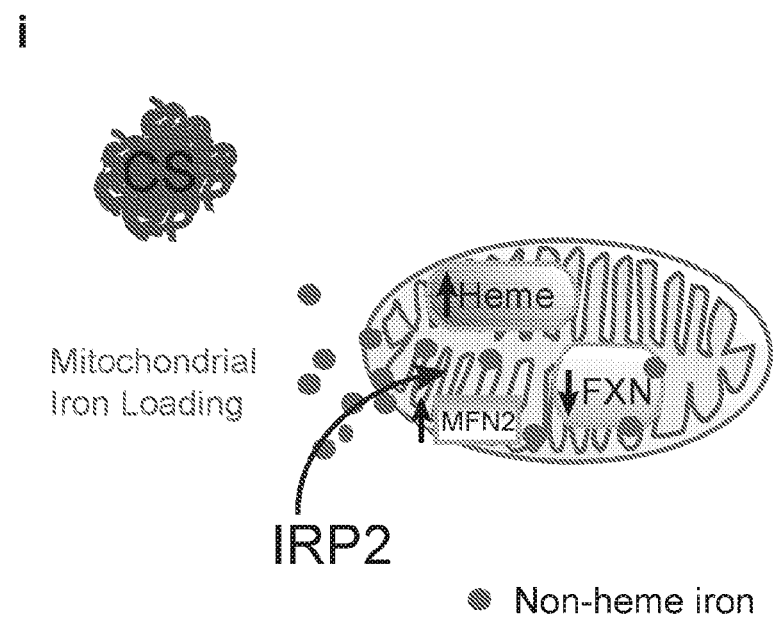

We first investigated whether CS regulated general iron metabolism in the lung. In body tissues, iron (Fe) is found either as non-heme free iron in the ferric (Fe$^{3+}$) or ferrous (Fe$^{2+}$) state or as heme iron (Fe$^{2+}$ complexed with protoporphyrin IX). Consistent with greater IRP2 expression in CS-exposed WT mice, WT mice had higher non-heme iron in inflated lung sections and in whole lung homogenates when compared to air-exposed WT mice (FIG. 4a). Whole lung homogenates of WT mice also had higher and lower expression of the IRP2-target proteins TfR and ferritin respectively (FIG. 4b). Additionally, intracellular free iron was higher in human airway epithelial cells upon exposure to aqueous CSE (FIG. 14a). These data indicated that in experimental models of COPD, CS increased iron deposition in the airways of mice. CS-exposed Irp2$^{-/-}$ mice had similar total non-heme iron levels in whole lung tissue, when compared to CS-exposed WT mice (FIG. 4c); however Perls' stained CS-exposed Irp2$^{-/-}$ mouse lungs had less iron deposition than Perl's stained CS-exposed WT mouse lungs (FIG. 14b). Furthermore, intracellular free iron did not change in CSE-exposed human airway epithelial cells deficient in IRP2 (treated with shRNA targeted to IRP2) (FIG. 14a).

Once inside the cell, free iron may be delivered to ferritin, to iron-containing proteins, or may be imported into mitochondria for heme or iron-sulfur (Fe—S) cluster biosynthesis. Non-heme and heme iron levels were higher in mitochondrial fractions of WT mouse lungs exposed to CS when compared to air-exposed controls (FIG. 4c,d). Increased mitochondrial iron import is reliant on the use of the inner mitochondrial membrane iron transporter mitoferrin 2. Mitoferrin 2 levels were higher in CS-exposed mice when compared to air-exposed controls (FIG. 4e), suggesting increased import of iron into mitochondria. Another indicator of increased iron loading, loss of the mitochondrial Fe—S regulator frataxin, was also associated with CS exposure in whole lung homogenates of WT mice as well as in human airway epithelial cells treated with CSE (FIG. 4f and FIG. 14c). CS reduced ferritin expression but did not change the expression of cytosolic non-heme or heme iron or the cytosolic iron binding protein F-box and leucine-rich repeat protein 5 (FBXL5, also a negative regulator of IRP2[21]) (FIG. 14d-f). Additionally, CSE impaired mitochondria and cytosolic Fe—S cluster assembly in human airway epithelial cells (FIG. 14g). Taken together, these data demonstrated that CS induced mitochondrial iron loading in experimental COPD.

Irp2$^{-/-}$ mice were protected from the effects of CS on ferritin and mitoferrin 2 expression when compared to CS-exposed WT mice (FIG. 4d,e and FIG. 14d). Irp2$^{-/-}$ mice were also protected from CS-associated higher mitochondrial non-heme iron and mitochondrial heme iron levels (FIG. 4d), suggesting that IRP2 promoted CS-induced mitochondrial iron loading. Irp2$^{-/-}$ mice had higher baseline levels of HO-1, which did not change upon CS exposure compared to CS-exposed WT mice (FIG. 14h), suggesting more baseline protection from mitochondrial-mediated cell death.

To assess whether abnormally increased mitochondrial iron overload was pathogenic in experimental COPD, we evaluated whether mice with higher mitochondrial iron loading (i.e., mice with reduced frataxin expression) had differential responses to CS in our CS-induced impairment of MCC (bronchitis model). We chose to use this acute 1-month exposure model to test our hypothesis, as we observed significant differences (P<0.05) in CS-induced mitochondrial iron loading between the WT and Irp2$^{-/-}$ mice at this time-point (FIG. 4d). Here we show that mice deficient in frataxin (i.e., mice with a heterozygous transgenic insertion (GAA$_{230}$ expansion) of mutated frataxin (KI) and a heterozygous deletion of frataxin (KO))(Fxn$^{ki/ko}$) had higher mitochondrial non-heme and heme iron levels and displayed significantly impaired baseline MCC function (P<0.05) as well as higher baseline levels of whole lung IL-6 protein concentrations (FIG. 4g,h), when compared to WT mice. This data suggested that CS-induced mitochondrial iron loading might be pathogenic in experimental COPD (FIG. 4i).

IRP2 and CS Increased Lung COX Activity and Expression

Figure 5:
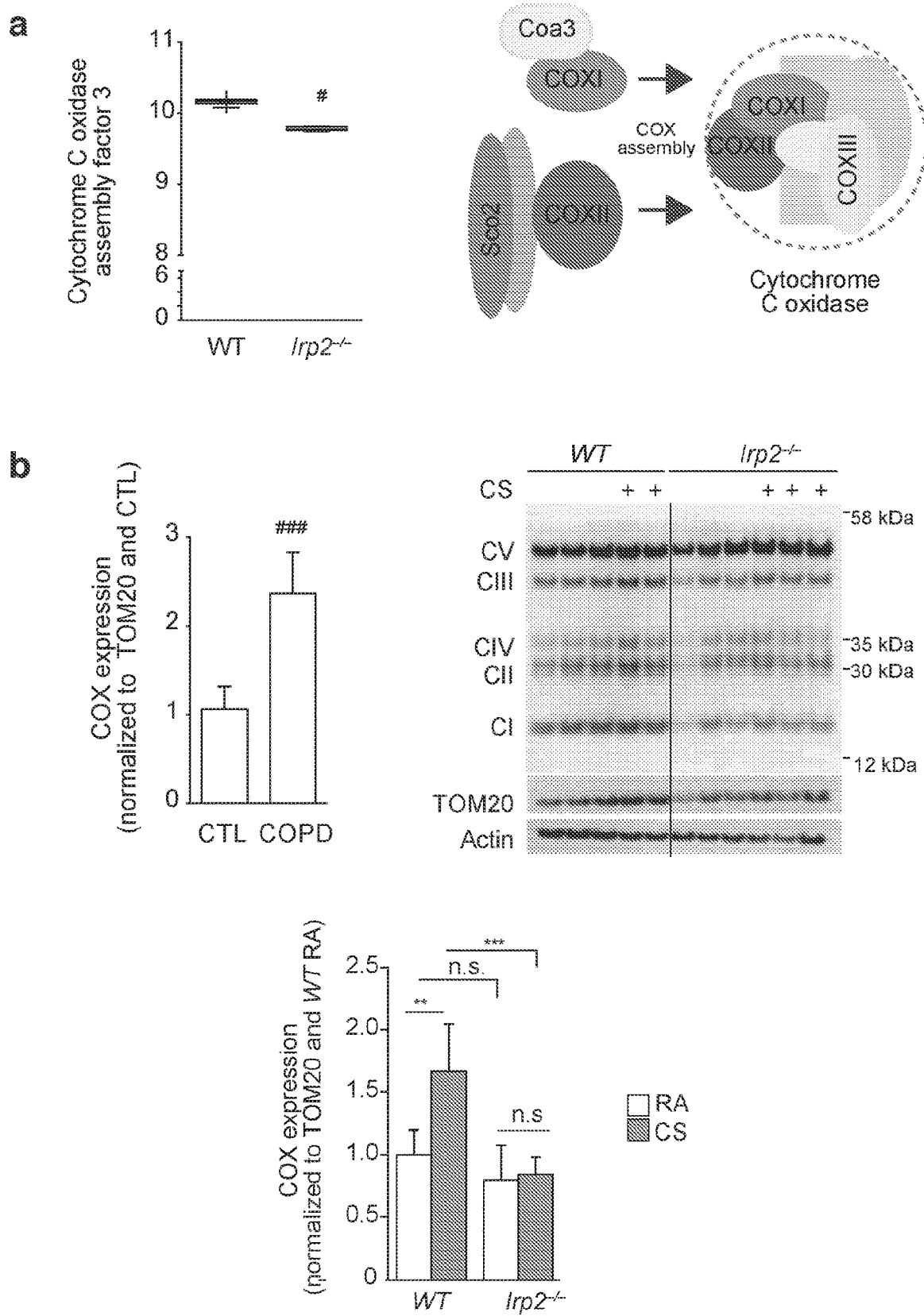
FIG. 5. COX is pathogenic in experimental COPD. (a) Coa3 expression (left) in WT and Irp2$^{-/-}$ mouse lungs (n=6 WT, n=5 Irp2$^{-/-}$), schematic of COX assembly (middle) and COX expression by immunoblot analysis (right) in lung tissue from individuals with COPD (n=5) and controls (n=5), n=2 technical replicates. (b) Representative immunoblot expression (left) of OXPHOS complexes I-V in mitochondrial-enriched fractions from WT and Irp2$^{-/-}$ mouse lungs exposed to RA or CS (4 months), with quantification of Complex IV expression (right), n=2 technical replicates. (c) Time course of COX activity (1-4 months) (left) and total COX activity (4 months) in mitochondrial fractions of WT or Irp2$^{-/-}$ mice exposed to RA or CS (n=3 per group, n=3 technical replicates). (d) Representative immunoblot (left) as in (b), time course of COX activity (0.5-4 h) (middle) and COX activity at 4 h (right) in primary lung epithelial cells from WT or Irp2$^{-/-}$ mice exposed to 20% CSE, n=2 per group, n=2 technical replicates. (e) MCC (left), total BALF leukocytes (middle), total protein levels (right), (f) BALF IL-33 (left, ELISA), BALF IL-6 (right, ELISA) protein concentration, (g) total lung non-heme iron, (h) mitochondrial non-heme iron (left) and mitochondrial-heme iron (right) levels in WT and Sco2$^{ki/ko}$ mice exposed to RA or CS (1 month), n=3 technical replicates. (i) Schematic of the role of COX in experimental COPD. All data are mean±s.e.m. *P<0.05, P<0.01, *P<0.005 by one-way ANOVA followed by Bonferroni correction. $^{\#}$P<0.05, $^{\#\#}$P<0.01, $^{\#\#\#}$P<0.005 by unpaired student's t-test.
Figure 5:
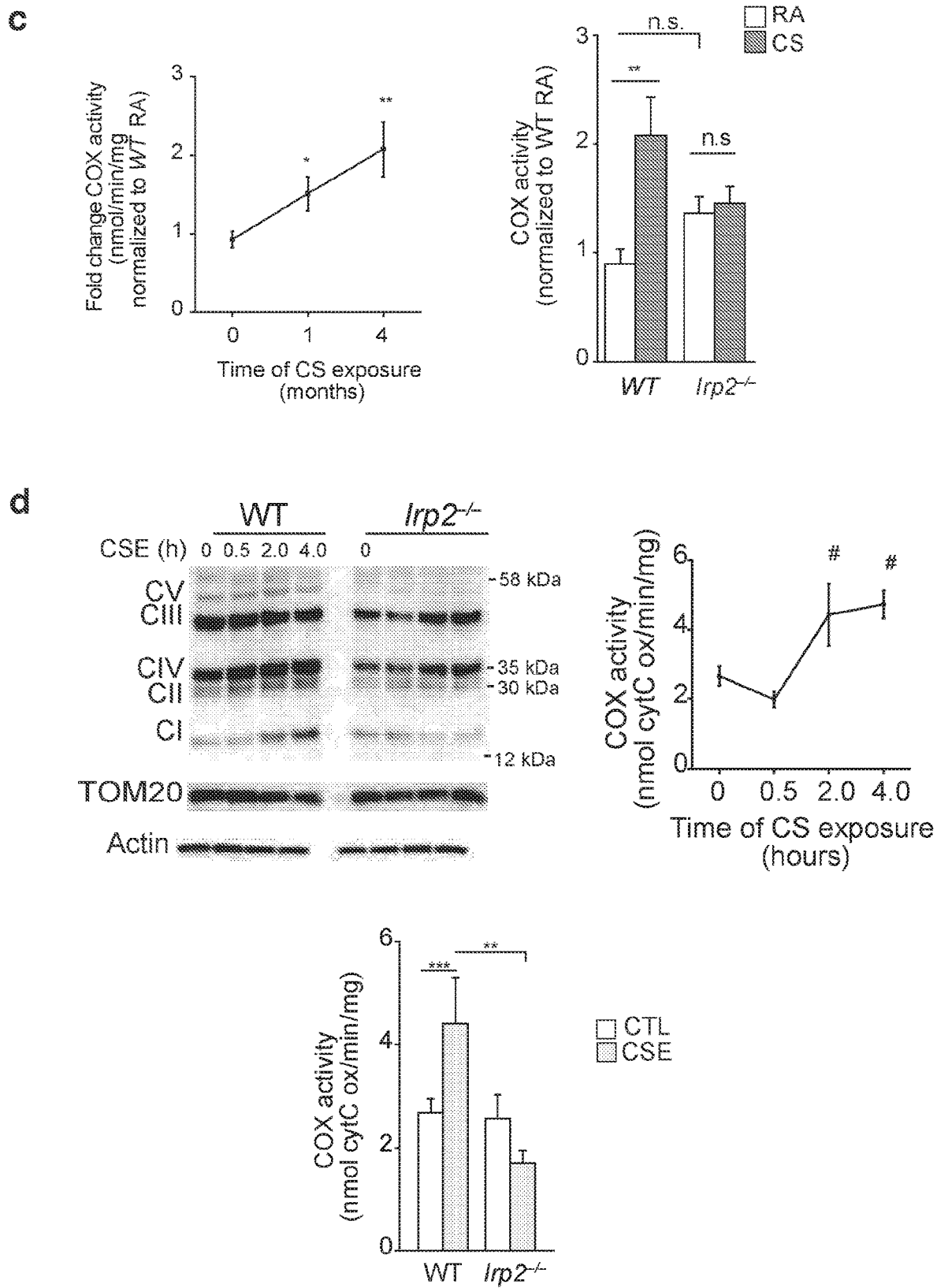
Figure 5:
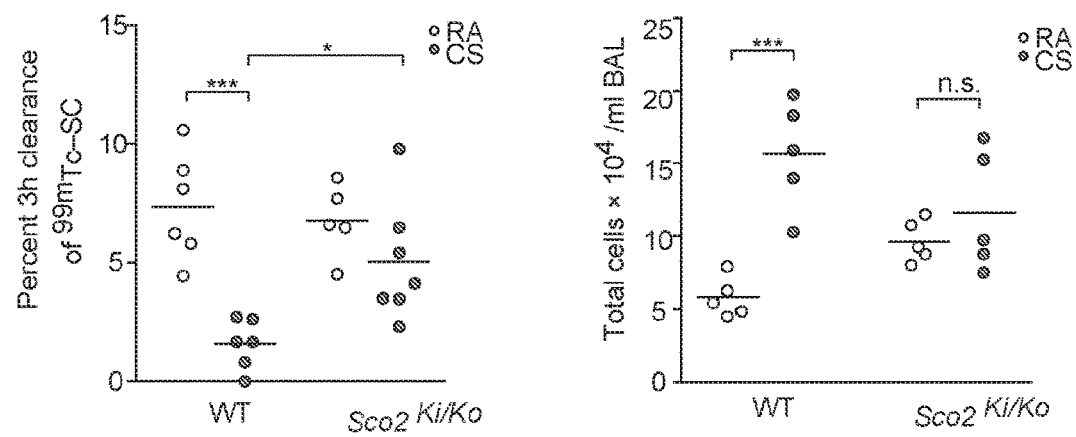
Figure 5:
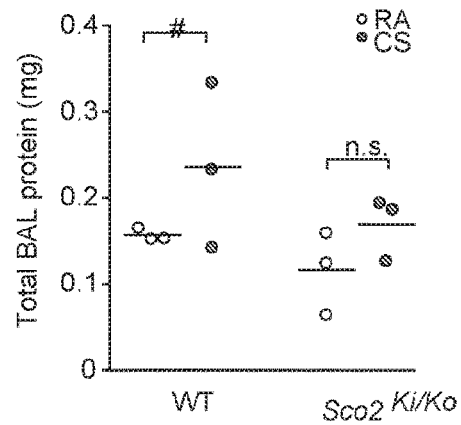
Figure 5:
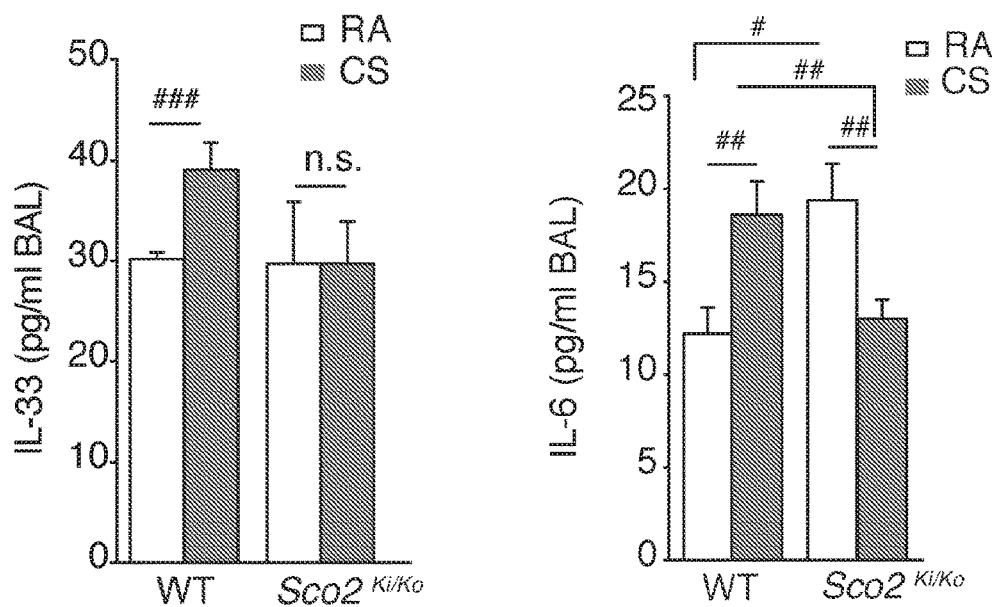
Figure 5:
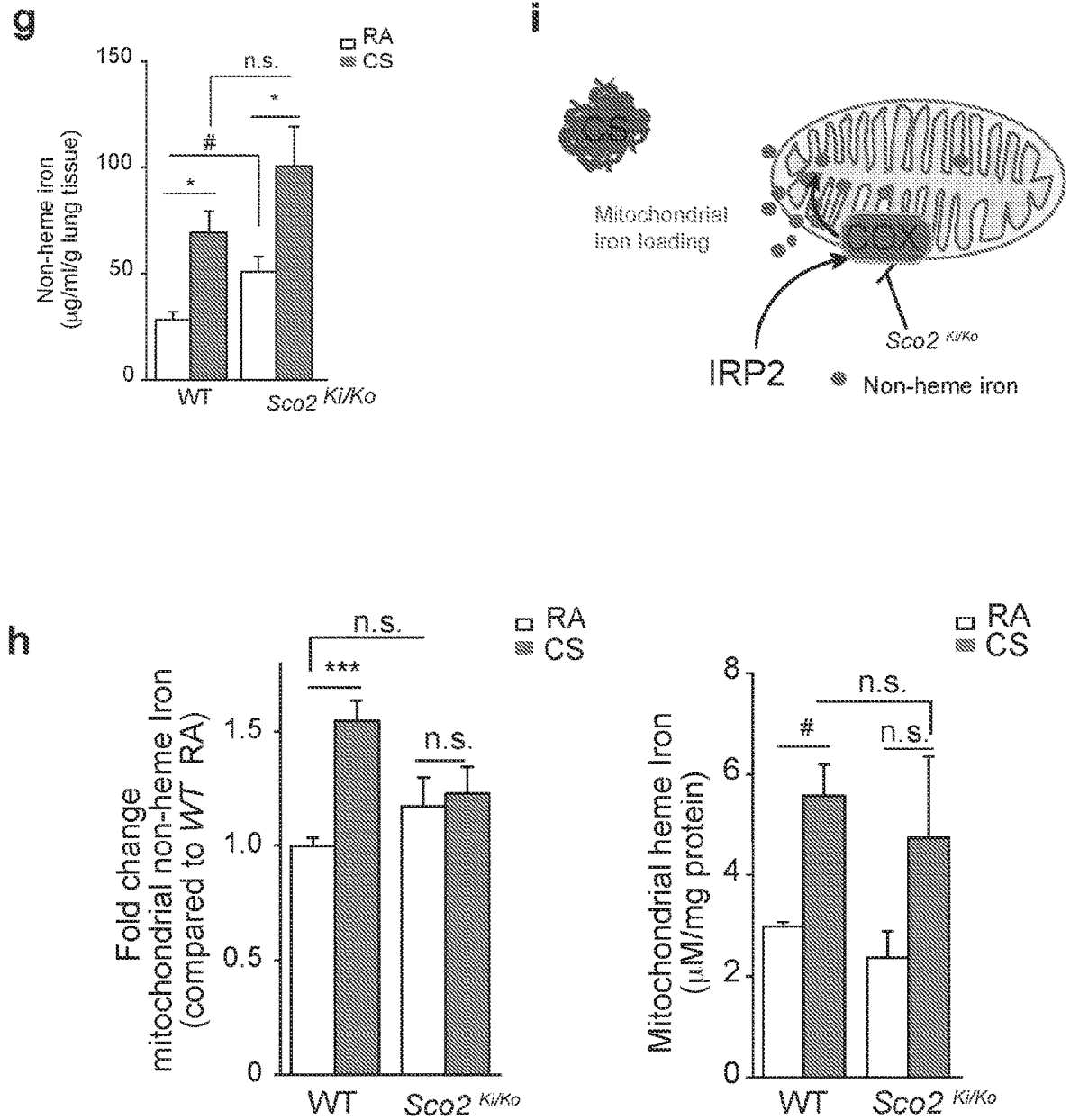

To investigate the mechanism of IRP2 associated mitochondrial iron loading and CS-induced mitochondrial dysfunction, we focused our attention to the mitochondrial genes identified in our RIP-Seq study and community-based gene expression analysis (FIG. 3a). The most significant differentially expressed gene (P<0.01) in this analysis was cytochrome C oxidase (COX) assembly factor 3 (coa3) with Irp2$^{-/-}$ mice having lower expression than WT mice (FIG. 3a and FIG. 5a). COA3 encodes coiled coil domain-containing protein 56 (CCDC56), a mitochondrial protein that stabilizes COX subunit-I and promotes its assembly and activity (FIG. 5a). COX is the terminal electron acceptor of the mitochondrial electron transport chain responsible for the conversion of oxygen into water. A number of other subunits and factors important for COX assembly (COX18, COX8A) and mitochondrial oxidative phosphorylation including NADH dehydrogenase (Ubiquinone) 1 (NDUF) alpha subcomplex, 6 (NDUFA6) and NDUF beta subcomplex, 9 (NDUFB9) (Complex I), succinate dehydrogenase complex, subunit B, Iron Sulfur (SDHB) (Complex II) and ubiquinol-cytochrome C reductase hinge protein (UQCRH) (Complex III) were also differentially expressed in Irp2$^{-/-}$ versus WT mice by this analysis, as well as other proteins important for mitochondrial integrity and apoptosis (FIG. 3a).

Consistent with higher IRP2 expression and with altered expression of COX-related mitochondrial genes in WT mice versus Irp2$^{-/-}$ mice (FIG. 3a and FIG. 5a), we show for the first time that COX expression is higher in COPD lung biopsies when compared to control subjects (FIG. 5a).

Figure 15:
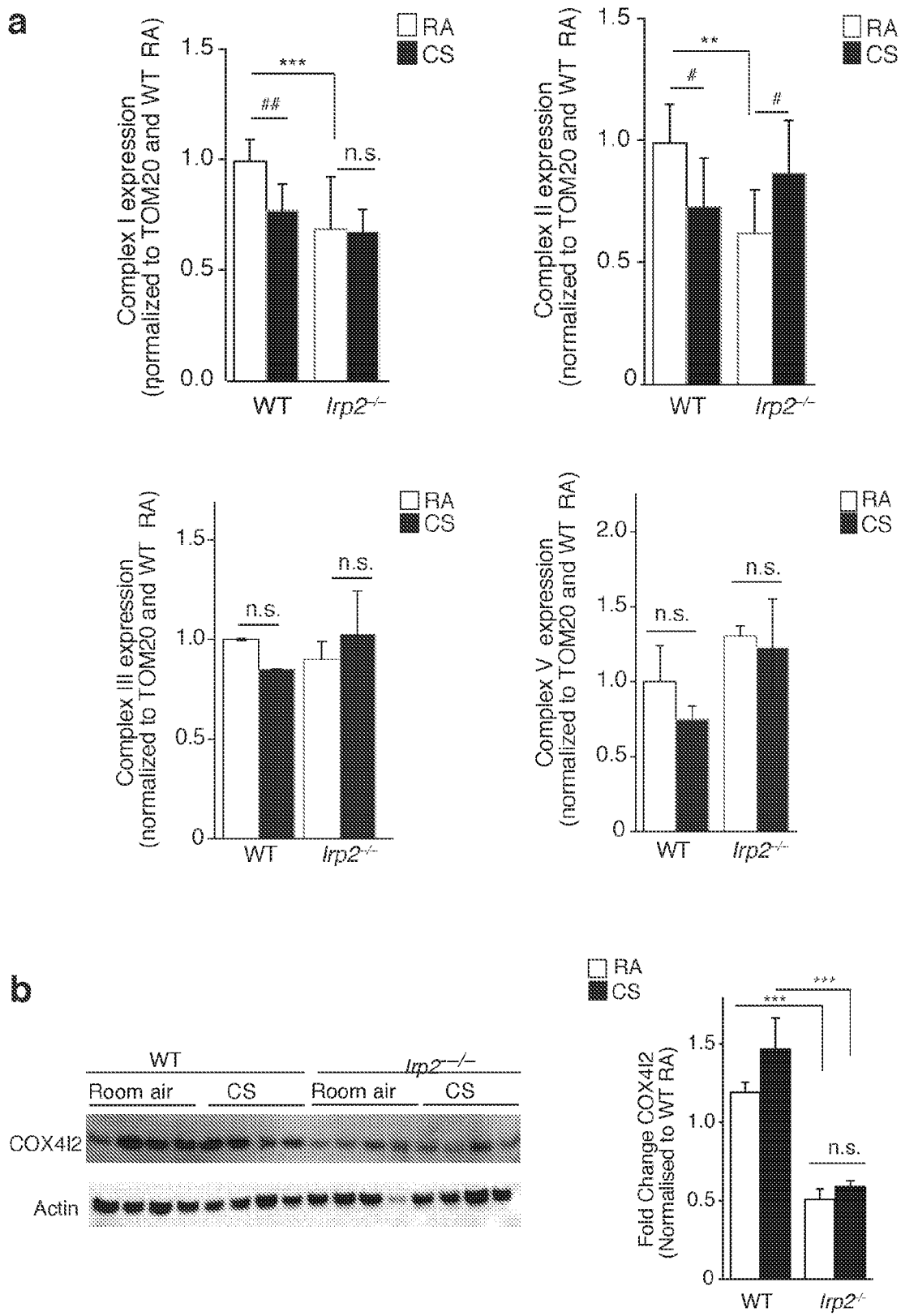
FIG. 15. IRP2 regulates the response of ETC Complexes to CS. (a) Immunoblot analysis of Complexes I-V of the electron transport chain in normalized mitochondrial-enriched fractions generated from the lungs of WT or Irp2$^{-/-}$ mice exposed to RA or CS (4 months), n=3 per group. (b) COX4I2 expression and densitometry of WT or Irp2$^{-/-}$ mice exposed to RA or CS (6 months), n=3 per group. (c) MCC of mice with two knockin mutated alleles of Sco2 (Sco2$^{ki/ki}$) after 1 month exposure to RA or CS. (d) Infiltrating alveolar macrophages in the BAL of WT and Sco2$^{ki/ko}$ mice exposed to RA or CS (1 month). (e) Fold change non-heme iron levels and (f) heme iron levels in cytosolic fractions of WT and Sco2$^{ki/ko}$ mice after 1-month exposure to RA or CS, n=3 per group. All data are mean±s.e.m. *P<0.05 by one-way ANOVA. #P<0.05 by unpaired Student's t-test.
Figure 15:
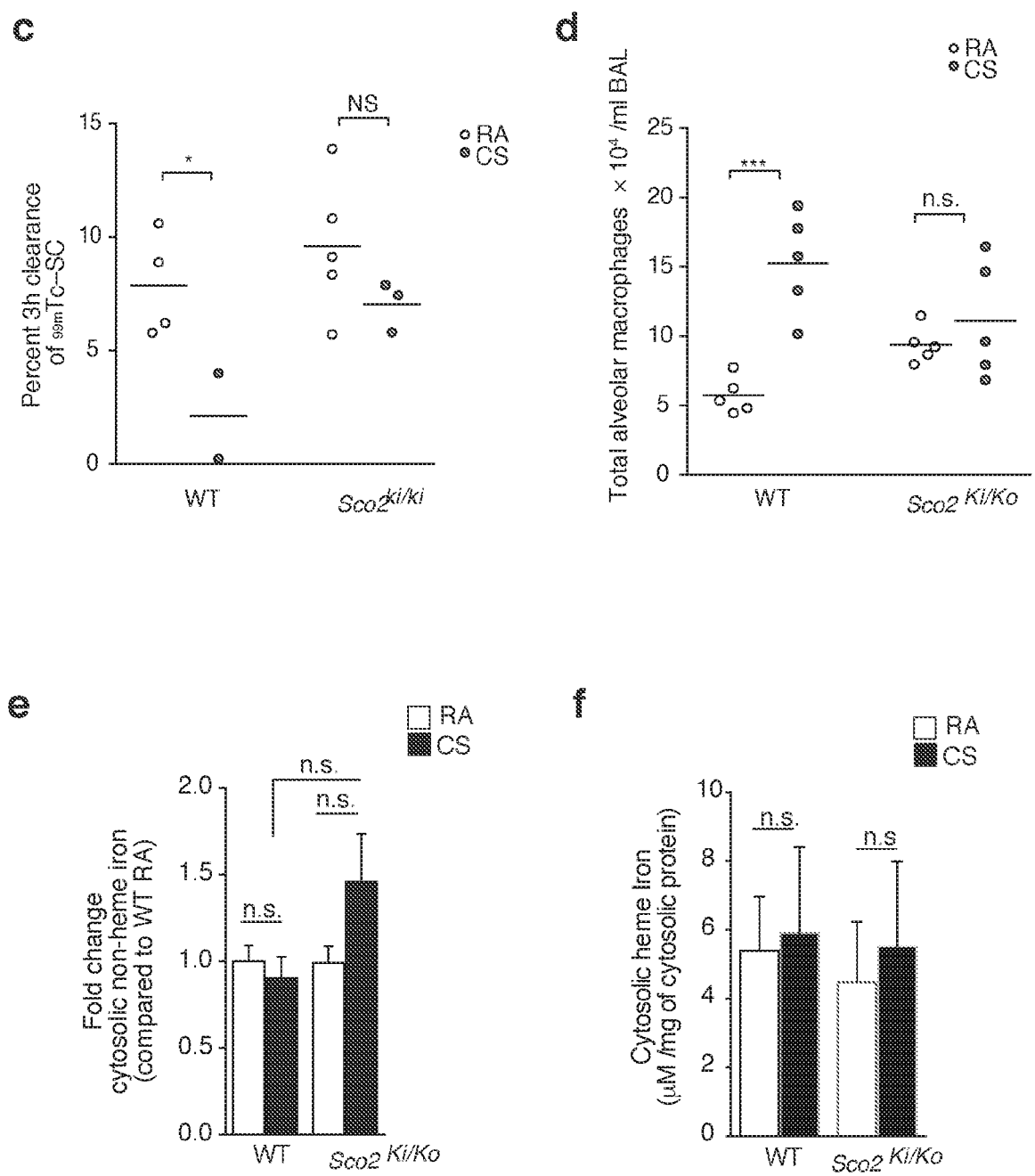

Using an antibody that detects each complex of the mitochondrial electron transport chain, we show that COX expression was higher in CS-exposed WT mice compared to CS-exposed Irp2$^{-/-}$ mice (FIG. 5b). Irp2$^{-/-}$ mouse lungs also exhibited less CS-induced reduction in the expression of Complexes I and II (FIG. 15a). Expression of the lung specific isoform of COX (COX4I2), which renders lung COX two-fold more active, compared with COX in other tissues that lack COX4I2, was also higher in CS-exposed WT mice. Irp2$^{-/-}$ mice had lower COX4I2 expression when compared to WT mice, which did not change upon CS exposure (FIG. 15b). Similarly, COX activity was higher in mitochondrial fractions isolated from WT mice exposed for 1 month and 4 months CS compared to air-exposed controls (FIG. 5c). COX activity was higher in mitochondria from CS-exposed WT mouse lungs but did not increase in mitochondria from CS-exposed Irp2$^{-/-}$ mouse lungs (FIG. 5c). CSE-exposed WT lung epithelial cells had greater COX expression and activity compared to CSE-exposed airway epithelial cells from Irp2$^{-/-}$ mice (FIG. 5d).

To examine the function of COX in the response of the lung to CS, we used mice with impaired COX (activity and expression) in our CS-induced bronchitis model. COX is a multi-subunit complex whose assembly requires >20 ancillary factors including synthesis of cytochrome c oxidase (SCO2) (FIG. 5a). We assessed the MCC of Sco2$^{ki/ko}$ and Sco2$^{ki/ki}$ mice exposed acutely to CS. WT mice had impaired MCC, increased BAL leukocyte counts and increased total BALF protein levels (FIG.5e and FIG. 15c,d). Conversely, Sco2$^{ki/ko}$ and Sco2$^{ki/ki}$ mice were protected from CS-induced loss of MCC (with Sco2$^{ki/ko}$ having greater protection than Sco2$^{ki/ki}$ mice) (FIGS. 5e and 15c,d). CS-exposed Sco2$^{ki/ko}$ mice exhibited lower BALF total protein, IL-6, and IL-33 protein concentrations and lower BAL leukocyte counts than CS-exposed WT mice (FIGS. 5e and 15c,d) supporting the hypothesis that increased COX confers pathogenicity in experimental COPD.

To determine whether loss of COX resulted in higher mitochondrial iron in a similar manner to loss of IRP2, we measured total lung tissue non-heme iron levels, as well as cytosolic and mitochondrial iron (non-heme and heme) in WT and Sco2$^{ki/ko}$ mouse lungs exposed to air or CS (1 month). Consistent with results obtained in WT mice, CS-exposed WT mice had higher total lung non-heme iron levels as well as higher mitochondrial non-heme and heme iron levels compared to air-exposed WT mice (FIG. 5g-h). Similar to the Irp2$^{-/-}$ mice, Sco2$^{ki/ko}$ mice were protected from CS-increases in mitochondrial non-heme iron (FIGS. 4d and 5h). No difference in mitochondrial heme levels or cytosolic non-heme and heme iron levels was observed in air- or CS-exposed Sco2$^{ki/ko}$ mice, when compared to the WT mice (FIG. 5h and FIG. 15e,f). These data suggested that IRP2 increased COX, which may be associated with altered mitochondrial non-heme iron in experimental COPD (FIG. 5i).

Targeting Mitochondrial Iron in Experimental COPD

Figure 6:
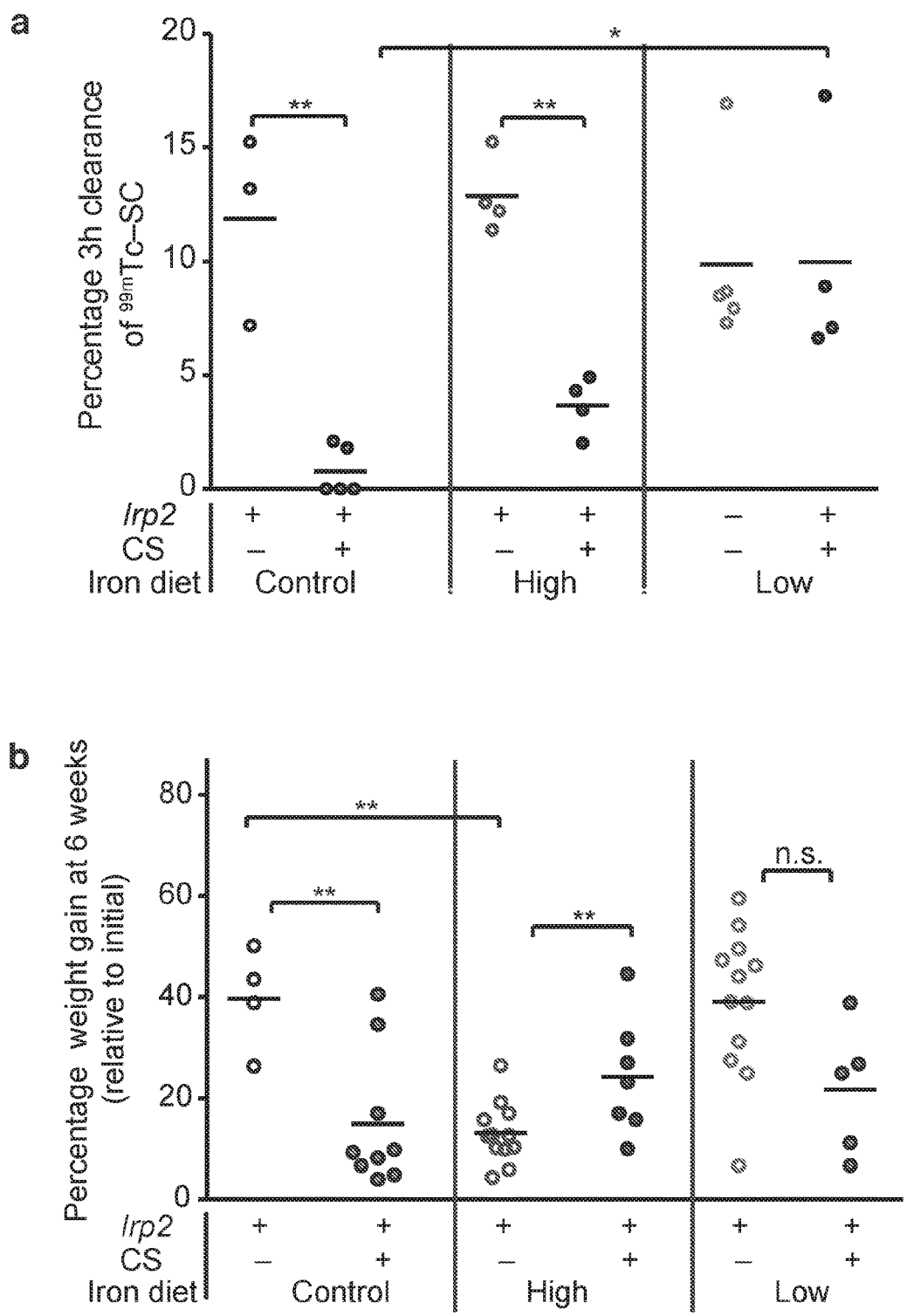
FIG. 6. Targeting mitochondrial iron in experimental COPD. (a) MCC and (b) percentage weight gain of WT mice exposed to RA or CS (1 month) on a control (300 ppm iron), low iron (6 ppm iron) or high iron diet (2% carbonyl iron). (c) MCC in WT and Irp2$^{-/-}$ mice exposed to RA or CS (1 month) and treated with DFP as a prophylactic dosing strategy or as a therapeutic dosing strategy; blue arrows indicate point of DFP addition. (d) Percentage weight gain (relative to initial weight at the start of smoke exposure), (e) fold change in lung mitochondrial non-heme iron (control n=8;DFP control n=8; 1 month CS n=10; 6 weeks CS n=4; 6 weeks +DFP n=4; 8 weeks CS n=4; 8 weeks CS+DFP n=4; n=2 technical replicates), (f) total BAL leukocytes and (g) total BALF protein in WT mice with CS-induced pulmonary inflammation and injury treated with DFP using a therapeutic dosing strategy as in (c), but continued for 2 or 4 weeks of CS exposures. Black arrows indicate time points and blue arrows indicate time of DFP addition. (h) Schematic of the major findings of this study. All data are mean±s.e.m. *P<0.05, P<0.01, *P<0.005 by one-way ANOVA followed by Bonferroni correction.
Figure 6:
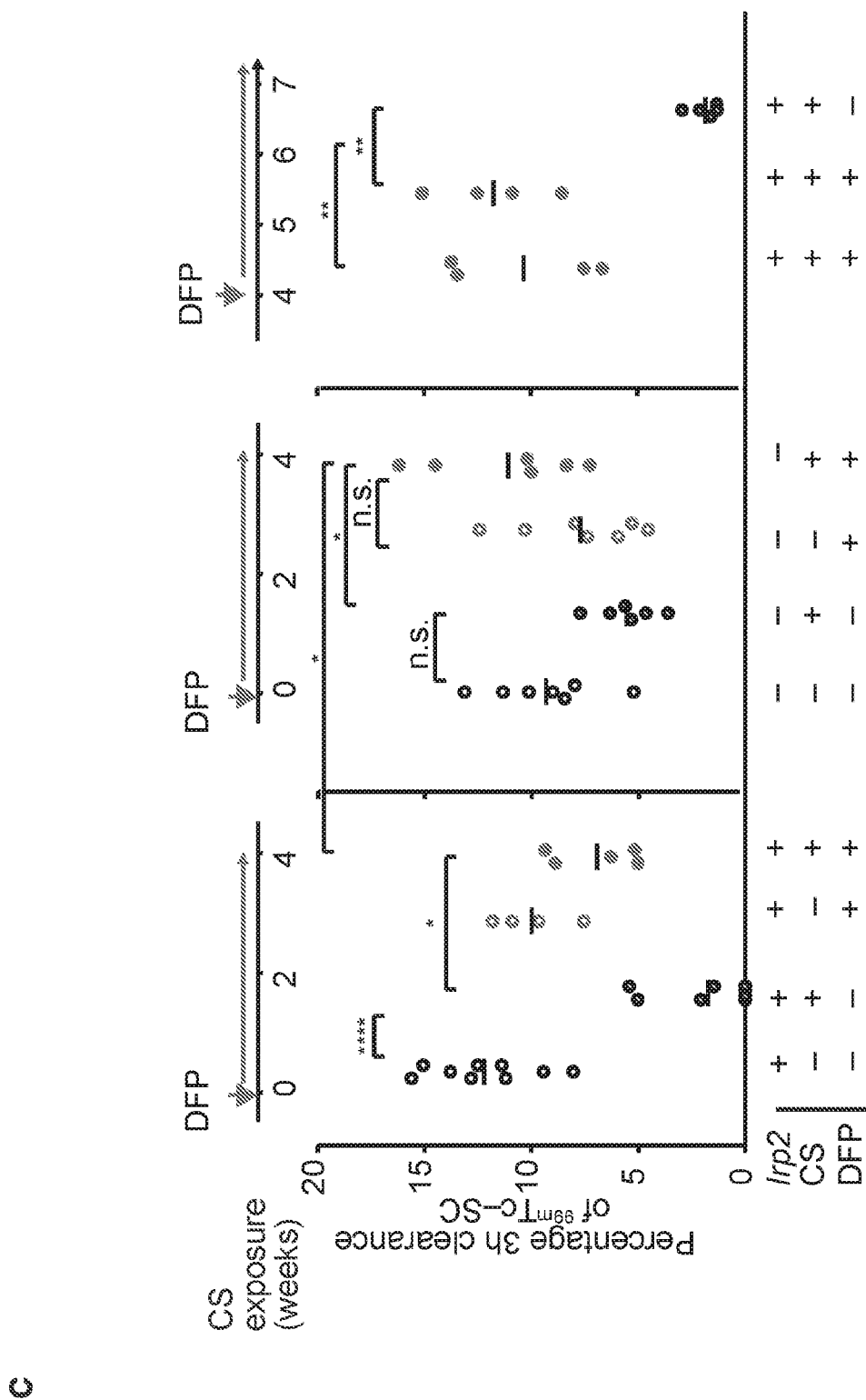
Figure 6:
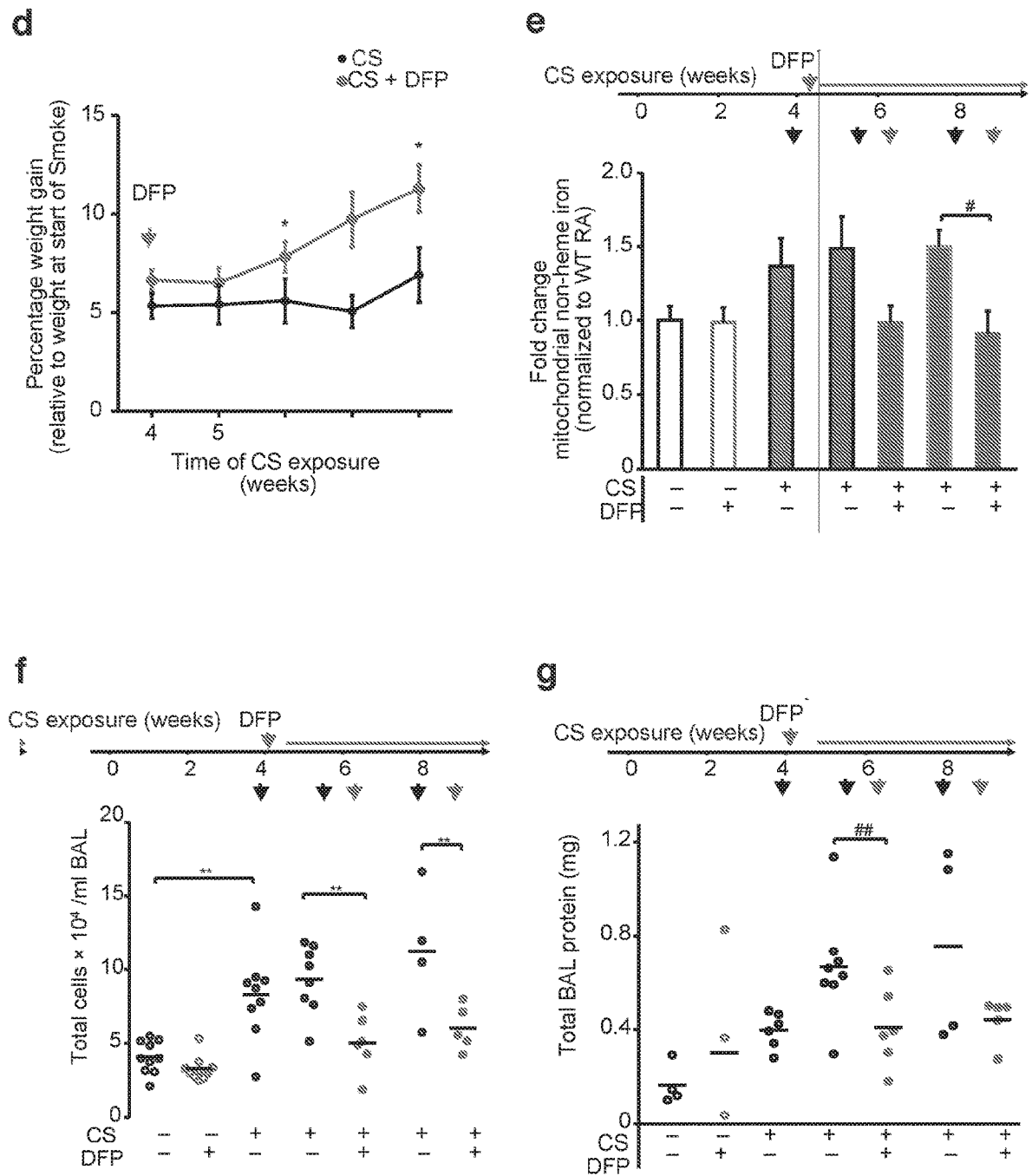
Figure 6:
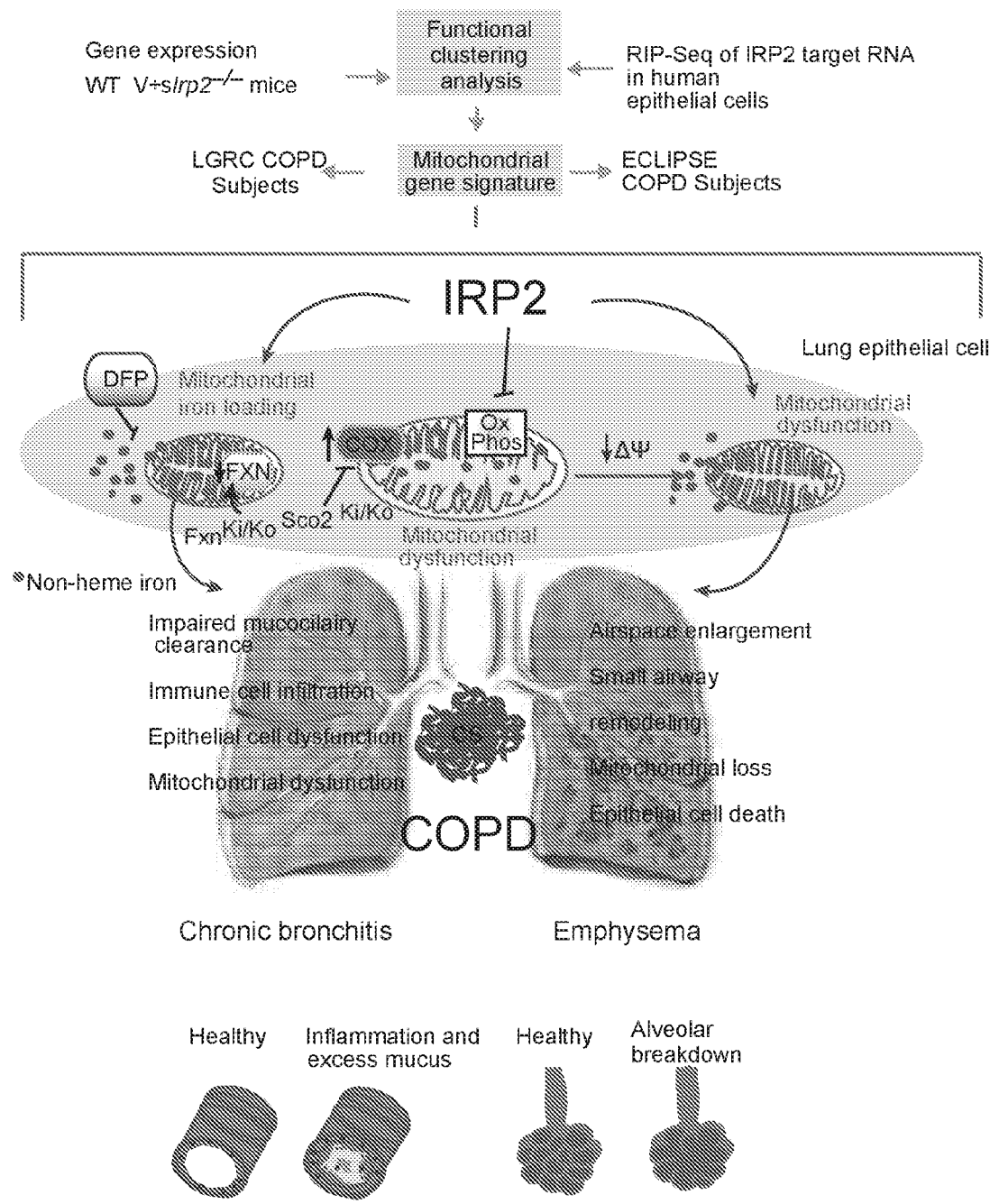
Figure 16:
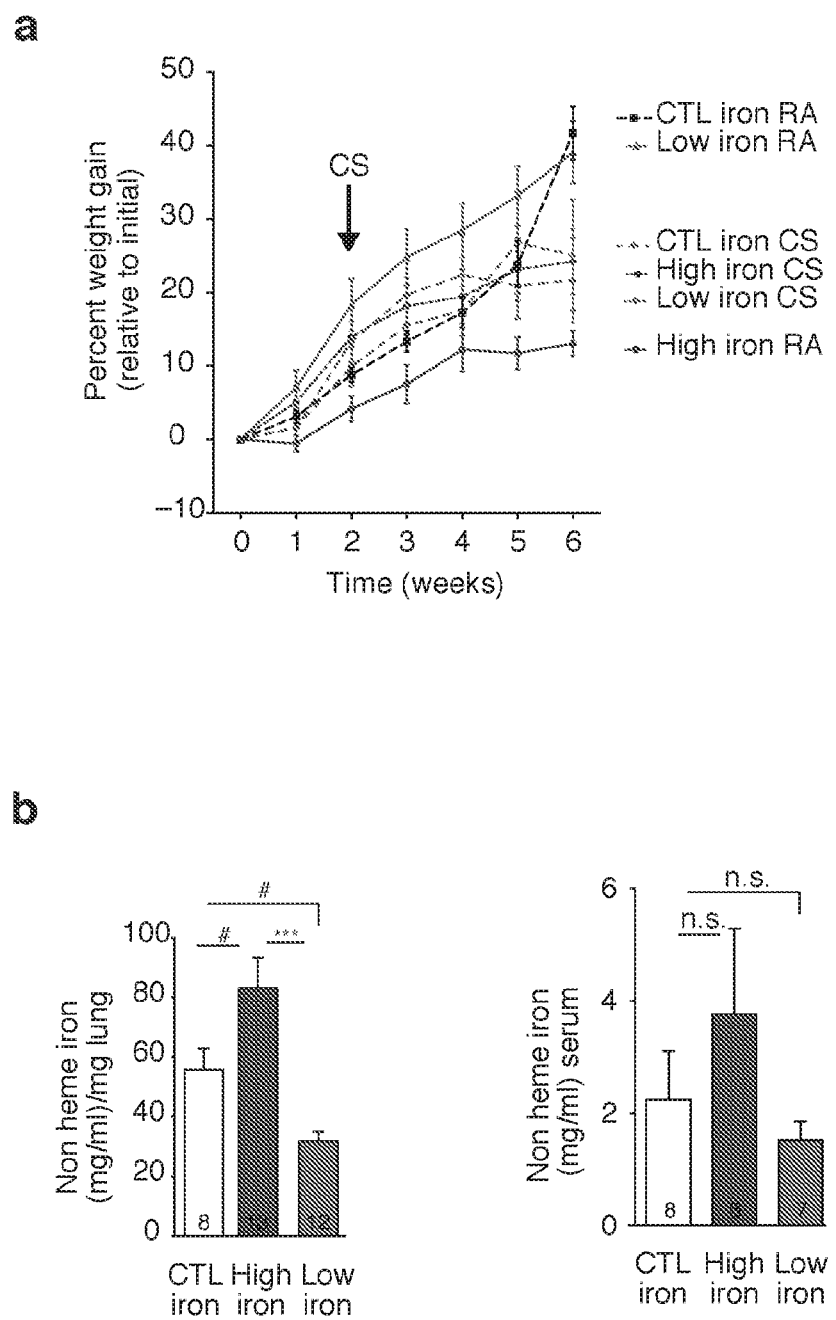
FIG. 16. Mitochondrial iron chelation or a low iron diet alleviates CS-induced bronchitis. (a) Percentage weight gain (left) and non-heme iron content of serum (right) over 6 weeks of WT mice on a control (300 ppm iron), low iron (6 ppm iron) or high iron diet (2% carbonyl iron). (b) Non-heme iron content (left) (CTL n=8; High n=13;low n=12) and serum non-heme iron (right) (CTL n=8; High n=6;low n=7) in mice on a control, low or high iron diet. (c) Total macrophage (left), lymphocyte (middle), PMN (right) BAL cell counts, (d) total BAL IL-33 (ELISA) (control n=9;DFP control n=10; 1 month CS n=6; 6 weeks CS n=6; 6 weeks +DFP n=6; 8 weeks CS n=4; 8 weeks CS +DFP n=5) and (e) whole lung IL-6 (ELISA) expression (control n=8;DFP control n=8; 1 month CS n=9; 6 weeks CS n=5; 6 weeks +DFP n=5; 8 weeks CS n=3; 8 weeks CS +DFP n=5) in WT mice exposed to RA or CS (1 month), followed by treatment with DFP for 2 weeks or 4 weeks, n=2 technical replicates. Black arrows indicate time points and blue arrows indicate time of DFP addition. All data are mean±s.e.m. *P<0.05. P<0.01, *P<0.005 by one-way ANOVA.
Figure 16:
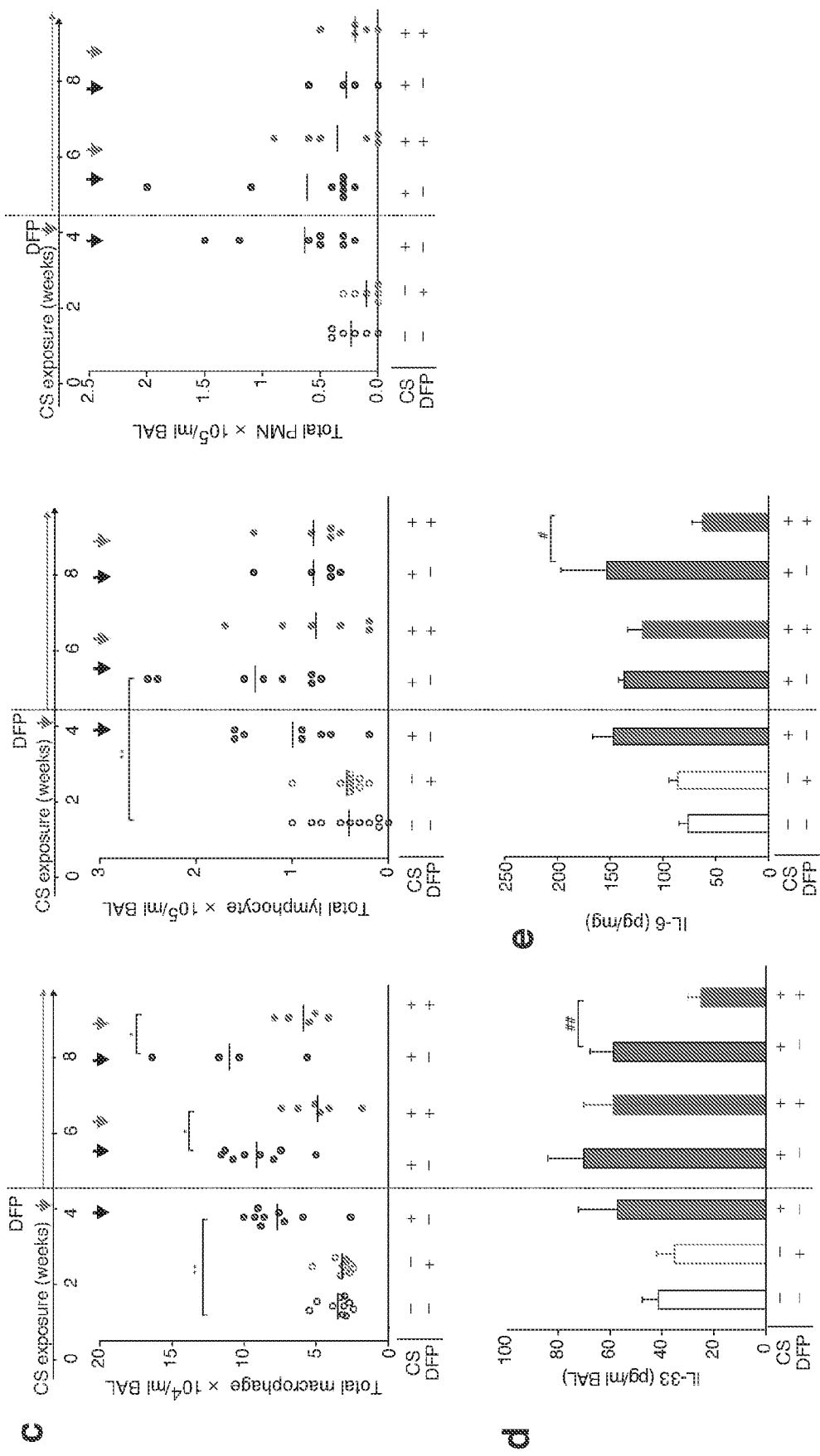

To test the hypothesis that IRP2 increased mitochondrial iron loading, which led to mitochondrial dysfunction in experimental COPD, we first assessed whether modulating iron in the diets of WT mice altered responses to CS in our CS-induced bronchitis model. Mice fed a low-iron diet had lower serum and lower lung non-heme iron levels, and were protected from CS-induced MCC impairment (with no effect on weight gain) when compared to mice fed a control iron diet (FIG. 6a,b and FIG. 16a). Mice fed a high-iron diet had increased non-heme iron (serum and lung) levels and demonstrated impaired weight gain at baseline, but exhibited similar mucociliary responses to CS when compared to mice fed a control iron diet (FIG. 6a,b and FIG. 16a).

We next examined whether alleviating excess mitochondrial iron would alter responses to CS in our CS-induced bronchitis model. Deferiprone (DFP or FERRIPROX®) is an iron chelator that specifically targets mitochondrial non-heme iron deposits and relocates them elsewhere to prevent mitochondrial iron loading. Administration of DFP for the duration of CS-exposure protected mice from CS-induced MCC impairment (FIG. 6c). The protection afforded from DFP treatment was similar to that obtained in the Irp2 –/– mice. Administering DFP and IRP2 deficiency had synergistic effects; specifically DFP-treated Irp2–/– mice had better protection from CS-induced MCC impairment than DFP or Irp2–/– alone (FIG. 6c). Finally, we evaluated whether mitochondrial iron chelation could alleviate established experimental COPD (pulmonary inflammation and injury) when administered as a therapeutic dosing strategy. WT mice with existing impaired MCC (developing after 4 weeks of CS exposure) that were then treated with DFP during an additional 1.5 or 3 weeks of CS exposure had significantly improved mucociliary clearance ($P<0.05$) when compared with mice exposed to CS for the same time period but without DFP (FIG. 6c). Similarly WT mice exposed to CS for 6 or 8 weeks and administered DFP after 4 weeks of CS exposure showed improved weight gain and had lower lung mitochondrial iron loading when compared with mice that were exposed to smoke for 6 or 8 weeks CS but not treated with DFP (FIG. 6d,e). WT mice with CS-induced pulmonary inflammation and injury (increased BAL leukocyte counts and total BALF protein, higher BALF IL-33 protein concentrations and higher whole lung tissue protein levels after 4 weeks of CS exposure) that were then treated with DFP during an additional 2 or 4 weeks of CS exposures also showed significant reductions in pulmonary inflammation (BAL total leukocyte counts, and BALF IL-33 and IL-6 protein concentrations) and acute lung injury (total BALF protein) after 2 and 4 weeks of DFP treatment versus mice exposed to CS for the same duration but not treated with DFP (FIG. 6f,g and FIG. 16c-e).

In this example, we have described characterization of, for the first time the functional role of the gene IRP2 (IREB2) in the pathogenesis of COPD. We confirm that IRP2 promotes COPD in two experimental mouse models of COPD.

Using novel experimental approaches, integrating unbiased IRP2-target identification in cells and mouse lungs with human COPD expression data, we demonstrate that IRP2 regulates mitochondrial-related pathways in the lung. We validate this critical regulation in two well-established human COPD cohorts, showing a strong association between the differential-expression of mitochondrial genes and IRP2 expression in COPD subjects (FIG. 6h). Furthermore, we demonstrate that IRP2 promotes mitochondrial dysfunction in experimental COPD (FIG. 6h), which may ultimately lead to epithelial cell death and emphysematous destruction associated with COPD. It is likely that cells in the lung that rely on mitochondrial function to promote cellular homeostasis maybe affected by increased IRP2 expression. Such cells may include ciliated epithelial cells of the respiratory tract that rely on mitochondria for adenosine triphosphate (ATP) generation for efficient ciliary beat frequency or parenchymal type II alveolar epithelial cells, which reply on their abundant stocks of mitochondria to regulate surfactant production.

Redistributing excessive mitochondrial iron using the membrane-permeant iron chelator DFP alleviated experimental COPD. DFP can not only shuttle iron out of mitochondria, but can also shuttle iron between other cellular organelles (nuclei and endosomes) to extracellular apotransferrin. Mitochondrial-independent effects of DFP may account for the synergistic effects of DFP with IRP2 deficiency in our experimental COPD model (FIG. 6c).

As a consequence of sustained expression of IRP2, COX may increase in airway epithelial cells and may become pathogenic, leading to mitochondrial dysfunction, epithelial cell damage, inflammation and emphysematous destruction in experimental COPD (FIG. 6h). We also illustrate that COX may be a central determinant in the lung for the regulation of mitochondrial iron in response to CS.

Genes such as IRP2 that are involved in cigarette smoke-induced stress responses, particularly those converging on the mitochondria, act as first responders in cellular and possibly systemic iron processing which, if sustained for long periods of time, may have deleterious effects at the molecular, cellular and tissue level leading to mitochondrial dysfunction and subsequent cell death and the initiation of inflammation ultimately resulting in the development of COPD. Our study provides basis for the use of mitochondrial iron chelators as novel therapeutic approaches for COPD.

Accession Codes

RIP-Seq data GEO accession number: GSE57073

WT V's Irp2$^{-/-}$ microarray GEO accession number: GSE57048

Methods

Animals. Irp2$^{-/-}$ and WT littermate control mice were from a mixed genetic background consisting of 12954/SvJae and C57Bl/6 and were from Tracey Rouault (National Institute of Child Health and Human Development). Sco2$^{ki/ki}$ (C57BL/6), Sco2$^{ki/ko}$ (C57BL/6) and WT (C57BL/6) littermate mice were from Eric Schon (Columbia University). Sco2$^{ki/ki}$ have a Sco2 knock-in (KI) mutation on both alleles and Sco2$^{ki/ko}$ have a Sco2 knock-in (KI) mutation on one allele and have Sco2 deleted on the other allele (KO). Wild-type (C57BL/6) and Fxn$^{ki/ko}$ (C57BL/6) were purchased from Jackson Laboratories. Fxn$^{ki/ko}$ mice harbor one allele of the frataxin (GAA) 230Δneo expansion mutation (Fxntm1.1Pand) on one chromosome, and one allele of the frataxin exon 4-deleted mutation (Fxntm1Mkn) on the homologous chromosome. All animals were housed in the same room and kept under a 12-hour light/dark cycle. The iron content of the standard diet was 200 mg/kg. Power was not explicitly calculated for each experiment. Numbers of mice were typically chosen based on prior experiments.

In vivo CS exposures, chemical treatments and diet modifications. Age- and sex-matched mice, starting at 6-12 weeks of age, were selected at random and exposed to total body CS in a stainless steel chamber using a whole-body smoke exposure device (Model TE-10 Teague Enterprises) for 2 hours per day, 5 days per week for 4 weeks or 4-6 months. Age-matched male and female mice were used for all CS exposures. Mice were exposed to CS (mainstream and side stream smoke) from 100 3R4F cigarettes (University of Kentucky), which correlated to an average total particulate matter (TPM) of 150 mg/m$^3$. For animals subjected to cigarette smoke exposure, early death was used as an exclusion criterion. At the end of the exposure regimen, mice were euthanized by $CO_2$ narcosis, the tracheas cannulated and the lungs inflated with PBS at 25 cm of $H_2O$ pressure. The left lung was tied off with a suture, dissected and flash frozen and the right lung fixed in 4% formalin at 4° C. overnight. A proximal portion of the left lung (4 month exposures only) was fixed for transmission electron microscopy (TEM) analysis.

Mice exposed to CS for 4 weeks had modifications to their dietary iron as follows: Diet 1 (Control Diet) from Harlan Laboratories (TD.94045 AIN-93G), which contained 300-ppm iron. Diet 2 (iron deficient diet) from Harlan Laboratories (TD.10210), which contained 2-6 ppm iron. Diet 3 (iron replete Diet) from Harlan Laboratories (TD.10213), which contained 2% carbonyl iron. Iron diets were exchanged for normal diets upon weaning at 3 weeks of age and used throughout the smoke exposures. Animals were weighed weekly and the quantity of chow consumed was recorded compared to mice on a normal iron diet. Deferiprone or FERRIPROX® solution (1mg/ml) (ApoPharma Inc.) was administered prophylactically in the animals' drinking water for the duration of smoke exposure. Deferiprone was also administered therapeutically in the animals' drinking water initiating therapy after 4 weeks of smoke exposure and continuing therapy for an additional 2-4 weeks. Animals were checked daily and the quantity of water consumed compared to control mice. Water solutions were changed twice weekly.

Hyperoxia exposures. Age- and sex-matched Irp2$^{-/-}$ and WT mice (12954/SvJae and C57Bl/6 background), starting at 10 weeks of age, were selected at random and exposed to hyperoxia (>99% $O_2$) at a flow rate of 12 liters/min in a 3.70-ft3 PLEXIGLAS® exposure chamber, with access to chow and water ad libitum during the exposures. Survival was assessed by checking mice at regular intervals over 0-120 hours.

Cecal ligation puncture (CLP) sepsis model. CLP was done as follows. Under aseptic conditions, the abdominal skin of age- and sex-matched Irp2$^{-/-}$ and WT mice (12954/SvJae and C57Bl/6 background), starting at 10 weeks of age selected at random was incised and the abdominal muscles were dissected to gain access to the peritoneal cavity. The mouse cecum was located, 75% of it was ligated with a 6-0 silk suture and was then perforated with a 21 G needle by one through-and-through puncture (two holes) near to the ligation. Sham operated mice underwent the same procedure without ligation and puncture of the exposed cecum. After surgery, 1 ml of prewarmed (37 ° C.) normal saline was injected i.p. to restore heat and hydration of operated mice.

Electrophoretic Mobility Shift Assay (EMSA). IRP2 EMSAs were carried out using the LIGHTSHIFT® Chemiluminescent RNA EMSA Kit (Thermo Scientific) with a biotinylated IRE, according to the manufacturer's instructions. Supershift assays were carried out using 2.5 µg of anti-IRP2 IgG (NB100-1798, Novus Biologicals).

Immunohistochemistry and immunofluorescence staining. Formalin-fixed, paraffin-embedded 5-micron-thick lung sections were prepared and stained using standard procedures. Briefly, sections were deparaffinized through graded alcohols and washed in PBS. Heat-activated antigen retrieval was performed in a microwave oven using a citrate buffer (Target Retrieval Solution, S1699, DAKO) for 10 minutes. Endogenous peroxidases were blocked using a peroxidase blocker (DAKO Cytomation), and the slides were blocked for nonspecific protein binding by incubating in 10% normal serum for 45 minutes. Tissues were immunostained with a rabbit primary IgG to IRP2 (LS-B48, LS Bio) at a 1:50 dilution or mouse anti-cytochrome C, (556433, BD Biosciences) at a 1:250 dilution or with rabbit monoclonal IgG to cytochrome C EPR1327 (D00355 Abcam) at a 1:50 dilution, or with rabbit anti-LC3B (L7543, Sigma Aldrich) at a 1:400 dilution and signals were developed using the VECTASTAIN® Elite ABC Kit (PK-6101; Vector Laboratories), according to the manufacturers protocol. Hematoxylin and Eosin stains were purchased from Sigma Aldrich and staining was carried out as per manufacturer's instructions. The negative control consisted of substituting PBS for the primary antibody.

Epifluorescence microscopy. Briefly, tissues were stained with goat polyclonal IgG to IRP2 (ab106926, Abcam) at a 1:50 dilution or rabbit monoclonal IgG to IRP2 (ab181153, Abcam) at a 1:50 dilution. Co-staining for type II epithelial cells was carried out using a rabbit polyclonal IgG to prosurfactant protein C (Pro-SPC) (ab90716, Abcam) at a 1:50 dilution and for type I epithelial cells using anti-mouse podoplanin ALEXA FLUOR® 488 IgG (53-5381-80, Affymetrix) at a 1:500 dilution. Co-staining for IRP2 and markers of ciliated airway epithelial cells was conducted using a rabbit IgG for acetyl-α-tubulin (Lys40) (D20G3, Cell Signaling) at a 1:50 dilution, and co staining for non-ciliated secretory epithelial cells was conducted using a rabbit polyclonal IgG to uteroglobin (ab40873, Abcam) at a 1:100 dilution. Secondary staining was carried out using goat anti-rabbit IgG (H+L) rhodamine red conjugate (R-6394, Life Technologies) at a 1:500 dilution or donkey anti-goat IgG (H+L) secondary antibody, ALEXA FLUOR® 488 conjugate (A-11055, Life technologies) at a 1:500 dilution. Nuclei were counter-stained using TO-PRO®-3 Iodide (carbocyanine monomer nucleic acid stain) (T3605, Life Technologies) at a 1:1000 dilution or Hoechst (33342, ThermoFisher Scientific) at a 1:300 dilution.

Morphometric analysis of lung sections. Formalin Fixed lung samples were cut parasagitally and embedded in paraffin. Modified Gills staining was performed and air space enlargement was quantified using the mean linear intercept (chord) length (MLI or $L_m$) method (Chen et al. *Proc Natl Acad Sci USA* 107, 18880-18885 (2010)) or using an automated image-processing algorithm that calculates the area weighted mean diameter or $D_2$ index (Parameswaran et al., *Journal of applied physiology* (Bethesda, Md.: 1985) 100, 186-193 (2006)). Briefly, randomized images were acquired (Axiophot; Carl Zeiss Micro-Imaging equipped with a digital camera AXIOCAM® HRc; Carl Zeiss MicroImaging) as black and white TIFF files using a microscope, a 20× objective, and a camera and software that can acquire high-quality digital images. 20-30 images (×200 magnification) were captured per mouse in a randomized manner, with the observer blinded to the experimental condition, avoiding under-inflated areas of the lung (at 20× magnification).

Mean Chord Length measurements: This protocol measures mean alveolar chord length and alveolar area on paraffin-embedded lung sections stained with Gill's stain. Morphometry software converts images of lung sections to binary images (in which tissue is white and airspace is black), and then superimposes a uniform grid of horizontal and vertical lines (chords) and the software then quantifies the length of each chord within areas identified by software as airspace (Laucho-Contreras et al., *J Vis Exp.* 16 (95) (2015). Using this method, it is possible to measure the size of the alveoli in all parts of the lung in a standardized and relatively automated manner. Airspace enlargement was quantified using the MLI method using Scion Image and customized macros to analyze airspace enlargement. Large airways, blood vessels, and other non-alveolar structures were manually removed from the images. The alveolar chord length macro was adapted from the macro available in NIH Image. Alveolar chord length for each image was calculated and the average mean chord length+/−s.e.m. for each mouse calculated.

Measurement of alveolar diameters: This protocol measures the area weighted mean diameter or $D_2$ index. Compared to the Lm, the $D_2$ index characterizes the heterogeneity in airspace sizes. In this study, the $D_2$ index was calculated on paraffin-embedded lung sections stained with Gill's stain with randomized image acquisition as described above. The histological images were first thresholded to create a black and white image where white pixels correspond to air and black pixels correspond to tissue. To avoid errors associated with non-uniform illumination each image was split into non-overlapping blocks and the threshold for each block calculated using the Otsu's method which calculates the optimum threshold to minimize the intraclass variance of the black and white pixels (Nobuyuki, *IEEE Transactions on* 9, 62-66 (1979). The black and white images were then used to calculate a signed distance function where each pixel is assigned the negative of the distance to the nearest black (tissue) pixel. The resulting distance function had a deep minima near the center of each alveolar section and also many shallow local minima close to the alveolar walls created by small local fluctuations in curvature of alveolar walls. The shallow minima were removed by a morphological operator called the H minima transform (Soille, P. Morphological Image Analysis: Principles and Applications. Springer-Verlag, 170-171 (1999). The resulting modified distance map was then segmented using the watershed algorithm (Meyer, *Signal Processing* 38, 113-125 (1994) into distinct regions with each region corresponding to a section of an alveolus. The area occupied by each alveolar section was measured by counting the number of pixels in each region. The measured area was then converted to real units (O (micron$^2$) for mouse alveolar sections) by multiplying with a scaling factor. The area of each alveolar section A. was then converted to an equivalent alveolar diameter, d as $$d = 2\sqrt{\frac{A}{\pi}}.$$

From the measured equivalent diameters the area weighted mean diameter $D_2$ as $$D_2 = \frac{(d^1)}{(d^2)}$$

was calculated.

Small Air remodeling: A morphometry method was used to quantify small airway remodeling in formalin-fixed lung sections from WT, and Irp2$^{-/-}$ mice exposed to RA or CS for 6 months. Briefly, lung sections were stained with Masson's Trichrome stain (Sigma-Aldrich) and images acquired using a light microscope (Axiophot; Carl Zeiss Micro-Imaging) equipped with a digital camera (AXIOCAM® HRc; Carl Zeiss MicroImaging) at 200× magnification by a blinded experienced reader (Laucho-Contreras, *J Vis Exp*. 16 (95) (2015). METAMORPH® software (Molecular Device LLC) was used to measure the mean airway luminal diameter and the thickness of the sub-epithelial fibrosis layer stained blue by Masson's Trichrome stain at 12 separate sites around the airway by a different blinded experienced reader. The mean (±s.e.m.) thickness of the sub-epithelial layer in microns was calculated for airways having a mean internal diameter between 300 and 699 microns. Sections of airways sharing their adventitia with arteries or other airways were not included in the analysis.

BALF isolation, cell counts and ELISA. Mice were euthanized by $CO_2$ narcosis, the tracheas cannulated and the lungs lavaged with 0.5 ml increments of ice-cold PBS eight times (4 ml total). BALF was centrifuged at 500×g for 5 minutes. 1 ml red blood cell lysis buffer (Sigma Aldrich) was added to the cell pellet and left on ice for 15 minutes followed by centrifugation at 600 ×g for 3 minutes. The cell pellet was resuspended in 500 µl PBS and leukocytes were counted using a hemocytometer. Specifically, 20 µl was removed for cell counting performed in triplicate using a hemocytometer and 80 µl removed for cytocentrifuge preparations (Shandon Cytospin3, 300 rpm for 5 minutes) and stained using the Hema3 staining system (Fisher Scientific). The percentage of macrophages, lymphocytes and polymorphonuclear leukocytes (PMNs) were counted in a total of 300 cells, and absolute numbers of each leukocyte subset were calculated.

Commercial ELISAs were used to measure the following analytes in duplicate in homogenates or BALF of lung samples from mice following the manufacturer's instructions: MMP-9 (Mouse Total MMP-9 DUOSET®, DY6718 R&D Systems), cleaved caspase-3 (Human/Mouse Cleaved Caspase-3 (Asp175) DUOSET® IC, R&D Systems DYC835-2), IL-6 (mouse IL-6 DUOSET® R&D Systems DY406), IL-33 (mouse IL-33 DUOSET®, R&D Systems DY3626-05), IL-18 (IL-18/IL1F4 ELISA kit 7625, R&D diagnostics) and IL-1β (Mouse IL-1 beta/IL-1F2 R&D Systems DY401-05).

Assessment of Mucociliary Clearance. Mucociliary clearance was quantified using a non-invasive, oropharyngeal aspiration procedure (Lam et al., The Journal of clinical investigation 123(12), 5212-5230 (2013)). Briefly, mice were anesthetized and 50 µl of normal saline containing approximately 0.3-0.5 mCi of $^{99m}$Technetium sulfur colloid ($^{99m}$Tc-sc) (Brigham and Women's Hospital) was introduced into the distal part of the oropharynx and aspirated. Mouse lungs were imaged immediately after aspiration (time 0 hours), at 1 hour and 3 hours. Whole mouse 3D µ- single-photon emission computed tomography (SPECT) images from 10 minute acquisitions at 0, 1, and 3 hour time points were obtained, reconstructed, blindly analyzed and expressed as the percent removed by mucociliary clearance. Regional lung deposition of $^{99m}$Tc-sc characterized by calculating the central (area closest to the trachea) to peripheral airway distributions ratio (C:P ratio) was corrected for. To correct for any abnormality in distribution, MCC rates were corrected for C: P differences using standard multi-variable linear regression.

RIP-Seq. Three 15 cm$^2$ dishes (1.5×10$^6$ cells) of Beas2B cells (purchased from ATCC) treated with or without 10 µM DFO (16 hours) were washed with ice cold PBS and collected into 2 ml eppendorfs by scraping. RNA immunoprecipitation was carried out using the MAGNA RIP® RNA-Binding Protein Immunoprecipitation Kit (Millipore). 4 µg of mouse IRP2 IgG (7H6: sc-33682, Santa Cruz) or 4 µg of IgG mouse control antibody (sc-2749, Santa Cruz) were added to supernatants and incubated overnight at 4° C. RNA was extracted from MAGNA RIP® beads by Trizol extraction. Samples (n=2 biological replicates) were prepared for RNA-Seq using the TruSeq RNA-Seq Lib Prep Reagent (Illumina) and sequencing performed on the Illumina HiSeq2000 platform. Sample preparation and sequencing was carried out by The Center for Cancer Computational Biology, Dana-Farber Cancer Institute, Boston, Mass.

(cccb.dfci.harvard.edu). RIP-Seq data (GEO accession number GSE57073) was analyzed as follows. Sequenced reads for two biological replicates each in CTL and DFO samples, as well as CTL-IgG and DFO-IgG, were aligned to the human hg19 known transcriptome using bowtie2-2.0.6 and tophat-2.0.7.Linux_x84_64. Any unmapped reads were then allowed to map to the hg19 genome. Aligned reads were then combined from replicates and HOMER (biowhat.ucsd.edu/homer/ngs/index.html) was used to identify and annotate "peaks", or regions enriched for reads in one sample compared to another. Peak-calling was performed on the aligned reads, resulting in the identification of 3497 "common" peaks (mapping to 1806 genes) that were shared between the control (CTL) and DFO samples as well as CTL-specific peaks and DFO-specific peaks. Validation of our data included the detection of peaks in known IRP2 targets, including ferritin and TfR (FIG. 10e,f). We also estimated the percentage of peaks with the known IRE binding motif (CAGWGH) (FIG. 17a).

Four primary comparisons were made: CTL compared to CTL-IgG (CTL/IgG), DFO compared to DFO-IgG (DFO/IgG), CTL compared to DFO (CTL/DFO) and DFO compared to CTL (DFO/CTL). The first two comparisons identified where IRP2 is bound in either CTL or DFO, whereas the latter two comparisons highlight where IRP2 is uniquely bound in only CTL or DFO (FIG. 10d). In each comparison a peak was associated with a genomic region if that peak had a two-fold tag enrichment relative to the input sample, a Poisson P-value less than 0.1 and a peak-score (position-adjusted read counts) greater than 5.

To build a robust set of peaks for further analysis, peaks common between different comparisons were identified using HOMER's 'mergePeaks' function. 3497 "common" peaks where IRP2 is bound in both CTL and DFO, we identified as shared between the CTL/IgG and DFO/IgG comparisons. CTL-specific peaks and DFO-specific peaks were identified by determining peaks common to the CTL/IgG and CTL/DFO or the DFO/IgG and DFO/CTL comparisons respectively (FIG. 10d). For peaks belonging to one of these three sets, we used HOMER's 'annotatePeaks' function to scan the genomic sequence of the peak regions for the known IRE binding motif (CAGWGH)[77] and to map peaks to their target genes. Common peaks mapped to 1806 unique gene transcripts and CTL-specific and DFO-specific peaks mapped to 2203 and 2135 unique gene transcripts, respectively.

Gene Expression Microarray Analysis. The GENECHIP® Mouse Gene 1.0 ST Array (Affymetrix) was used to assess gene expression in the Irp2−/− and WT mice. RNA was isolated from lungs harvested from WT age-matched (n=3 males, 3 females) and Irp2−/− (n=3 males, 3 females) using the RNeasy Mini Kit (Qiagen). The gene expression data GEO accession number GSE57048, was analyzed as follows. GSE57048 was Robust Multi-array Average (RMA)-normalized and probe-sets mapped to Entrez-gene IDs using a custom CDF (Dai et al. *Nucleic acids research* 33, e175 (2005)). To compare the expression data to the RIP-Seq data, we selected 16573 genes on the expression array that belong to a single conserved homologous group (ncbi.nlm.nih.gov/homologene) with the corresponding human homolog identified. For these genes the expression difference between the Irp−/− and WT mice was quantified using an unpaired two-tailed t-test.

Figure 11:
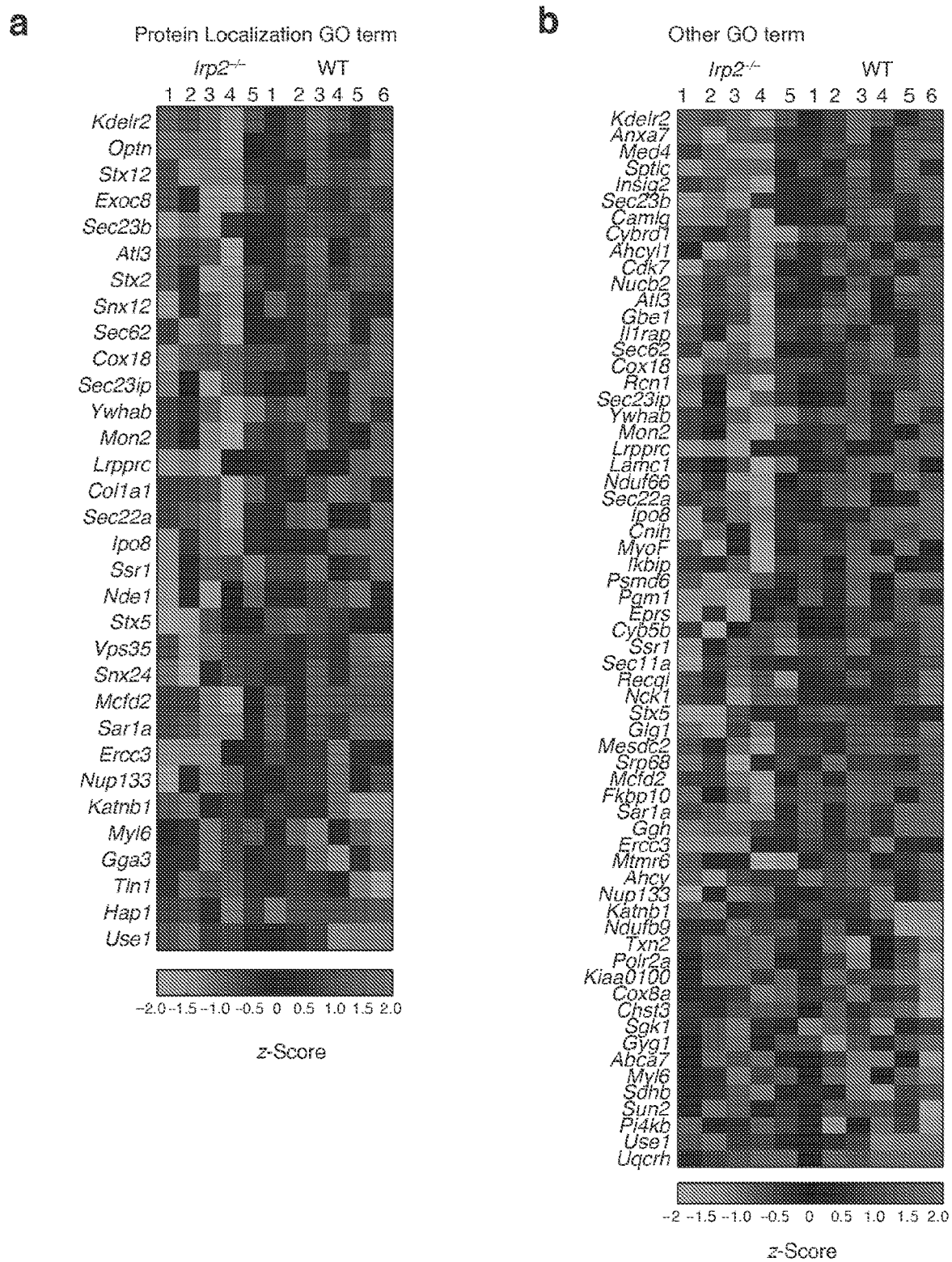
FIG. 11. Within Community 2 we identified three collections of highly related GO categories (see FIG. 3a). These collections are composed of functions related to mitochondria, protein localization or other GO terms. Here we show genes within Community 2 that are significantly differentially-expressed (P<0.01 based on unpaired two-sample t-test), based on a microarray study of lungs from Irp2$^{-/-}$ and WT mice and are also annotated to GO categories within the (a) 'Protein localization' collection of categories or (b) the 'Other' collection of categories. The expression values shown for each gene (row) are z-score normalized for visualization purposes.

Functional Enrichment Clustering Analysis. To evaluate how IRP2 may affect the activity of cellular pathways in the lung, we carried out functional enrichment analysis using the Database for Annotation, Visualization, and Integrated Discovery (DAVID) tool. DAVID analysis (david.abcc.ncifcrf.gov) was carried out on the genes in each of three RIP-Seq defined sets (CTL, DFO and Common), both independently and combined (FIG. 11). To better interpret the results of this analysis, the fast-greedy community structure algorithm (Clauset et al., *Physical review. E, Statistical, nonlinear, and soft matter physics* 70, 066111 (2004) was applied to a network defined by the GO annotations between the genes identified in the RIP-Seq analysis and the GO terms identified as enriched (False discovery rate (FDR) $<1 \times 10^{-3}$) in the DAVID analysis on the combined gene set. This network analysis resulted in the identification of five "communities" containing related sets of genes and terms (FIG. 11). For each "community" identified in the RIP-Seq data, the values of the t-statistic for genes in the community was compared to those not in the community, and a "meta"-t-statistic and associated p-value was computed representing the significance of the association of the Irp2−/− versus WT differential-expression with genes in each of the RIP-Seq "communities" (FIG. 2b). This analysis revealed a strong association between differential-expression and genes in community 2.

Next we selected the genes belonging to community 2 that are also strongly differentially expressed (P<0.01) in Irp2−/− compared to WT mice. We examined to which GO categories (Gene Ontology terms) these genes are annotated, and made three heat maps (FIG. 3a and FIG. 11) based on whether they are annotated to mitochondrial functions (FIG. 3a), protein localization functions (FIG. 11a) or other functions that belong to community 2 (FIG. 5b). In each heat map, the rows were z-score normalized to aid in visualizing differences in expression values.

As RIP-Seq was based on a specific IRP2 antibody that immunoprecipitated IRP2-mRNA complexes only (subtracting IgG-mRNA complexes as background) and then was followed by a comparison to the baseline gene expression in WT versus Irp2−/− lungs, the effects of DFO are therefore not confounded on the functional enrichment clustering analysis carried out in this study and the results are related to IRP2 only. Specifically, 83% (34 of 41) of the genes we show in FIG. 3a were identified as a target of IRP2 in the CRTL v's Igg comparison (so they were either in the "common" or in the "CTRL-only" peaks, or both). Only 7 genes were identified in the DFO-only peak set.

Circos Plot generation. Using the DAVID output from the combined gene-set analysis, a Circos plot was generated to graphically demonstrate the gene transcripts and pathways enriched and /or altered in our CTL-specific (blue), DFO-specific (red) and common (purple) data sets. The inner ring of the Circos plot is colored to represent the five identified functional communities. Since each gene belongs to only one community, genes were assigned to segments of the circle located within their "community". Other genomic information associated with these genes, such as COPD differential expression and RIP-Seq peak scores, was then visualized on different "rings" aligned over these genes.

LGRC gene expression (mRNA) Circos Plots: To identify any common pathways that may be dysregulated by IRP2 in subjects with COPD, on the Circos plot we included gene expression data (mRNA) (FIG. 2a) from lung tissue of individuals with COPD and controls from the Lung Genomics Research Consortium (LGRC; lung-genomics.org/research). The Lung Genomics Research Consortium (lung-genomics.org/research) utilized lung tissue samples from the Lung Tissue Research Consortium and was sponsored and approved by the National Heart, Lung and Blood Institute. Lung tissue mRNA expression data was downloaded from the publicly available LGRC data set GSE47460 (ncbi.nlm.nih.gov/geo/query/acc.cgi?acc=GSE47460). This 159 mRNA gene expression data set contained n=121 COPD, n=20 non-smokers and n=18 smokers. We calculated the fold-change difference between the expression values for each gene in the COPD versus control samples; the inner ring (black ring) of the Circos plot shows the fold-change for genes containing an identified IRP2 peak. Genes with fold-change of more than 1.5 or less than 1/1.5 were highlighted (green denotes lower than COPD, magenta denotes higher in COPD). Circos plot generation allowed for the visualization of similarities and differences between the CTL (blue), DFO (red), common (purple) RIP-Seq peak sets and human COPD RNA-Seq (black).

RNA-Seq Circos plot. We also created a second Circos plot using RNA-Seq data (FIG. 17b) downloaded from the LGRC data portal (lung-genomics.org). Fragments Per Kilobase of transcript per million mapped reads (FPKM) values for 24297 genes and 89 human subject samples were downloaded from LGRC. 59 subjects were subsequently removed for various quality issues, including 15 subjects who were excluded based on either missing DLCO (diffusing capacity for carbon monoxide) values (9 subjects) or DLCO values inconsistent with COPD diagnosis (6 subjects). This left us with 30 samples for analysis, including 23 samples from individuals with COPD (16 ex-smokers, 1 never smoker) and 7 controls (5 ex-smokers, 2 never smokers). We calculated the fold-change difference between the FPKM values for each gene in the COPD versus control samples; the inner ring (black ring) of the Circos plot shows the fold-change for genes containing an identified IRP2 peak. Genes with fold-change of more than 1.5 or less than 1/1.5 were highlighted (green denotes lower than COPD, magenta denotes higher in COPD). Circos plot generation allowed for the visualization of similarities and differences between the CTL (blue), DFO (red), common (purple) RIP-Seq peak sets and human COPD RNA-Seq (black).

Phenotypic Characterization of emphysema and source of tissue. The LGRC provides genetic, molecular, and quantitative phenotype data as well as exclusion criteria, for human subjects in the NHLBI's Lung Tissue Research Consortium (LTRC) biorepository (lung-genomics.org). Lung tissue samples were collected as part of the routine care of patients and submitted with a standardized series of questions. In addition to standard spirometry, DLCO data were available. For controls we included only individuals with a DLCO greater than 80% and for cases DLCO less than 80%.

The LGRC mRNA gene expression data set used the publicly available ncbi.nlm.nih.gov/geo/query/acc.cgi?acc=GSE47460 data set. The 159 mRNA gene expression data set contained n=121 COPD, n=20 non-smokers and n=18 smokers with phenotypic information along with LTRC overall final pathologic diagnosis (CPAL1) as follows in Table 1.

TABLE 1

| CPAL1 | Emphysema, centrilobular | Granulomatous Inflammation (NOS) | Normal | Other |
|---|---|---|---|---|
| COPD | 113 | 2 | 0 | 6 |
| Non-Smoker | 13 | 1 | 4 | 2 |
| Smoker | 14 | 2 | 1 | 1 |

Distributional location of the lung tissue resection (right or left upper or lower lobe), along with pathological diagnosis is described below in Table 2.

TABLE 2

| | Site | | | | | |
|---|---|---|---|---|---|---|
| | Lingula | Left Lower | Left Upper | Right Lower | Right Middle | Right Upper |
| COPD | 1 | 10 | 31 | 14 | 1 | 64 |
| Non-Smoker | 0 | 3 | 3 | 7 | 2 | 5 |
| Smoker | 0 | 3 | 7 | 3 | 1 | 4 |

The RNA-Seq data for 30 subjects used to generate FIG. 17b was downloaded from the data portal (lung-genomics.org). The phenotypic information for this 30 RNA-Seq expression data set cnntainedl as well as source of tissue was as fnllnws in Table 3.

TABLE 3

| CPAL1 | Emphysema, centrilobular | Granulomatous Inflammation (NOS) | Normal | Other |
|---|---|---|---|---|
| COPD | 20 | 1 | 0 | 2 |
| Control | 4 | 1 | 1 | 1 |

Distributional location of the lung tissue resection (right or left upper or lower lobe) is described below in Table 4.

TABLE 4

| | Site | | | | | |
|---|---|---|---|---|---|---|
| | Lingula | Left Lower | Left Upper | Right Lower | Right Middle | Right Upper |
| COPD | 0 | 3 | 3 | 1 | 0 | 16 |
| Control | 0 | 0 | 4 | 1 | 0 | 2 |

Validation of mitochondrial genes in two COPD Cohorts. To compare our identified mitochondrial genes in human COPD lung tissue with high or low IRP2 expression, we used two independent COPD cohort data sets of gene expression.

COPD data set 1. We used publicly available gene expression data from the LGRC (ncbi.nlm.nih.gov/geo/query/acc.cgi?acc=GSE47460). Data collected using each of the two array platforms included was background corrected and then normalized between arrays using limma (Smyth, *Bioinformatics and Computational Biology Solutions Using {R} and Bioconductor*, (Springer, N.Y., 2005). Next we removed duplicate probes and matched between the two array platforms based on gene name. This merged dataset was then corrected for array-specific batch effects using ComBat (Johnson et al., *Biostatistics* (Oxford, England) 8, 118-127 (2007). Of the 580 subjects included in this publicly available data, we identified those with a COPD diagnosis or "control" status (219 and 107 individuals respectively). Approximately half of these subjects were subsequently removed based on quality control, leaving us with a 159 subject mRNA gene expression data set contained n=121 COPD, n=20 non-smokers and n=18 smokers. In this final dataset all subjects with COPD had a DLCO less than 80% and all controls (both smokers and non-smokers) had a DLCO greater than 80%.

COPD data set two. We also used gene expression data from the ECLIPSE (Evaluation of COPD Longitudinally to Identify Predictive Surrogate End-points) Study (Vestbo et al. Eur Respir J 31, 869-873 (2008). This study was a 3-year observational study, where emphysema-predominant COPD was defined by >10% of lung voxels with attenuation ≤−950 HU on inspiratory chest CT scans. Other assessments include pulmonary function measurements (spirometry, impulse oscillometry, chest computed tomography, biomarker measurement (in blood, sputum, urine and exhaled breath condensate), health outcomes, body impedance, resting oxygen saturation and 6 minute walking distance. CEL expression files from ECLIPSE (GSE54837: ncbi.nlm.nih.gov/geo/query/acc.cgi?acc=GSE54837), with "phenotype" information (ncbi.nlm.nih.gov/geo/geo2r/?acc=GSE54837). This particular data set contained 136 COPD subjects, 84 Smoker Controls, 6 non-smoker controls. The ECLIPSE data was RMA-normalized using a custom CDF.

Raw expression data from the two COPD cohorts was downloaded, including raw data files (.TAR) from LGRC (GSE47460), and CEL expression files from ECLIPSE (GSE54837); the ECLIPSE data was RMA-normalized using a custom CDF. We identified which of our selected mitochondrial genes (FIG. 3a) were measured in each of these cohorts and show their expression levels in ECLIPSE and LGRC (FIG. 3b-c and FIG. 11) within different subject populations. In each heat map, the subjects are ordered (from left to right) based on increasing values of IRP2 gene expression, with a white bar delimiting which individuals were identified as having "low" IRP2 expression (less than the median across all subjects) or "high" IRP2 expression (greater than the median across all subjects). Rows are ordered the same as FIG. 3a and each row is Z-score normalized for visualization purposes (FIG. 11).

For LGRC gene expression data set the overall "meta" p-values (for the genes in the heat map) were: COPD-subjects: 1.4e-3, Smoker-controls: 0.9564, Non-smoker controls: 0.5303 (FIG. 11a). For the ECLIPSE data set the overall "meta" p-values (for the genes in the heat map) were: COPD-subjects: 1.4088e-7, Smoker-controls: 6.1838e-6, Non-smoker controls: 1.6108e-5 (FIG. 11b). In all cases the overall differential expression is consistent with observations in the Irp2$^{-/-}$ vs. WT mice (overall decreased expression of these genes in "low" IRP2 compared to "high" IRP2, corresponding to more green on the left of the heat maps.

Transmission electron microscopy. Tissues from mice exposed to chronic CS were fixed overnight at 4° C. using TEM grade fixative solution of 2% formaldehyde and 2.5% glutaraldehyde in 0.1 M sodium cacodylate buffer, pH 7.4. The samples were washed and stored in 0.1 M sodium cacodylate buffer and kept at 4 ° C. until processing. Sample embedding was performed using a standard protocol as previously described[18]. For EM quantification, 15 image fields were selected at random by a blinded reader for each mouse or sample (n=1 mouse per group). The total area of the cytoplasm was calculated, and the number of mitochondria with 'abnormal' characteristics (defined as mitochondria with swollen or abnormal cristae) per unit area of cytoplasm were counted using ImageJ.

Cell Culture, siRNA, shRNA and CSE. Primary epithelial cells were isolated from mouse lungs and used for experiments before passage. Primary Human Bronchial Epithelial cells (HBE) cells were obtained from ATCC and were cultured according to ATCC's instructions. Human lung bronchial epithelial Beas-2B cells were purchased from ATCC and maintained in DMEM containing 10% FBS and gentamicin (100 μg/ml). Beas2B cells were treated with siRNA targeted to human IRP2 (SMARTpool: ON-TARGETplus IREB2 siRNA L-022281, Dharmacon, GE Healthcare) for 48 hours using LIPOFECTAMINE® RNAiMAX Transfection Reagent (Life Technologies) using standard transfection techniques. shRNA targeted to human IREB2 was from Sigma Aldrich (NM_004136, iron-responsive element binding protein 2 MISSION® shRNA). MISSION® shRNA clones in shRNA lentiviral plasmids (pLKO.1-puro) were purchased as frozen bacterial glycerol stocks in Escherichia coli for propagation and downstream purification of the shRNA clones. shRNA viral particles were generated using standard procedures and cells containing positive shRNA clones were selected for using puromycin.

CSE was prepared and added to culture media. A peristaltic pump (VWR International) was used to bubble mainstream smoke from five 3R4F cigarettes with filters removed through 50 ml DMEM. Each cigarette was smoked within 6 minutes until approximately 17 mm remained. The extract was filter sterilized, stored at −80 ° C., and used immediately upon thawing. The CSE generated in this fashion was considered 100% strength and was diluted in complete DMEM media for cell treatment.

Measurement of mitochondrial membrane potential and Cytochrome C oxidase activity. Mitochondrial-enriched fractions were isolated from the lungs of mice and JC1 uptake measured using the MITOISO1 mitochondrial isolation kit (Sigma Aldrich). Mitochondrial membrane potential was measured in primary epithelial cells using tetramethylrhodamine ethyl ester (TMRE) (Abcam). Briefly, cells were treated with CSE or 20 μM carbonilcyanide p-triflouromethoxyphenylhydrazone (FCCP) for the indicated times and stained for 20 minutes at 37° C. with 150 nM TMRE. Data were acquired with a FACSCANTO™ II (BD Biosciences) and analyzed with FLOWJO® analytical software (Tree Star Inc.). Cytochrome C oxidase activity was measured in mitochondrial-enriched fractions using an optimized colorimetric assay based on the decrease in absorbance of ferrocytochrome c measured at 550 nm, which is caused by its oxidation to ferricytochrome c by cytochrome c oxidase (Sigma Aldrich).

Seahorse analysis. Extracellular acidification rates and oxygen consumption rates were determined by the Seahorse XF 96 flux analyzer (Seahorse Bioscience). Primary airway epithelial cells were isolated as described above and plated onto cell culture microplates (Seahorse Bioscience) coated with 50 ng/μl Laminin 1 (3400-010-01, Trevigen) for 4 days (media change on Day 2). On the day of the experiment cells were treated with CSE for 4 hours. Cells were incubated in XF assay medium (Seahorse bioscience), supplemented with 5 mM glucose, 4 mM glutamine and 1 mM pyruvate for one hour prior to the measurement. After the recording of the basal rates of ECAR and OCR, final concentrations of 1 μM oligomycin, 2 μM carbonyl cyanide-4-(trifluoromethoxy) phenylhydrazone (FCCP) and 0.5-0.5 μM rotenone and antimycin A were added (Sigma) through the instruments injection ports in order to obtain proton leak, maximal respiratory capacity and non-mitochondrial respiration respectively. Rates were normalized by DNA with Hoechst 33342 against standards with known concentrations of DNA.

Perls' stain and non-heme iron measurements. Formalin-fixed, paraffin-embedded 5-micron-thick lung sections were deparaffinized through graded alcohols and washed in PBS. Slides were incubated in Perls' stain (5% potassium ferrocyanide with 5% hydrochloric acid) for 30 minutes at RT. 500 μl of nuclear fast red solution was added to each slide and incubated for 4 minutes. Slides were dehydrated using graded alcohols and samples viewed by a blinded experienced reader using a light microscope (Axiophot; Carl Zeiss Micro- Imaging) equipped with a digital camera (Axiocam HRc; Carl Zeiss MicroImaging) at 200× magnification. Perls' stain reacts with iron to form a blue-black color. Staining was quantified in n=3-4 mice per group (n=10 20× images per mouse) by a blinded experienced reader and staining quantified using the Threshold feature in Image J.

Non-heme iron assay: Lung tissue (50-200 mg) or 50-200 µl subcellular fractions were incubated with 100-500 µl of NHI Acid (10% trichloroacetic acid in 3 M HCl) overnight at 65 °C. Samples were cooled, vortexed and centrifuged at 2,000 rpm for 15 seconds. Equal volumes of sample or iron standard (25 µg/ml-0.39 µg/ml using NHI Acid) were incubated in a 1-ml cuvette for 5-10 minutes at RT with 800 µl BAT Buffer (0.2% thioglycolic acid, 0.02% bathophenanthroline sulfonate in 1/2 saturated NaAc solution). Samples were read at 535 nm with unknowns calculated from a standard curve.

Heme iron assay: Heme iron was measured in isolated mitochondrial and cytosolic fractions using the QUANTICHROM® Heme Assay Kit (BioAssay Systems) according to the manufacturers' instructions. Briefly, heme iron was measured in 10 µl mitochondrial and cytosolic fractions by measuring intensity at 400 nm against a standard curve of known concentrations of heme.

Measurement of Labile Iron Pool using Calcein-AM. The labile iron pool of Beas2B cells was measured as follows. $10^6$ Beas2B cells were seeded in 10 cm dish, left overnight, harvested by trypsanization, counted and resuspended in serum free DMEM. Cells were incubated with 0.5 µM CA-AM at 37 °C. for 8 minutes with constant agitation before washing with Hanks' Balanced Salts (HBS) solution (containing phenol red). Cells were resuspended in HBS and incubated with trypan blue (25 µg) to block extracellular fluorescence. Fluorescence was measured at 517 nm emission, 488 nm excitation, measuring the blank rate before the addition of 100 µM salicylaldehyde isonicotinoyl hydrazine (SIH). The change in fluorescence ($\Delta$ F) upon SIH addition was calculated for each sample. In cells without trypan blue, a series of increasing concentrations of calcein were added sequentially and the $\Delta$ F calculated to construct a calcein v's $\Delta$ F standard curve.

Immunoblotting. Immunoblot analyses were performed in whole lung homogenates or mitochondrial-enriched fractions isolated from the lungs of mice using standard immunoblotting techniques with the following antibodies: IRP2 (7H6: sc-33682, Santa Cruz, NB100-1798, Novus Biologicals and IRP2 antibody from Tracey Rouault), IRP1 (NBP1-19412, aconitase 1 Antibody, Novus Biologicals), LC3B (L7543, Sigma Aldrich), Atg 7 (APG7 (H-300): sc-33211, Santa Cruz), transferrin receptor 1 (CD71 (H-300): sc-9099, Santa Cruz), actin (A00158, Sigma Aldrich), electron transport chain components including COX MTCO1 (MITOPROFILE® Total OXPHOS antibody, ab110413, Abcam), ferritin (H-53: sc-25617, Santa Cruz), tom20 (FL-145, sc-11415, Santa Cruz), frataxin (H-155: sc-25820, Santa Cruz), mitoferrin 2 (P-12: sc-138430, Santa Cruz), cleaved-caspase-3 (Asp175, Cell Signaling technologies), Bcl2 (sc-7382, Santa Cruz), FBXL5 (N0039, Neoclone Biotechnology) COX4I2 (H00084701-M01 Abnova) and HO-1 (sc-1797, Santa Cruz).

Real-time qPCR. mRNA was extracted from lung tissue using the Qiagen RNA extraction kit (74104, Qiagen) and reverse transcribed with SUPERSCRIPT® III Reverse Transcriptase (Life Technologies). TAQMAN® primers for gene expression assays were purchased from Life Technologies. Real-time qPCR was carried out with an ABI PRISM 7300 Sequence Detection System using TAQMAN® PCR Master Mix (Life Technologies). mRNA was extracted from cells using the Qiagen RNA extraction kit (74104, Qiagen) and reverse transcribed with SUPERSCRIPT® III Reverse Transcriptase (Life Technologies). mRNA in FIG. 10f was used from RIP-Seq library preparations. TAQMAN® primers for human transferrin Receptor 1, human ferritin Heavy chain, human frataxin and human beta-actin for gene expression assays were purchased from Life Technologies. Real-time qPCR was carried out with an ABI PRISM 7300 Sequence Detection System using TAQMAN® PCR Master Mix (Life Technologies).

Flow cytometry. To discriminate live and dead cells, cells were simultaneously stained with green fluorescent calcein-AM to indicate intracellular esterase activity and red fluorescent ethidium homodimer-1 to indicate loss of plasma membrane integrity using the LIVE/DEAD® Viability/Cytotoxicity Kit (L-3224, Molecular Probes). mtROS was measured in cells by MITOSOX® (M36008, Invitrogen) staining (2.5 µM for 10 minutes at 37 °C.). Data were acquired with a FACSCANTO™ II (BD Biosciences) and analyzed with FLOWJO® analytical software (Tree Star Inc.).

Confocal Imaging. 80,000 Beas2B cells seeded onto poly-L-lysine coated cover slips in a 6 well plate were treated with CSE for the indicated times. The cells were permeabilized for 15 minutes in 0.01% Triton-X 100 then washed in PBS twice and 0.5% bovine serum albumin (BSA) in PBS twice. The cells were blocked for 45 minutes with 2% BSA in PBS. The cells were washed once in 0.5% BSA and then incubated for 1 hour at room temperature with a primary rabbit IgG to human IRP2 (1:100, sc-33682, Santa Cruz). The samples were washed 5 times with 0.5% BSA and then incubated for 1 hour at room temperature in secondary IgG ALEXA FLUOR® 488 anti- rabbit (1:400). Nuclei were stained using DAPI.

Measurement of Fe—S cluster assembly in Beas2B cells. 2Fe—S clusters were measured in Beas2B cells as follows. $8\times10^5$ Beas2B cells were transfected with constructs (0.8 µm) containing venus fluorescent protein fragments targeted to the mitochondrion or cytosol and conjugated to human glutaredoxin 2 (GRX2) which coordinates 2Fe2S clusters for 24 h. Transfected cells were treated with 20% CSE for 0.5, 1 or 2 hours. The fluorescence of cells transiently transfected with vectors that express mitochondrial and cytosolic Venus-fragment pairs fused GRX2 was determined using flow cytometry (measuring FITC fluorescence). The fluorescence of Venus fragments fused to the self-associating leucine zipper region of the yeast Gcn4 transcriptional activator were used as a control for Venus fragments that stably associate (data not shown).

Statistical analysis. Statistical analysis was conducted using GRAPHPAD PRISM® software (GraphPad Software). Data are presented as the mean±s.e.m. from at least two independent experiments. Differences in measured variables between experimental and control groups were assessed using the unpaired Student's t test and between multiple groups and conditions using one-way and two-way ANOVAs with subsequent Bonferroni-corrected pairwise tests. For MCC assays, a significant P value was followed by a pair-wise comparison using a two-sample t test for a priori hypotheses only. Thus, no adjustment in the significance level was made for multiple comparisons. Multi-variable regression was conducted using STATA/IC (v13) to isolate the effects of IRP2, C:P ratio, DFP, CS, and iron diets (FIG. 6a,c). P values were calculated and minimum statistical significance was accepted at $P<0.05$.

Human Samples and Study Approval. Human Lung tissues were analyzed under the guidelines of Brigham and Women's Hospital Institutional Review Board (IRB) approval. Human samples were classified based on the guidelines of the Global Initiative for Obstructive Lung Disease (as described in Mizumura et al. *The Journal of clinical investigation* 124, 3987-4003 (2014); Lam et al. *The Journal of clinical investigation* 123(12), 5212-5230 (2013); An, et al. *American journal of physiology. Lung cellular and molecular physiology* 303, L748-757 (2012)). Human samples obtained from the Lung Genomics Tissue Research Consortium (LTRC) used in FIG. 5a were homogenates from tissues obtained from open lung biopsies and are described in Table 5. The Lung Genomics Research Consortium (LGRC) provides genetic, molecular, and quantitative phenotype data for human samples in the National Heart, Lung and Blood Institute LTRC biorepository (lung-genomics.org). Informed consent was obtained from all subjects included in these studies.

All animal experimental protocols were approved by the Harvard Standing Committee for Animal Welfare and by the Institutional Animal Care and Use Committees of Brigham and Women's Hospital.

TABLE 5

Clinical information of human lung specimens LGRC.

|  | Never-Smokers (N = 5) | COPD GOLD 2 (N = 5) |
|---|---|---|
| Age, yr. | 79 ± 3 | 70 ± 3 |
| Smoking index at entry, pack-years | 0 ± 0 | 52 ± 4* |
| Lung function |  |  |
| FVC, % predicted | 99.8 ± 5.2 | 91.3 ± 2.8 |
| $FEV_1$, % predicted | 102.4 ± 5.7 | 66.3 ± 1.9*# |
| $FEV_1/FVC$ | 0.76 ± 0.02 | 0.53 ± 0.01*# |
| Emphysema score | 0.0 ± 0.0 | 1.3 ± 0.3 |

Definition of abbreviations;
COPD = chronic obstructive pulmonary disease;
GOLD = The Global Initiative for Obstructive Lung Disease;
FVC = forced vital capacity;
$FEV_1$ = forced expiratory volume in one second.
Data expressed as mean ± standard error of the mean (SEM).
*$p < 0.05$, compared with the never-smoker group.
$p < 0.05$, compared with the ever-smoker group.

While the invention has been described through various embodiments, routine modifications will be apparent to those skilled in the art, which modifications are intended to be within the scope of the disclosure.

What is claimed is:

1. A method for treating chronic obstructive pulmonary disease (COPD) comprising administering to an individual in need of treatment a therapeutically effective amount of a composition comprising a mitochondrial iron chelator wherein the mitochondrial chelator is deferiprone or pegylated derivatives thereof.

2. The method of claim 1, wherein the composition is present in an aerosolized form.

3. The method of claim 1, wherein the composition is administered via an oral route.

4. The method of claim 1, wherein the composition is administered by inhalation.

5. The method of claim 1, wherein the composition is administered via a cutaneous route.

6. The method of claim 1, wherein the composition does not contain any other agent that has a therapeutic effect for COPD.

7. The method of claim 1, wherein the composition does not contain any other iron chelator.

8. The method of claim 1, wherein the composition further comprises an agent that has a therapeutic effect for COPD.

9. The method of claim 1, wherein the individual is a smoker.

10. The method of claim 9, wherein the individual has ceased smoking.

11. The method of claim 1, wherein deferiprone is administered over a period of at least 3 weeks.

12. The method of claim 11, wherein deferiprone is administered over a period of at least 4 weeks.

* * * * *